United States Patent
Fish et al.

(10) Patent No.: US 10,973,632 B2
(45) Date of Patent: Apr. 13, 2021

(54) PERCUTANEOUSLY DELIVERABLE HEART VALVE INCLUDING FOLDED MEMBRANE CUSPS WITH INTEGRAL LEAFLETS

(71) Applicant: Colibri Heart Valve LLC, Broomfield, CO (US)

(72) Inventors: R. David Fish, Houston, TX (US); Eduardo Induni, Alajuela (CR); David Paniagua, Houston, TX (US)

(73) Assignee: COLIBRI HEART VALVE LLC, Lousiville, CO (US)

( * ) Notice: Subject to any disclaimer, the term of this patent is extended or adjusted under 35 U.S.C. 154(b) by 0 days.

(21) Appl. No.: 15/680,350

(22) Filed: Aug. 18, 2017

(65) Prior Publication Data
US 2018/0185143 A1    Jul. 5, 2018

Related U.S. Application Data

(62) Division of application No. 13/326,196, filed on Dec. 14, 2011, now Pat. No. 9,737,400.

(60) Provisional application No. 61/423,051, filed on Dec. 14, 2010.

(51) Int. Cl.
*A61F 2/24*    (2006.01)

(52) U.S. Cl.
CPC .......... *A61F 2/2415* (2013.01); *A61F 2/2418* (2013.01); *A61F 2220/0075* (2013.01); *A61F 2230/0054* (2013.01)

(58) Field of Classification Search
CPC ................................. A61F 2/24; A61F 2/2415
See application file for complete search history.

(56) References Cited

U.S. PATENT DOCUMENTS

| | | | |
|---|---|---|---|
| 3,014,024 A | 12/1961 | Lieberman et al. |
| 3,029,819 A | 4/1962 | Edward |
| 3,105,492 A | 10/1963 | Jeckel |
| 3,320,972 A | 5/1967 | High et al. |

(Continued)

FOREIGN PATENT DOCUMENTS

| EP | 0696447 | 1/2000 |
|---|---|---|
| EP | 1603493 | 12/2005 |

(Continued)

OTHER PUBLICATIONS

Examination Report dated Jul. 23, 2020 and issued in Australian Patent Application No. 2019204445.

(Continued)

*Primary Examiner* — Matthew W Schall
(74) *Attorney, Agent, or Firm* — Fox Rothschild LLP

(57) ABSTRACT

A transcatheter, percutaneously implantable, prosthetic heart valve is provided that comprises a lattice frame and two or more integrated cusp and leaflet folded structures attached to the lattice frame. The two or more integrated cusp and leaflet folded structures each comprise a flat sheet of biocompatible membrane that is folded to include a substantially conical shape according to a flat folding pattern. The substantially conical shape is further formed by joining apposing sides of the substantially conical shape along a seam. The two or more integrated cusp and leaflet folded structures are each attached along their respective seams to the lattice frame in a direction substantially parallel to an axis of the lattice frame. Embodiments of valves described herein have application within the entire vascular system.

34 Claims, 28 Drawing Sheets

(56) References Cited

U.S. PATENT DOCUMENTS

| | | |
|---|---|---|
| 3,409,914 A | 11/1968 | Jones |
| 3,548,417 A | 12/1970 | Kischer et al. |
| 3,562,820 A | 2/1971 | Braun |
| 3,588,920 A | 6/1971 | Wesolowski |
| 3,671,979 A | 6/1972 | Moulopoulos |
| 3,709,175 A | 1/1973 | Edwards et al. |
| 3,878,565 A | 4/1975 | Sauvage |
| 3,945,052 A | 3/1976 | Liebig |
| 3,966,401 A | 6/1976 | Hancock et al. |
| 3,983,581 A | 10/1976 | Angell et al. |
| 3,986,828 A | 10/1976 | Hoffman, Jr. et al. |
| 4,011,947 A | 3/1977 | Sawyer |
| 4,035,849 A | 7/1977 | Angell et al. |
| 4,055,861 A | 11/1977 | Carpentier et al. |
| 4,056,854 A | 11/1977 | Boretos et al. |
| 4,060,081 A | 11/1977 | Yannas et al. |
| 4,082,507 A | 4/1978 | Sawyer |
| 4,084,268 A | 4/1978 | Ionescu et al. |
| 4,106,129 A | 8/1978 | Carpentier et al. |
| 4,164,045 A | 8/1979 | Bokros et al. |
| 4,172,295 A | 10/1979 | Batten |
| 4,218,782 A | 8/1980 | Rygg |
| 4,222,126 A | 9/1980 | Boretos et al. |
| 4,233,493 A | 11/1980 | Nath |
| 4,265,694 A | 5/1981 | Boretos et al. |
| 4,275,469 A | 6/1981 | Gabbay |
| 4,291,420 A | 9/1981 | Reul |
| 4,340,977 A | 7/1982 | Brownlee et al. |
| 4,350,492 A | 9/1982 | Wright et al. |
| 4,364,127 A | 12/1982 | Pierce et al. |
| 4,388,735 A | 6/1983 | Ionescu et al. |
| 4,423,525 A | 1/1984 | Vallana et al. |
| 4,441,216 A | 4/1984 | Ionescu et al. |
| 4,456,589 A | 6/1984 | Holman et al. |
| 4,473,423 A | 9/1984 | Kolff |
| 4,477,930 A | 10/1984 | Totten et al. |
| 4,490,859 A | 1/1985 | Black et al. |
| 4,491,986 A | 1/1985 | Gabbay |
| 4,517,687 A | 5/1985 | Liebig et al. |
| 4,545,082 A | 10/1985 | Hood |
| 4,553,974 A | 11/1985 | Dewanjee |
| 4,597,762 A | 7/1986 | Walter et al. |
| 4,600,533 A | 7/1986 | Chu |
| 4,631,052 A | 12/1986 | Kensey |
| 4,657,133 A | 4/1987 | Komatsu et al. |
| 4,666,442 A | 5/1987 | Arru et al. |
| 4,692,164 A | 9/1987 | Dzemeshkevich et al. |
| 4,728,328 A | 3/1988 | Hughes et al. |
| 4,743,231 A | 5/1988 | Kay et al. |
| 4,759,758 A | 7/1988 | Gabbay |
| 4,759,759 A | 7/1988 | Walker et al. |
| 4,798,611 A | 1/1989 | Freeman, Jr. |
| 4,801,299 A | 1/1989 | Brendel et al. |
| 4,870,966 A | 10/1989 | Dellon et al. |
| 4,883,458 A | 11/1989 | Shiber |
| 4,892,539 A | 1/1990 | Koch |
| 4,966,604 A | 10/1990 | Reiss |
| 4,976,733 A | 12/1990 | Girardot |
| 4,979,939 A | 12/1990 | Shiber |
| 5,006,104 A | 4/1991 | Smith et al. |
| 5,007,896 A | 4/1991 | Shiber |
| 5,011,488 A | 4/1991 | Ginsburg |
| 5,026,366 A | 6/1991 | Leckrone |
| 5,032,128 A | 7/1991 | Alonso |
| 5,047,041 A | 9/1991 | Samuels |
| 5,047,050 A | 9/1991 | Arpesani |
| 5,052,771 A | 10/1991 | Williams et al. |
| 5,061,277 A | 10/1991 | Carpentier et al. |
| 5,080,660 A | 1/1992 | Buelna |
| 5,080,670 A | 1/1992 | Imamura et al. |
| 5,139,515 A | 8/1992 | Robicsek |
| 5,163,955 A | 11/1992 | Love et al. |
| 5,171,273 A | 12/1992 | Silver et al. |
| 5,226,889 A | 7/1993 | Sheiban |
| 5,261,878 A | 11/1993 | Galindo |
| 5,282,847 A | 2/1994 | Trescony et al. |
| 5,326,370 A | 7/1994 | Love et al. |
| 5,326,371 A | 7/1994 | Love et al. |
| 5,332,402 A | 7/1994 | Teitelbaum |
| 5,336,616 A | 8/1994 | Livesey et al. |
| 5,344,442 A | 9/1994 | Deac |
| 5,360,443 A | 11/1994 | Barone et al. |
| 5,374,539 A | 12/1994 | Nimni et al. |
| 5,376,110 A | 12/1994 | Tu et al. |
| 5,383,927 A | 1/1995 | De Goicoechea et al. |
| 5,411,552 A | 5/1995 | Andersen et al. |
| 5,413,601 A | 5/1995 | Keshelava |
| 5,449,384 A | 9/1995 | Johnson |
| 5,476,506 A | 12/1995 | Lunn |
| 5,480,424 A | 1/1996 | Cox |
| 5,484,444 A | 1/1996 | Braunschweiler et al. |
| 5,489,297 A | 2/1996 | Duran |
| 5,500,015 A | 3/1996 | Deac |
| 5,509,930 A | 4/1996 | Love |
| 5,522,879 A | 6/1996 | Scopelianos |
| 5,522,881 A | 6/1996 | Lentz |
| 5,545,215 A | 8/1996 | Duran |
| 5,549,664 A | 8/1996 | Hirata et al. |
| 5,549,666 A | 8/1996 | Hata et al. |
| 5,554,184 A | 9/1996 | Machiraju |
| 5,558,875 A | 9/1996 | Wang |
| 5,571,170 A | 11/1996 | Palmaz et al. |
| 5,571,173 A | 11/1996 | Parodi |
| 5,571,174 A | 11/1996 | Love et al. |
| 5,578,071 A | 11/1996 | Parodi |
| 5,578,072 A | 11/1996 | Barone et al. |
| 5,582,168 A | 12/1996 | Samuels et al. |
| 5,591,229 A | 1/1997 | Parodi |
| 5,634,928 A | 6/1997 | Fischell et al. |
| 5,645,559 A | 7/1997 | Hachtman et al. |
| 5,653,749 A | 8/1997 | Love et al. |
| 5,683,451 A | 11/1997 | Lenker et al. |
| 5,713,953 A | 2/1998 | Vallana et al. |
| 5,728,152 A | 3/1998 | Mirsch, II et al. |
| 5,733,299 A | 3/1998 | Sheiban et al. |
| 5,741,333 A | 4/1998 | Frid |
| 5,746,775 A | 5/1998 | Levy et al. |
| 5,769,780 A | 6/1998 | Hata et al. |
| 5,782,914 A | 7/1998 | Schankereli |
| 5,787,887 A | 8/1998 | Klingenbeck-Regn |
| 5,840,081 A | 11/1998 | Andersen et al. |
| 5,855,597 A | 1/1999 | Jayaraman |
| 5,855,601 A | 1/1999 | Bessler et al. |
| 5,861,028 A | 1/1999 | Angell |
| 5,862,806 A | 1/1999 | Cheung |
| 5,876,448 A | 3/1999 | Thompson et al. |
| 5,895,420 A | 4/1999 | Mirsch, II et al. |
| 5,931,969 A | 8/1999 | Carpentier et al. |
| 5,957,949 A | 9/1999 | Leonhardt et al. |
| 5,961,539 A | 10/1999 | Northrup, III et al. |
| 5,961,549 A | 10/1999 | Nguyen et al. |
| 5,972,030 A | 10/1999 | Garrison et al. |
| 5,976,179 A | 11/1999 | Inoue |
| 6,004,328 A | 12/1999 | Solar |
| 6,004,330 A | 12/1999 | Middleman et al. |
| 6,010,531 A | 1/2000 | Donlon et al. |
| 3,029,671 A | 2/2000 | Stevens et al. |
| 3,045,576 A | 4/2000 | Starr et al. |
| 3,053,938 A | 4/2000 | Goldmann et al. |
| 6,077,295 A | 6/2000 | Limon et al. |
| 6,091,984 A | 7/2000 | Perelman et al. |
| 6,102,944 A | 8/2000 | Huynh et al. |
| 6,117,169 A | 9/2000 | Moe |
| 6,124,523 A | 9/2000 | Banas et al. |
| 6,125,852 A | 10/2000 | Stevens et al. |
| 6,126,686 A | 10/2000 | Badylak et al. |
| 6,129,756 A | 10/2000 | Kugler et al. |
| 6,162,245 A | 12/2000 | Jayaraman |
| 6,168,614 B1 | 1/2001 | Andersen et al. |
| 6,168,619 B1 | 1/2001 | Dinh et al. |
| 6,171,335 B1 | 1/2001 | Wheatley et al. |
| 6,174,327 B1 | 1/2001 | Mertens et al. |
| 6,186,999 B1 | 2/2001 | Chen |
| 6,197,143 B1 | 3/2001 | Bodnar |

(56) References Cited

U.S. PATENT DOCUMENTS

| | | |
|---|---|---|
| 6,214,055 B1 | 4/2001 | Simionescu et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,254,629 B1 | 7/2001 | Inoue |
| 6,254,630 B1 | 7/2001 | Inoue |
| 6,254,636 B1 | 7/2001 | Peredo |
| 6,264,691 B1 | 7/2001 | Gabbay |
| 6,269,819 B1 | 8/2001 | Oz et al. |
| 6,270,526 B1 | 8/2001 | Cox |
| 6,277,397 B1 | 8/2001 | Shimizu |
| 6,277,555 B1 | 8/2001 | Duran et al. |
| 6,287,334 B1 | 9/2001 | Moll et al. |
| 6,287,335 B1 | 9/2001 | Drasler et al. |
| 6,293,970 B1 | 9/2001 | Wolfinbarger, Jr. et al. |
| 6,312,462 B1 | 11/2001 | McDermott et al. |
| 6,312,474 B1 | 11/2001 | Francis et al. |
| 6,334,873 B1 | 1/2002 | Lane et al. |
| 6,342,069 B1 | 1/2002 | Deac et al. |
| 6,350,278 B1 | 2/2002 | Lenker et al. |
| 6,350,282 B1 | 2/2002 | Eberhardt |
| 6,352,554 B2 | 3/2002 | De Paulis |
| 6,352,708 B1 | 3/2002 | Duran et al. |
| 6,358,275 B1 | 3/2002 | McIlroy et al. |
| 6,358,284 B1 | 3/2002 | Fearnot et al. |
| 6,371,980 B1 | 4/2002 | Rudakov et al. |
| 6,376,244 B1 | 4/2002 | Atala |
| 6,378,221 B1 | 4/2002 | Ekholm, Jr. et al. |
| 6,383,171 B1 | 5/2002 | Gifford et al. |
| 6,391,333 B1 | 5/2002 | Li et al. |
| 6,409,755 B1 | 6/2002 | Vrba |
| 6,418,339 B1 | 7/2002 | Essenpreis et al. |
| 6,425,916 B1 | 7/2002 | Garrison et al. |
| 6,432,712 B1 | 8/2002 | Wolfinbarger, Jr. |
| 6,440,164 B1 | 8/2002 | DiMatteo et al. |
| 6,440,167 B2 | 8/2002 | Shimizu |
| 6,458,153 B1 | 10/2002 | Bailey et al. |
| 6,461,382 B1 | 10/2002 | Cao |
| 6,468,313 B1 | 10/2002 | Claeson et al. |
| 6,471,723 B1 | 10/2002 | Ashworth et al. |
| 6,482,227 B1 | 11/2002 | Solovay |
| 6,482,228 B1 | 11/2002 | Norred |
| 6,482,240 B1 | 11/2002 | Eckmayer et al. |
| 6,491,719 B1 | 12/2002 | Fogarty et al. |
| 6,494,909 B2 | 12/2002 | Greenhalgh |
| 6,503,272 B2 | 1/2003 | Duerig et al. |
| 6,530,952 B2 | 3/2003 | Vesely |
| 6,534,004 B2 | 3/2003 | Chen et al. |
| 6,540,782 B1 | 4/2003 | Snyders |
| 6,553,681 B2 | 4/2003 | Ekholm, Jr. et al. |
| 6,558,418 B2 | 5/2003 | Carpentier et al. |
| 6,565,960 B2 | 5/2003 | Koob et al. |
| 6,569,200 B2 | 5/2003 | Wolfinbarger, Jr. et al. |
| 6,582,458 B1 | 6/2003 | White et al. |
| 6,582,462 B1 | 6/2003 | Andersen et al. |
| 6,582,464 B2 | 6/2003 | Gabbay |
| 6,599,524 B2 | 7/2003 | Li et al. |
| 6,610,088 B1 | 8/2003 | Gabbay |
| 6,624,890 B2 | 9/2003 | Backman et al. |
| 6,626,938 B1 | 9/2003 | Butaric et al. |
| 6,652,577 B2 | 11/2003 | Gianotti |
| 6,652,578 B2 | 11/2003 | Bailey et al. |
| 6,666,886 B1 | 12/2003 | Tranquillo et al. |
| 6,676,698 B2 | 1/2004 | McGuckin, Jr. et al. |
| 6,682,537 B2 | 1/2004 | Ouriel et al. |
| 6,682,559 B2 | 1/2004 | Myers et al. |
| 6,685,739 B2 | 2/2004 | DiMatteo et al. |
| 6,696,074 B2 | 2/2004 | Dai et al. |
| 6,702,826 B2 | 3/2004 | Liddicoat et al. |
| 6,719,788 B2 | 4/2004 | Cox |
| 6,719,789 B2 | 4/2004 | Cox |
| 6,730,118 B2 | 5/2004 | Spenser et al. |
| 6,733,525 B2 | 5/2004 | Yang et al. |
| 6,736,823 B2 | 5/2004 | Darois et al. |
| 6,764,510 B2 | 7/2004 | Vidlund et al. |
| 6,773,456 B1 | 8/2004 | Gordon et al. |
| 6,773,457 B2 | 8/2004 | Ivancev et al. |
| 6,790,229 B1 | 9/2004 | Berreklouw |
| 6,792,979 B2 | 9/2004 | Konya et al. |
| 6,802,319 B2 | 10/2004 | Stevens et al. |
| 6,802,806 B2 | 10/2004 | McCarthy et al. |
| 6,821,297 B2 | 11/2004 | Snyders |
| 6,821,530 B2 | 11/2004 | Koob et al. |
| 6,830,584 B1 | 12/2004 | Seguin |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,608 B2 | 7/2005 | Liddicoat et al. |
| 6,916,338 B2 | 7/2005 | Speziali |
| 6,942,694 B2 | 9/2005 | Liddicoat et al. |
| 6,951,571 B1 | 10/2005 | Srivastava |
| 6,961,123 B1 | 11/2005 | Wang et al. |
| 6,977,231 B1 | 12/2005 | Matsuda |
| 6,986,735 B2 | 1/2006 | Abraham et al. |
| 7,004,925 B2 | 2/2006 | Navia et al. |
| 7,008,763 B2 | 3/2006 | Cheung |
| 7,011,688 B2 | 3/2006 | Gryska et al. |
| 7,018,404 B2 | 3/2006 | Holmberg et al. |
| 7,018,406 B2 | 3/2006 | Seguin et al. |
| 7,022,348 B2 | 4/2006 | Ketharanathan |
| 7,025,780 B2 | 4/2006 | Gabbay |
| 7,037,333 B2 | 5/2006 | Myers et al. |
| 7,039,446 B2 | 5/2006 | Ruchti et al. |
| 7,041,132 B2 | 5/2006 | Quijano et al. |
| 7,053,051 B2 | 5/2006 | Hendriks et al. |
| 7,060,092 B2 | 6/2006 | Kuribayashi et al. |
| 7,070,616 B2 | 7/2006 | Majercak et al. |
| 7,077,862 B2 | 7/2006 | Vidlund et al. |
| 7,084,082 B1 | 8/2006 | Shimizu |
| 7,138,226 B2 | 11/2006 | Vincek et al. |
| 7,153,324 B2 | 12/2006 | Case et al. |
| 7,160,322 B2 | 1/2007 | Gabbay |
| 7,164,145 B2 | 1/2007 | Shakespeare |
| 7,166,570 B2 | 1/2007 | Hunter et al. |
| 7,189,259 B2 | 3/2007 | Simionescu et al. |
| 7,213,601 B2 | 5/2007 | Stevens et al. |
| 7,214,242 B2 | 5/2007 | Abraham et al. |
| 7,214,344 B2 | 5/2007 | Carpentier et al. |
| 7,232,461 B2 | 6/2007 | Ramer |
| 7,261,732 B2 | 8/2007 | Justino |
| 7,289,211 B1 | 10/2007 | Walsh, Jr. et al. |
| 7,309,461 B2 | 12/2007 | Kujawski et al. |
| 7,311,730 B2 | 12/2007 | Gabbay |
| 7,318,998 B2 | 1/2008 | Goldstein et al. |
| 7,329,279 B2 | 2/2008 | Haug et al. |
| 7,331,993 B2 | 2/2008 | White |
| 7,354,702 B2 | 4/2008 | Dai et al. |
| RE40,404 E | 6/2008 | Schmitt et al. |
| 7,381,218 B2 | 6/2008 | Schreck |
| 7,381,219 B2 | 6/2008 | Salahieh et al. |
| 7,399,315 B2 | 7/2008 | Iobbi |
| 7,427,291 B2 | 9/2008 | Liddicoat et al. |
| 7,431,725 B2 | 10/2008 | Stack et al. |
| 7,468,073 B2 | 12/2008 | Johnson et al. |
| 7,473,237 B2 | 1/2009 | Navia et al. |
| 7,481,838 B2 | 1/2009 | Carpentier et al. |
| 7,503,929 B2 | 3/2009 | Johnson et al. |
| 7,510,571 B2 | 3/2009 | Spiridigliozzi et al. |
| 7,510,575 B2 | 3/2009 | Spenser et al. |
| 7,524,330 B2 | 4/2009 | Berreklouw |
| 7,556,646 B2 | 7/2009 | Yang et al. |
| 7,566,343 B2 | 7/2009 | Jenson et al. |
| 7,585,321 B2 | 9/2009 | Cribier |
| 7,604,661 B2 | 10/2009 | Pavcnik et al. |
| 7,618,446 B2 | 11/2009 | Andersen et al. |
| 7,622,276 B2 | 11/2009 | Cunanan et al. |
| 7,628,805 B2 | 12/2009 | Spenser et al. |
| 7,648,676 B2 | 1/2010 | Mills et al. |
| 7,670,368 B2 | 3/2010 | Hill et al. |
| 7,708,775 B2 | 5/2010 | Rowe et al. |
| 7,758,632 B2 | 7/2010 | Hojeibane et al. |
| 7,780,722 B2 | 8/2010 | Thielen et al. |
| 7,789,909 B2 | 9/2010 | Andersen et al. |
| 7,846,203 B2 | 12/2010 | Cribier |

(56) References Cited

U.S. PATENT DOCUMENTS

| | | |
|---|---|---|
| 7,846,204 B2 | 12/2010 | Letac et al. |
| 7,871,431 B2 | 1/2011 | Gurm et al. |
| 7,892,281 B2 | 2/2011 | Seguin et al. |
| 7,914,569 B2 | 3/2011 | Nguyen et al. |
| 7,914,576 B2 | 3/2011 | Navia et al. |
| RE42,395 E | 5/2011 | Wright et al. |
| 7,967,833 B2 | 6/2011 | Sterman et al. |
| 7,981,151 B2 | 7/2011 | Rowe |
| 7,993,394 B2 | 8/2011 | Hariton et al. |
| 8,002,825 B2 | 8/2011 | Letac et al. |
| 8,007,992 B2 | 8/2011 | Tian et al. |
| 8,052,750 B2 | 11/2011 | Tuval et al. |
| 8,057,540 B2 | 11/2011 | Letac et al. |
| 8,080,054 B2 | 12/2011 | Rowe |
| 8,105,375 B2 | 1/2012 | Navia et al. |
| 8,308,797 B2 | 11/2012 | Paniagua et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,512,401 B2 | 8/2013 | Murray, III et al. |
| 8,512,403 B2 | 8/2013 | Navia et al. |
| 8,568,475 B2 | 10/2013 | Nguyen et al. |
| 8,579,964 B2 | 11/2013 | Lane et al. |
| 8,628,566 B2 | 1/2014 | Eberhardt et al. |
| 8,790,398 B2 | 7/2014 | Paniagua et al. |
| 8,834,563 B2 | 9/2014 | Righini |
| 8,834,564 B2 | 9/2014 | Tuval et al. |
| 8,876,894 B2 | 11/2014 | Tuval et al. |
| 8,876,895 B2 | 11/2014 | Tuval et al. |
| 8,900,294 B2 | 12/2014 | Paniagua et al. |
| 9,119,716 B2 | 9/2015 | Lee et al. |
| 9,393,110 B2 | 7/2016 | Levi et al. |
| 9,504,564 B2 | 11/2016 | Nguyen et al. |
| 9,848,981 B2 | 12/2017 | Suri et al. |
| 2001/0010017 A1 | 7/2001 | Letac et al. |
| 2001/0023372 A1 | 9/2001 | Chen et al. |
| 2001/0044633 A1 | 11/2001 | Klint |
| 2001/0049558 A1 | 12/2001 | Liddicoat et al. |
| 2002/0005073 A1 | 1/2002 | Tompkins et al. |
| 2002/0028243 A1 | 3/2002 | Masters |
| 2002/0029783 A1 | 3/2002 | Stevens et al. |
| 2002/0032481 A1 | 3/2002 | Gabbay |
| 2002/0032482 A1 | 3/2002 | Cox |
| 2002/0037940 A1 | 3/2002 | Koob et al. |
| 2002/0042621 A1 | 4/2002 | Liddicoat et al. |
| 2002/0052651 A1 | 5/2002 | Myers et al. |
| 2002/0055772 A1 | 5/2002 | McGuckin et al. |
| 2002/0091441 A1 | 7/2002 | Guzik |
| 2002/0095167 A1 | 7/2002 | Liddicoat et al. |
| 2002/0095994 A1 | 7/2002 | Vesely et al. |
| 2002/0099439 A1 | 7/2002 | Schwartz et al. |
| 2002/0119437 A1 | 8/2002 | Grooms et al. |
| 2002/0123789 A1 | 9/2002 | Francis et al. |
| 2002/0123802 A1 | 9/2002 | Snyders |
| 2002/0128708 A1 | 9/2002 | Northrup et al. |
| 2002/0146393 A1 | 10/2002 | Bell et al. |
| 2002/0151970 A1 | 10/2002 | Garrison et al. |
| 2002/0198594 A1 | 12/2002 | Schreck |
| 2003/0027332 A1 | 2/2003 | Lafrance et al. |
| 2003/0078659 A1 | 4/2003 | Yang |
| 2003/0102000 A1 | 6/2003 | Stevens et al. |
| 2003/0118560 A1 | 6/2003 | Kelly et al. |
| 2003/0130727 A1 | 7/2003 | Drasler et al. |
| 2003/0130729 A1 | 7/2003 | Paniagua et al. |
| 2003/0130731 A1 | 7/2003 | Vidlund et al. |
| 2003/0138945 A1 | 7/2003 | McAllister et al. |
| 2003/0149477 A1 | 8/2003 | Gabbay |
| 2003/0153974 A1 | 8/2003 | Spenser et al. |
| 2003/0187362 A1 | 10/2003 | Murphy et al. |
| 2003/0195620 A1 | 10/2003 | Huynh et al. |
| 2003/0204023 A1 | 10/2003 | Koob et al. |
| 2003/0209835 A1 | 11/2003 | Chun et al. |
| 2003/0212460 A1 | 11/2003 | Darois et al. |
| 2003/0212462 A1 | 11/2003 | Gryska et al. |
| 2003/0217415 A1 | 11/2003 | Crouch et al. |
| 2004/0024452 A1 | 2/2004 | Kruse et al. |
| 2004/0039442 A1 | 2/2004 | St. Goar et al. |
| 2004/0049262 A1 | 3/2004 | Obermiller et al. |
| 2004/0055608 A1 | 3/2004 | Stevens et al. |
| 2004/0059418 A1 | 3/2004 | McKay et al. |
| 2004/0098092 A1 | 5/2004 | Butaric et al. |
| 2004/0158321 A1 | 8/2004 | Reuter et al. |
| 2004/0193261 A1 | 9/2004 | Berreklouw |
| 2004/0215333 A1 | 10/2004 | Duran et al. |
| 2004/0230285 A1 | 11/2004 | Gifford et al. |
| 2004/0243153 A1 | 12/2004 | Liddicoat et al. |
| 2004/0243229 A1 | 12/2004 | Vidlund et al. |
| 2005/0004668 A1 | 1/2005 | Aklog et al. |
| 2005/0027369 A1 | 2/2005 | Eldridge et al. |
| 2005/0043819 A1 | 2/2005 | Schmidt et al. |
| 2005/0096673 A1 | 5/2005 | Stack et al. |
| 2005/0113910 A1 | 5/2005 | Paniagua et al. |
| 2005/0137681 A1 | 6/2005 | Shoemaker et al. |
| 2005/0137682 A1 | 6/2005 | Justino |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159811 A1 | 7/2005 | Lane |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0187618 A1 | 8/2005 | Gabbay |
| 2005/0191248 A1 | 9/2005 | Hunter et al. |
| 2005/0228494 A1 | 10/2005 | Marquez |
| 2005/0241981 A1 | 11/2005 | Gupta et al. |
| 2005/0246035 A1 | 11/2005 | Wolfinbarger et al. |
| 2005/0247320 A1 | 11/2005 | Stack et al. |
| 2005/0267529 A1 | 12/2005 | Crockett et al. |
| 2006/0004439 A1 | 1/2006 | Spenser et al. |
| 2006/0004443 A1 | 1/2006 | Liddicoat et al. |
| 2006/0020336 A1 | 1/2006 | Liddicoat |
| 2006/0025800 A1 | 2/2006 | Suresh |
| 2006/0041306 A1 | 2/2006 | Vidlund et al. |
| 2006/0074486 A1 | 4/2006 | Liddicoat et al. |
| 2006/0089708 A1 | 4/2006 | Osse et al. |
| 2006/0111733 A1 | 5/2006 | Shriver |
| 2006/0129225 A1 | 6/2006 | Kopia et al. |
| 2006/0134079 A1 | 6/2006 | Sih et al. |
| 2006/0140916 A1 | 6/2006 | Siani-Rose et al. |
| 2006/0155366 A1 | 7/2006 | LaDuca et al. |
| 2006/0173475 A1 | 8/2006 | Lafontaine et al. |
| 2006/0178740 A1 | 8/2006 | Stacchino et al. |
| 2006/0190074 A1 | 8/2006 | Hill et al. |
| 2006/0193885 A1 | 8/2006 | Leonard Neethling et al. |
| 2006/0195010 A1 | 8/2006 | Arnal et al. |
| 2006/0195183 A1 | 8/2006 | Navia et al. |
| 2006/0206203 A1 | 9/2006 | Yang et al. |
| 2006/0212111 A1 | 9/2006 | Case et al. |
| 2006/0229701 A1 | 10/2006 | Gurm et al. |
| 2006/0229716 A1 | 10/2006 | Mitrev |
| 2006/0240063 A9 | 10/2006 | Hunter et al. |
| 2006/0240064 A9 | 10/2006 | Hunter et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265056 A1 | 11/2006 | Nguyen et al. |
| 2006/0287571 A1 | 12/2006 | Gozzi et al. |
| 2006/0292125 A1 | 12/2006 | Kellar et al. |
| 2007/0010857 A1 | 1/2007 | Sugimoto et al. |
| 2007/0043431 A1 | 2/2007 | Melsheimer |
| 2007/0050014 A1 | 3/2007 | Johnson |
| 2007/0050022 A1 | 3/2007 | Vidlund et al. |
| 2007/0056346 A1 | 3/2007 | Spenser et al. |
| 2007/0060932 A1 | 3/2007 | Stack et al. |
| 2007/0061008 A1 | 3/2007 | Salahieh et al. |
| 2007/0100426 A1 | 5/2007 | Rudakov et al. |
| 2007/0104395 A1 | 5/2007 | Kinigakis et al. |
| 2007/0128174 A1 | 6/2007 | Kleinsek et al. |
| 2007/0173861 A1 | 7/2007 | Strommer et al. |
| 2007/0203575 A1 | 8/2007 | Forster et al. |

(56) References Cited

U.S. PATENT DOCUMENTS

| | | |
|---|---|---|
| 2007/0213813 A1 | 9/2007 | Von Segesser et al. |
| 2007/0233228 A1 | 10/2007 | Eberhardt et al. |
| 2007/0250154 A1 | 10/2007 | Greenberg et al. |
| 2007/0263226 A1 | 11/2007 | Kurtz et al. |
| 2007/0276432 A1 | 11/2007 | Stack et al. |
| 2007/0276461 A1 | 11/2007 | Andreas et al. |
| 2008/0004686 A1 | 1/2008 | Hunt et al. |
| 2008/0009667 A1 | 1/2008 | Longhini et al. |
| 2008/0009940 A1 | 1/2008 | Cribier |
| 2008/0029105 A1 | 2/2008 | Stevens et al. |
| 2008/0039871 A1 | 2/2008 | Wallace et al. |
| 2008/0039926 A1 | 2/2008 | Majercak et al. |
| 2008/0058798 A1 | 3/2008 | Wallace et al. |
| 2008/0071361 A1 | 3/2008 | Tuval et al. |
| 2008/0082113 A1 | 4/2008 | Bishop et al. |
| 2008/0102439 A1 | 5/2008 | Tian et al. |
| 2008/0131522 A1 | 6/2008 | Liu et al. |
| 2008/0133004 A1 | 6/2008 | White |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0177381 A1 | 7/2008 | Navia et al. |
| 2008/0183280 A1 | 7/2008 | Agnew et al. |
| 2008/0183283 A1 | 7/2008 | Downing |
| 2008/0190989 A1 | 8/2008 | Crews et al. |
| 2008/0195200 A1 | 8/2008 | Vidlund et al. |
| 2008/0199843 A1 | 8/2008 | Haverich et al. |
| 2008/0200977 A1 | 8/2008 | Paul et al. |
| 2009/0005857 A1 | 1/2009 | Ischinger |
| 2009/0030511 A1 | 1/2009 | Paniagua et al. |
| 2009/0043383 A1 | 2/2009 | McGregor et al. |
| 2009/0054969 A1 | 2/2009 | Salahieh et al. |
| 2009/0054976 A1 | 2/2009 | Tuval et al. |
| 2009/0062907 A1 | 3/2009 | Quijano et al. |
| 2009/0112309 A1 | 4/2009 | Jaramillo et al. |
| 2009/0132032 A9 | 5/2009 | Cribier |
| 2009/0157175 A1 | 6/2009 | Benichou |
| 2009/0164005 A1 | 6/2009 | Dove et al. |
| 2009/0187241 A1 | 7/2009 | Melsheimer |
| 2009/0248149 A1 | 10/2009 | Gabbay |
| 2009/0254175 A1 | 10/2009 | Quijano et al. |
| 2009/0281609 A1 | 11/2009 | Benichou et al. |
| 2010/0030259 A1 | 2/2010 | Pavcnik et al. |
| 2010/0036479 A1 | 2/2010 | Hill et al. |
| 2010/0036484 A1 | 2/2010 | Hariton et al. |
| 2010/0043197 A1 | 2/2010 | Abbate et al. |
| 2010/0048987 A1 | 2/2010 | Khairkhahan |
| 2010/0049312 A1 | 2/2010 | Edoga et al. |
| 2010/0082094 A1 | 4/2010 | Quadri et al. |
| 2010/0131054 A1 | 5/2010 | Tuval et al. |
| 2010/0161036 A1 | 6/2010 | Pintor et al. |
| 2010/0185277 A1 | 7/2010 | Braido et al. |
| 2010/0217382 A1 | 8/2010 | Chau et al. |
| 2010/0234878 A1 | 9/2010 | Hruska et al. |
| 2010/0241069 A1 | 9/2010 | Hatten |
| 2010/0249918 A1 | 9/2010 | Zhang |
| 2010/0256749 A1 | 10/2010 | Tran et al. |
| 2010/0256751 A1 | 10/2010 | Rowe et al. |
| 2010/0312333 A1 | 12/2010 | Navia et al. |
| 2011/0004295 A1 | 1/2011 | Wittens |
| 2011/0004299 A1 | 1/2011 | Navia et al. |
| 2011/0015728 A1 | 1/2011 | Jimenez et al. |
| 2011/0040375 A1 | 2/2011 | Letac et al. |
| 2011/0087322 A1 | 4/2011 | Letac et al. |
| 2011/0137409 A1 | 6/2011 | Yang et al. |
| 2011/0146361 A1 | 6/2011 | Davidson et al. |
| 2011/0153009 A1 | 6/2011 | Navia et al. |
| 2011/0166636 A1 | 7/2011 | Rowe |
| 2011/0178597 A9 | 7/2011 | Navia et al. |
| 2011/0218619 A1 | 9/2011 | Benichou et al. |
| 2011/0224607 A1 | 9/2011 | Vogelbaum et al. |
| 2011/0240511 A1 | 10/2011 | Bolton et al. |
| 2011/0300625 A1 | 12/2011 | Paniagua et al. |
| 2011/0301700 A1 | 12/2011 | Fish et al. |
| 2012/0078343 A1 | 3/2012 | Fish |
| 2012/0078356 A1 | 3/2012 | Fish et al. |
| 2012/0095551 A1 | 4/2012 | Navia et al. |
| 2012/0158128 A1 | 6/2012 | Gautam et al. |
| 2012/0185038 A1 | 7/2012 | Fish et al. |
| 2012/0310041 A1 | 12/2012 | Paniagua et al. |
| 2013/0304201 A1 | 11/2013 | Navia et al. |
| 2014/0039613 A1 | 2/2014 | Navia et al. |

FOREIGN PATENT DOCUMENTS

| | | |
|---|---|---|
| EP | 2000115 | 5/2011 |
| EP | 1441672 | 9/2011 |
| EP | 2055266 | 2/2012 |
| EP | 1621162 | 5/2012 |
| EP | 2260796 | 2/2013 |
| EP | 2219558 B1 | 8/2015 |
| JP | 2007-516055 | 6/2007 |
| RU | 2355361 C | 5/2009 |
| WO | 1991/017720 | 11/1991 |
| WO | 1992/017118 | 10/1992 |
| WO | 1995/005207 | 2/1995 |
| WO | 1996/039997 | 12/1996 |
| WO | 1998/011935 | 3/1998 |
| WO | 1998/025549 | 6/1998 |
| WO | 1998/029057 | 7/1998 |
| WO | 1999/30646 | 6/1999 |
| WO | 2000/012164 | 3/2000 |
| WO | 2000/015147 A1 | 3/2000 |
| WO | 2000/047139 | 8/2000 |
| WO | 2001/002031 | 11/2001 |
| WO | 2003/047468 | 6/2003 |
| WO | 2003/092554 | 11/2003 |
| WO | 2004/026124 | 4/2004 |
| WO | 2004/082527 | 9/2004 |
| WO | 2006/095342 | 9/2006 |
| WO | 2007/033093 | 3/2007 |
| WO | 2007/047488 | 4/2007 |
| WO | 2007/138572 | 12/2007 |
| WO | 2008/028569 | 3/2008 |
| WO | 2008/063537 | 8/2008 |
| WO | 2008/106531 | 9/2008 |
| WO | 2009/052188 | 4/2009 |
| WO | 2009/149462 | 12/2009 |
| WO | 2009/156471 | 12/2009 |
| WO | 2010/011699 A2 | 1/2010 |
| WO | 2010/022138 | 2/2010 |
| WO | 2010/024801 | 3/2010 |
| WO | 2010/027363 | 3/2010 |
| WO | 2010/051025 | 5/2010 |
| WO | 2010/080594 | 7/2010 |
| WO | 2010/117541 | 10/2010 |
| WO | 2010/141847 | 12/2010 |
| WO | 2011/109433 | 3/2011 |
| WO | 2011/109450 | 9/2011 |
| WO | 2011/112706 | 9/2011 |
| WO | 2012/006124 | 1/2012 |
| WO | 2012/022138 | 2/2012 |
| WO | 2012/040643 | 3/2012 |
| WO | 2012/082952 | 6/2012 |

OTHER PUBLICATIONS

Examination Report dated Sep. 4, 2019, issued in Indian Application No. 5490/CHENP/2013 issued.

Bailey, "Percutaneous Expandable Prosthetic Valves", Textbook of Interventional Cardiology, W. B. Sauders Company, Second Ed., Chapter 75 (1994).

Edwards Lifesciences Corporation, "Edwards Receives European Approval for Advanced SAPIEN 3 Valve", News Release, Jan. 27, 2014, available at https://www.edwards.com/ns20140127.

Rösch, J. et al., "The Birth, Early Years, and Future of Interventional Radiology", J. Vasc. Interv. Radiol., 14:841-853 (2003).

CoreValve, "CoreValve Receives CE Mark Approval for its ReValvingTM System and Announces Plans to Initiate Expanded Clinical Evaluation", News Release, May 16, 2007.

(56) References Cited

OTHER PUBLICATIONS

Edwards Lifesciences Corporation, "Edwards Lifesciences Receives FDA Approval for First Catheter-Based Aortic Heart Valve in the U.S.", News Release, Nov. 2, 2011, available at https://www.edwards.com/ns20111102.
Pavcnik, D. et al., "Aortic and Venous Valve for Percutaneous Insertion", Min Invas Ther & Allied Technol, (2000): 9 (3/4) 287-292.
Medtronic Inc., "AneuRx(TM) Stent Graft System Instructions for Use", 1999 (41 pages).
Edwards Lifesciences Corporation, "Edwards SAPIEN XT Transcatheter Valve and Delivery Systems Receive CE Mark", News Release, Mar. 2, 2010, available at https://www.edwards.com/ns20100302.
Affidavit of Dr. Paolo Angelini, M.D., signed Aug. 25, 2009.
Affidavit of Dr. Gervasio A. Lamas, M.D., signed Sep. 3, 2009.
Declaration Under 37 CFR 1.131 as filed in U.S. Appl. No. 10/887,688 on Dec. 15, 2008, by co-inventors of that application.
Andersen, H.R. et al., "Transluminal implantation of artificial heart valve" European Heart Journal, 1992, 13, pp. 704-708.
"Artificial heart valve" http://en.wikipedia.org/Artificial_heart_valve, printed May 13, 2009.
Bonhoeffer, Philipp M.D. et al., "Percutaneous Insertion of the Pulmonary Valve" J of the Amer College of Cardiology, vol. 39, No. 10, Elsevier Science, Inc. 2002, pp. 1664-1669, London, UK, and Paris, FR.
Bonhoeffer, Philipp et al., "Percutaeous replacement of pulmonary valve in a right-centricle to pulmonary-artery prosthetic conduit with valve dysfunction" Early Report, The Lacet, vol. 356, Oct. 21, 2000, p. 1403-1405.
Bonhoeffer, Philipp et al., "Transcatherter Implantation of a Bovine Valve in Pulmonary Position: A Lamb Study" Circulation J. of the Amer Heart Assoc, 2000; 102; pp. 813-816.
Boudjemline, Younes et al., "Percutaneous pulmonary valve replacement in a large right ventricular outflow tract: An experimental study" J. Am. Coll. Cardiol. 2004; 43; pp. 1082-1087.
Braga-Vilela, A. et al., "Extracellular Matrix of Porcine Pericardium; Biochemistry and Collagen Architecture" J. Membr Biol., 2008.
Breuer, Christopher K. M.D. et al., "Application of Tissue-Engineering Principles toward the Development of a Semilunar Heart Valve Substitute" Tissue Engineering, vol. 10, No. 11/12, 2004, pp. 1725-1736.
Cale, A.R. et al., "Revisited: a descending thoracic aortic valve to treat prosthetic valve insufficiency" Ann Thorac Surg, May 1993, 55(5), pp. 1218-2.
Cerrolaza, M et al., "A comparison of the hydrodynamical behaviour of three heart aortic prostheses by numerical methods" Journal of Medical Engineering & Technology, vol. 20, No. 6, Nov./Dec. 1996, pp. 219-228.
Chew, G.G. et al., Abstract for "Simulation of Damage in a Porcine Prosthetic Heart Valve" J. Med. Eng. Technol., Sep.-Oct. 1999; 23(5): 178-89 (Abstract only).
Christie G.W. et al., Abstract for "On Stress Reduction in Bioprosthetic Heart Valve Leaflets by the Use of a Flexible Stent" J. Card Surg, Dec. 1991; 6(4) pp. 476-481 (Abstract only).
"Collagen" http://en.wikipedia.org/wiki/Collagen, printed May 13, 2009.
Collins, J. J., Jr, "The Evolution of artificial heart valve" N. Engl J Med, Feb. 28, 1991; vol. 324(9), pp. 624-626.
Corden, J. et al., "The influence of open leaflet geometry on the haemodynamic flow characteristics of polyrethane trileaflet artificial heart valve" Journal of Engineering in Medicine, 1996., vol. 210, pp. 273-287.
Cribier, Alain et al., "Percutaneious Transcatheter Implantation of an Aoritc Valve Prosthesis for Calcific Aortic Stenosis: First Human Case Description" Circulation J of the Amer Heart Assoc, originally published online Nov. 25, 2002.
Edwards Lifesciences Receives FDA Approval for New Heart Valve, http:www.medicalnewstoday.com/articles/149588.php, May 11, 2009.

Fish, R. David, "Percutaneous Heart Valve Replacement: Enthusiasm Tempered" Circulation J of the Amer Heart Assoc, 2004; vol. 110; pp. 1876-1878.
Fishbein, M.C. et al., "Cardiac pathology after aortic valve replacement using Hufnagel trileaflet prostheses: study of 20 necropsy patients" Ann Heart J., Apr. 1975, 89(4), pp. 443-448.
Gloeckner, D. Claire et al., "Mechanical Evaluation and Design of a Multilayered Collagenous Repair Biomaterial" J. of Biomedical Materials Research Part A, vol. 52 Iss 2, pp. 365-373, Published online Aug. 15, 2000, Wiley Periodicals, Inc.
Grube, et al., "Progress and Current Status of Percutaneous Aortic Valve Replacement: Results of Three Device Generations of the CoreValve Revalving System", Circ. Cardiovasc Intervent. 2008;1:167-175 (Abstract only).
Hanlon, JG et al., "Pre-use intraoperative testing of autologous tissue for valvular surgery: a proof of concept study" J. Heart Valve Dis, Nov. 1999; 8(6); pp. 614-623.
Bech-Hanssen, Odd, M.D. et al., "Aortic Prosthetic Valve Desing and Size: Relation to Doppler Echocardiographic Finding and Pressure Recovery—An In Vitro Study" J. Am Soc Echocardiography 2000; vol. 13, pp. 39-50.
Hasenkam, J.M. et al., "A model for acute haemodynamic studies in the ascending aorta in pigs" Cardiovasc Res, Jul. 1988, 22(7), pp. 464-471.
Hiester, E.D. et al., "Optimal bovine pericardial tissue selection sites. I. Fiber architecture and tissue thickness measurements." J. Biomed Mater Res, Feb. 1, 1998; 39(2), pp. 207-214.
Hilbert et al., "Biomechanics: Allograft Heart Valves," Cardiac Reconstructions with Allograft Tissues, Springer, New York (2005), pp. 210-212.
Hufnagel, Charles A., M.D., "Basic Concepts in the Development of Cardiovascular Prosthes" The American Journal of Surgery, vol. 137, Mar. 1979.
Hufnagel, Charles.A., MD et al., "In the beginning. Surgical Correction of Aortic Insufficiency" 1954; Ann Thorac Surg May 1989; 47(3), pp. 475-476.
Hufnagel, Charles.A., MD et al., "Late follow-up of ball-valve prostheses in the descending thoracic aortia", J. Throrac Cardovasc Surg, Dec. 1976, 72(6), pp. 900-909.
Hufnagel, Charles.A., MD et al., "Surgical Correction of Aortic Insufficiency" Surgery vol. 35, May 1954 No. 5.
Hufnagel, Charles A., "Vessels and Valves", Sec. 1: Development of Cardiac Surgery, 2nd ed., 1975, Chap 7, pp. 43-55.
Introduction to Stereomicroscopy, http://www.microscopyu.com/articles/stereomicroscopy/stereointro.html, Copyright 2000-2012, printed on Mar. 15, 2012.
Knudsen, LL et al., "Catheter-implanted prosthetic heart valves. Transluminal catheter implantation of a new expandable artificial heart valve in the descending thoracic aorta in isolated vessels and closed chest pigs" Int J. Artif Organs, May 1993, 16(5); pp. 253-262.
Lax, Jorge A., M.D., et al. "Estimation of the Ejection Fraction in Patients with Myocardial Infarction Obtained from the Combined Index of Systolic and Diastolic Left Ventricular Function: A New Method" J of the American Soc of Echocardiography, Feb. 2000, vol. 13, No. 2, pp. 116-123.
Liao, Jun et al., "Molecular orientation of collagen in intact planar connective tissues under biaxial stretch" Acta Biomateriala, vol. 1, Iss. 1, Jan. 2005, pp. 45-54.
Liao, K X et al., "Two-dimensional mechanical and ultrastructural correlates of bovine pericardium for prosthetic valves" ASAIO Trans, Jun. 1, 1991, 37(3); M341-51.
Yu, L.S., et al., "New Polyurethane valves in new soft artificial heart" ASAIO Trans Jul.-Sep. 1989; 35(3), pp. 301-304.
Mendelson, Karen et al., "Heart Valve Tissue Engineering: Concepts, Approaches, Progress, and Challenges" Ann Biomed Eng, Dec. 2006; 34(12); pp. 1799-1819; published online Oct. 12, 2006 doi:10.1007/s/10439-006-9163-z.
Mirnajafi, A. et al. "The effects of collagen fiber orientation of the flexural properties of pericardial heterograft biomaterials" Biomaterials, Mar. 2005, 26(7): pp. 795-804.
Mirzaie, M. et al., "A new storage solution for porcine aortic valves" Ann Thorac Cardiovasc Surg. Apr. 2007,13(2), pp. 102-109.

(56) References Cited

OTHER PUBLICATIONS

Moazami, N. et al., "Transluminal aortic valve placement. A feasibility study with a newly designed collapsible aortic valve" ASAIO J, Sep.-Oct. 1996, 42(5):M 381-5.

Nienaber C., M.D. et al., "Nonsurgical Reconstruction of Thoracic Aortic Dissection by Stent-Graft Placement" N. Eng. J. Med, May 20, 1999, col. 340, No. 20.

Noorlander, Maril L. et al., "A Quantitative Method to Determine the Orientation of Collagen Fibers in the Dermis" The J. of Histochemistry & Cytochemistry, vol. 50(11): 2002, pp. 1469-1474.

Nunn, D.B., "Structural Failure of Dacron Arterial Grafts" Seminars in Vascular Surgery, col. 12, No. 1 Mar. 1999, pp. 88-91.

Optical Microscope, Wikipedia, http://en.wikipedia.org/wild/Stereomiscroscope, May 13, 2009.

Orthogonality, http://en.wikipedia.org/wiki/Orthogonal, May 13, 2009.

Paniagua, David, et al., "Percutaneous Heart Valve in the Chronic In Vitro Testing Model, Circulation, 2002, pp. 51-52, vol. 106, American Heart Association, US.

Paniagua, David et al., First Human Case of Retrograde Transcatheter Implantation of an Aortic Valve Prosthesis, Texas Heart Institute Journal, 2005, pp. 91-96, vol. 32, US.

Paniagua, David et al., Abstract 4622: "Percutaneous Implantation of a Low Profile, Dry Membrane, Heart Valve in an Integrated Delivery System in the Aortic and Pulmonary Positions: One-month Animal Results," Circulation, American Heart Association, Inc., 2009; vol. 120: pp. 982.

Pathak, CP et al., "Treatment of bioprosthetic heart valve tissue with long chain alcohol solution to lower calcification potential" J Biomed Mater Res A. Apr. 1, 2004;69(1), pp. 140-144.

Pavenik, Susan, M.D., PhD et al., "Development and Initial Experimental Evaluation of a Prosthetic Aortic Valve for Transcatherter Placement" Cardivascular Radiology, Apr. 1992, pp. 151-154.

Pick, Adam, "True or False: An Edwards Lifesciences' Tissue Valve Replacement Requires 1,800 Hand-Sewn Stitches" http://heart-valve-surgery.com/heart-surgery-blog/2008/02/26. printed Aug. 13, 2010.

Pohl, M. et al., "In vitro testing of artificial heart valves; comparison between Newtonian and non-Newtonian fluids" Artif Argns, Jan. 1996; 20(1); pp. 37-46.

Purinya, B. et al., "Biomechanical and Structural Properties of the Explanted Bioprosthetic Valve Leaflets" J. of Biomechanis, vol. 27, Iss 1, Jan. 1994 pp. 1-11 Elsevier Science Ltd, 1993.

Sacks, M S et al., "Bioprosthetic heart valve heterograft biomaterials: structure, mechanical behavior and computational simulation" Expert Rev Med Devices, Nov. 2006; 3(6): pp. 817-834 (Abstract only).

Sacks, M S et al., "Collagen fiber architecture of bovine pericardium" ASAIO J, Jul. 1, 1994, 40(3), pp. 632-637.

Sacks, M S et al., "A small angle light scattering device for planar connective tissue miscrostructural analysis" Ann Biomed Eng, Jul. 1, 1997, 254(4), pp. 678-689.

Sacks, Michael S, "Incorporation of experimentally-derived fiber orientation into a structural constitutive model for planar collagenous tissues" J. Biomech Eng, Apr. 1, 2003, 125(2), pp. 280-287.

Sacks, Michael S. et al., "Orthotropic Mechanical Properties of Chemically Treated Bovine Pericardium" Annals of Biomedical Engineering, 1998, vol. 26, pp. 892-902.

Sacks, Michael S. et al., "Quantification of the fiber architecture and biaxial mechanical behavior of porcine intestinal submucosa" J of Biomedical Research, vol. 46, Iss 1, Jul. 1999, pp. 1-10.

Samouillan, V. et al., "Comparison of chemical treatments on the chain dynamics and thermal stability of bovine pericardium collagen" J Biomed Mater Res A. Feb. 1, 2003;64(2), pp. 330-338.

Schmidt, Dorthe et al., "Tissue engineering of heart valves using decellularized xenogeneic of polymeric starter matrices" Philos Trans R Soc Lond B Bio Sci., Aug. 29, 2007, 362(1484); 1505-1512; published online Jun. 22, 2007, doi: 10.1098/rstb.2007.2131.

Schoen, Frederick J., "Tissue heart valves: Current challenges and future research perspectives" J of Biomedical Materials Research, vol. 47, Iss 4, Dec. 15, 1999, pp. 439-465.

Sellaro, Tiffany L., "Effects of Collagen Orientation on the Medium-Term Fatigue Response of Heart Valve Biomaterials" 2003, (published thesis) pp. 40-45.

Sellaro, Tiffany L. et al., "Effects of Collagen Fiber Orientation on the Response of Biologically Derived Soft Tissue Biomaterials to Cyclic Loading" J. Biomed Mater Res A, Jan. 1, 2007; 80(1): 194-205); published online Oct. 13, 2006 by Wiley InterScience.

Shandas, Robin PhD et al., "A Method for Determining the Reference Effective Flow Areas for Mechanical Heart Valve Prostheses" Circulation Apr. 25, 2000.

Shen, Ming et al., "Effect of ethanol and ether in the prevention of calcification of bioprostheses" Ann Thorac Surg. May 2001;71(5 Suppl), pp. 413-416.

Shen, Ming et al., "Protein adsorption in glutaraldehyde-preserved bovine pericardium and porcine valve tissues" The Annals of Thoracic Surgery, 2001; 71, pp. 409.

Simionescu, D et al., "Mapping of glutaraldehyde-treated bovine pericardium and tissue selection for bioprosthetic heart valve" J. Biomed Mater Res, Jun. 1, 1993:27(6), pp. 697-704.

Sun, Wei et al., "Response of heterograft heart valve biomaterials to moderate cyclic loading" J Biomed Mater Res A, Jun. 2004, 69(4), pp. 658-669.

Topol, Eric J., "Textbook of Interventional Cardiology", 1990, Chs. 43-44, pp. 831-867.

Vyavahare, Narendra et al., "Mechanisms of bioprosthetic heart valve failure: Fatigue causes collagen denaturation and glycosaminoglysan loss" J of Biomedical Research, vol. 446, Iss 1, Jul. 1999, pp. 44-50.

Vyavahare, NR et al., "Prevention of Glutaraldehyde-Fixed Bioprosthetic Heart Valve Calcification by Alcohol Pretreatment: Further Mechanistic Studies" J Heart Valve Dis. Jul. 2000;9(4), pp. 561-566.

Werner, S. et al., "Testing the Hydrodynamic properties of heart valve prostheses with a new test apparatus", Biomed Tech (Bert) Sep. 1994; 30(9); pp. 204-210 (Abstract only).

Wiegner, A W et al., "Mechanical and structural correlates of canine pericardium" Circ Res, Sep. 1, 1981m 49(3), pp. 807-814.

Yasui, Takeshi et al., "Determination of collagen fiber orientation in human tissue by use of polarization measurement of molecular second-harmonic-generation light", Applied Optics, vol. 42, No. 14, May 10, 2004, pp. 2861-2867.

Zioupos, P. et al., "Anisotropic Elasticity and Strength of Glutaraldehyde Fixed Bovine Pericardium for Use in Pericardial Bioprosthetic Valves" J. Biomed Mater Res., Jan. 1994, 28(1), pp. 49-57.

Zioupos, P. et al., "Mechanical and Optical anisotrophy of bovine pericardium" Med Biol Eng Comput, Jan. 1992; 30(1); pp. 76-82.

PCT International Search Report and Written Opinion, in Application PCT/US2011/064989, dated Jun. 28, 2013.

PCT International Report on Patentability in Application No. PCT/US2011/064989, dated Jun. 27, 2013.

Extended European Search Report in EP Application No. 11848038. 3, dated Oct. 25, 2017.

Examination Report in Australian Application No. 2011343755, dated May 13, 2014.

Second Examination Report in Australian Application No. 2011343755, dated Aug. 29, 2014.

Office Action in Chinese Application No. 201180067413.6, dated Jan. 21, 2015.

Office Action issued in Japanese Application No. 2013-544758, dated Nov. 4, 2015.

Information about Related Patents and Patent Applications, see section 6 of the accompanying Information Disclosure Statement Letter, which concerns Related Patents and Patent Applications.

Examination Report dated Apr. 18, 2018, issued in Australian Application No. 2017200883.

Notice of Acceptance dated Mar. 14, 2019, issued in Australian Application No. 2017200883.

Office Action dated Apr. 2, 2019, issued in Japanese Patent Application No. 2017-254194 (Engtlish translation provided).

LEGEND

| | |
|---|---|
| ——— | Visible free (cut) edge of membrane piece |
| ——— | Visible edge of folded structure |
| ·········· | Line of fold / crease |
| ------------ | Hidden (phantom) edges of folded structure |
| ▬ ▬ ▬ ▬ | Line of cut |

LEGEND
| | |
|---|---|
| ▬▬▬ | Visible free (cut) edge of membrane piece |
| ——— | Visible edge of folded structure |
| ·········· | Line of fold / crease |
| ------------ | Hidden (phantom) edges of folded structure |
| − − − − − | Line of cut |

LEGEND
| | |
|---|---|
| ▬▬▬▬ | Visible free (cut) edge of membrane piece |
| ─────── | Visible edge of folded structure |
| ············ | Line of fold / crease |
| ------------ | Hidden (phantom) edges of folded structure |
| ▬ ▬ ▬ ▬ | Line of cut |

LEGEND

| | |
|---|---|
| ⎯⎯⎯ | Visible free (cut) edge of membrane piece |
| ——— | Visible edge of folded structure |
| ············ | Line of fold / crease |
| ------------- | Hidden (phantom) edges of folded structure |
| - - - - - | Line of cut |

*Figure 1G*  Suture attachments omitted for clarity.
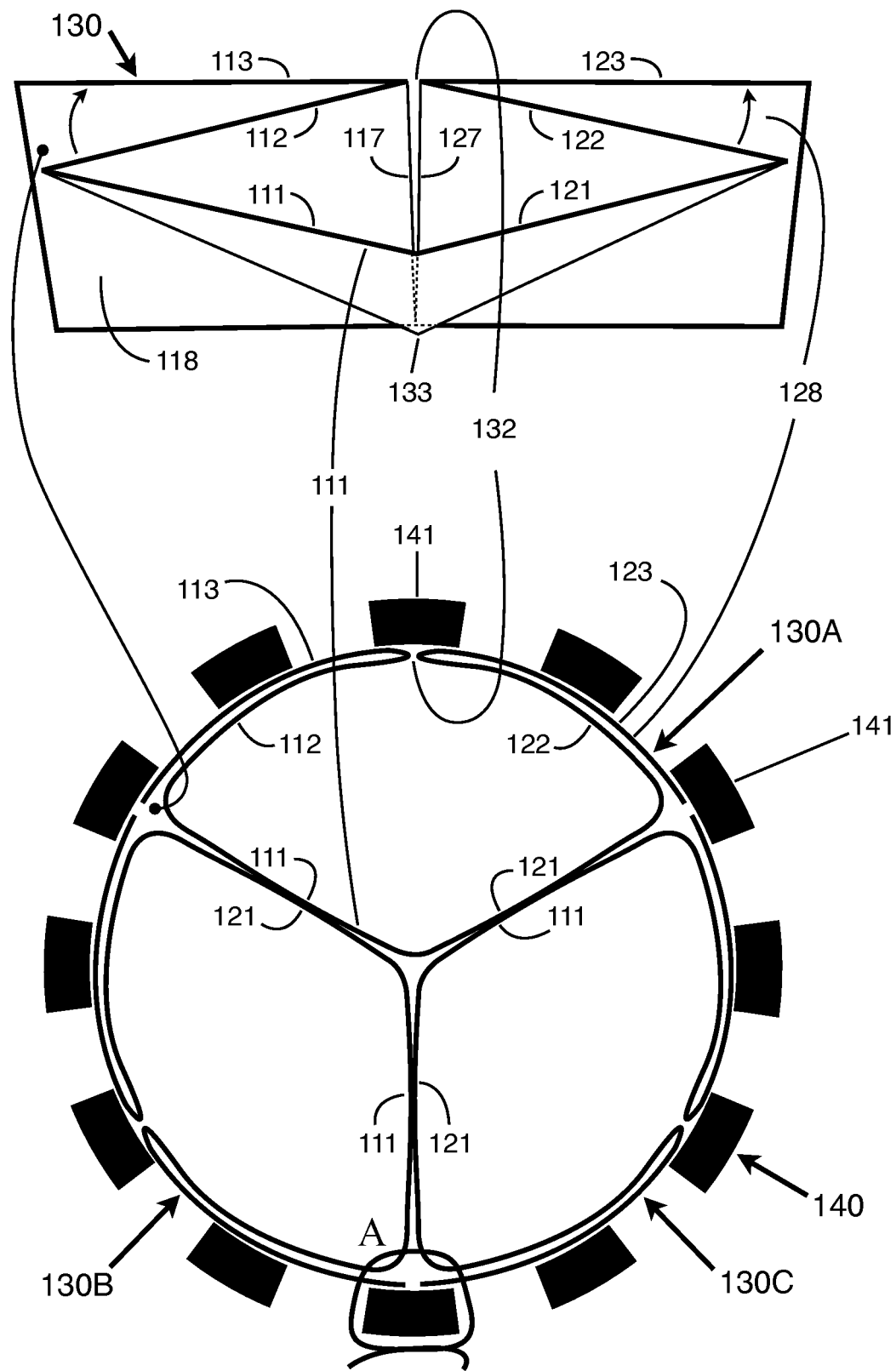

LEGEND
| | |
|---|---|
| ——————— | Visible free (cut) edge of membrane piece |
| ——— | Visible edge of folded structure |
| ············ | Line of fold / crease |
| ------------ | Hidden (phantom) edges of folded structure |
| ▬ ▬ ▬ ▬ ▬ | Line of cut |

LEGEND
— Visible free (cut) edge of membrane piece
— Visible edge of folded structure
........... Line of fold / crease
------------ Hidden (phantom) edges of folded structure
- - - - - - Line of cut

LEGEND

| | |
|---|---|
| ——— | Visible free (cut) edge of membrane piece |
| ——— | Visible edge of folded structure |
| ·········· | Line of fold / crease |
| ----------- | Hidden (phantom) edges of folded structure |
| ▬ ▬ ▬ ▬ | Line of cut |

LEGEND
━━━━ Visible free (cut) edge of membrane piece
──── Visible edge of folded structure
· · · · · · Line of fold / crease
- - - - - Hidden (phantom) edges of folded structure
▬ ▬ ▬ ▬ Line of cut LEGEND
| | |
|---|---|
| ▬▬▬▬ | Visible free (cut) edge of membrane piece |
| ——— | Visible edge of folded structure |
| ·········· | Line of fold / crease |
| ---------- | Hidden (phantom) edges of folded structure |
| – – – – – | Line of cut |

LEGEND
— Visible free (cut) edge of membrane piece
— Visible edge of folded structure
......... Line of fold / crease
--------- Hidden (phantom) edges of folded structure
- - - - - - Line of cut LEGEND
━━━━ Visible free (cut) edge of membrane piece
──── Visible edge of folded structure
·········· Line of fold / crease
------- Hidden (phantom) edges of folded structure
- - - - - Line of cut LEGEND
| | |
|---|---|
| ▬▬▬▬▬ | Visible free (cut) edge of membrane piece |
| ──────── | Visible edge of folded structure |
| ············ | Line of fold / crease |
| ------------ | Hidden (phantom) edges of folded structure |
| ▬ ▬ ▬ ▬ ▬ | Line of cut |

LEGEND

| | |
|---|---|
| —————— | Visible free (cut) edge of membrane piece |
| ——— | Visible edge of folded structure |
| ············ | Line of fold / crease |
| ------------ | Hidden (phantom) edges of folded structure |
| — — — — — | Line of cut |

LEGEND
| | |
|---|---|
| —————— | Visible free (cut) edge of membrane piece |
| ——— | Visible edge of folded structure |
| ············ | Line of fold / crease |
| ------------ | Hidden (phantom) edges of folded structure |
| ▬ ▬ ▬ ▬ | Line of cut |

Suture attachments omitted for clarity

Suture attachments omitted for clarity

PERCUTANEOUSLY DELIVERABLE HEART VALVE INCLUDING FOLDED MEMBRANE CUSPS WITH INTEGRAL LEAFLETS

CROSS-REFERENCE TO RELATED APPLICATION

The present application claims the benefit of U.S. Provisional Patent Application No. 61/423,051 filed on Dec. 14, 2010, the content of which is incorporated herein by reference in its entirety.

FIELD

The present invention relates to the field of medical devices, and more particularly, to percutaneously deliverable heart valves.

BACKGROUND

The native heart valves, and in particular, the aortic valve, has a complex geometry that endows both ideal opening and closing geometries through an anatomic joining of a tubular inflow structure of the left ventricular outflow tract and an expansion of the valve sinuses above the hinging point of the valve leaflets defined by the aortic valve annular ring, part of the fibrous "skeleton" of the heart.

For the purposes of discussion and definition in the ensuing descriptions, the "upper", downstream outlet structure of the native aortic valve above its hinging point contains three valve "cusps" of a generally spherical contour with central mobile portions termed "leaflets" that are induced by fluid pressure gradients to meet centrally to close and to move radially outward to open in valve operation. The cusps are further continuous with downstream curved tissue walls meeting the tubular great vessel, the aorta, at the "sino-tubular junction". Each cusp and its upper, downstream extension above the level of leaflet closure ("coaptation") are a continuous structure of a generally spherical contour and together define the envelope of the "sinus of Valsalva. Typically, surgical prosthetic valves are implanted by excision of the diseased native valve leaflets at the level of the annular ring, and suturing of the prosthetic valve at this point, thus replacing only the opening geometry of the valve and leaving the outer structures of the cusps and the sinuses of Valsalva, the anatomy that confers proper closing geometry, generally intact.

Surgical valve prostheses are generally constructed as analogs to this central portion of the native valve geometry involved in the opening phase of the valve cycle. This approach to modeling the replacement valve prosthesis is enabled by the nature of the surgical technique: the replacement valve is sutured into the valve seat under direct vision. In contrast, a percutaneous stent-mounted heart valve ("PHV") is typically a construct in which the operating valve membrane leaflets are mounted and confined within the tubular envelope of a collapsible frame for effective transvascular delivery.

Further, in order to preclude valve regurgitation, the base of each leaflet must lie in exact apposition to the valve seat to form a seal, a condition that is difficult to satisfy without implantation under direct vision. Even then, since the diseased native valve would not be removed and its axial geometry is often distorted, it may not be possible to seat a PHV exactly under any circumstances. Thus, a cylindrical cuff layer, interior or exterior to the frame, is usually employed that acts as a seal and provides some latitude in the positioning and alignment of the PHV along the axis of flow, allowing for reliable and effective PHV implantation and minimizing the risk of significant valve regurgitation. Finally, the diseased native valve leaflets, when pushed outward by the deployed PHV frame, may themselves form a barrier separating the sinuses of Valsalva from the leaflets of the PHV, then disrupting the native closing geometry of the valve so that the sinuses are no longer continuous with the pressurized space above the PHV leaflets.

These issues illustrate some of the challenges to the formation of a PHV; that is, how to confine operating leaflets within a partially sealed tubular structure while preserving ideal opening and closing valve behavior without the benefit of the natural mechanism of the sinuses of Valsalva in a single valve and leaflet geometry, such as the separate and distinct upper and lower geometries of the native valve. As such, there is a need for additional devices, systems and/or methods that address one or more of the problems or shortcomings noted above.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

Two goals of at least some embodiments of the present inventions are: (1) to maximize effective orifice area and minimize opening pressure gradients through geometry that mimics the natural form of inflow into the valve—the tubular outflow tract of the heart pumping chamber; and (2) to minimize the inward tension on the leaflet commissures in the closed position through geometry that mimics the natural effect of the sinuses of Valsalva—an effect that prevents downward displacement of the leaflet free edges under closing pressure, thus distributing force along the lines of leaflet apposition rather than focusing it at the points of leaflet attachment to the frame.

The first of these goals dictates that the inflow to the valve, similar to that of the natural aortic valve, encounters then outwardly displaces the most central portion of the leaflets first, with opening moving progressively outward along the surface of the leaflets. The second suggests that the cross-sectional profile of the valve sinus/cusp formed in its central portion by the free edge of the leaflets, like that of the natural aortic valve, should be approximately elliptical, and that the cross-sectional diameter of each cusp should progressively decrease below the plane of leaflet apposition, like that of the natural valve cusps. One or more embodiments of the one or more present inventions answer the configuration ideals with a robust balance of functional geometries for valve opening and closing.

The spherical geometry of the native aortic valve leaflets is difficult to replicate in a transcatheter valve. First, while this shape is functionally robust in vivo, even if reproduced in some form it is not suited to efficient radial compression typically required for collapse into a small diameter delivery catheter used in transcatheter valve delivery systems, and discontinuities would develop in the leaflet surface that would resolve into irregular folds with at least some circumferential component, thereby threatening the restitution of the geometry on reopening at deployment. Second, tissue bioprosthetic valve leaflets, if not actually constituted of the animal valve itself, are typically constructed of flat sheet tissue membrane from which rendering of cusps with leaflets of a spherical contour would be difficult if not impossible without the use of traction force on the material, or extensive cutting and suturing of the leaflet cusp portion—an impractical approach, and a threat to the material integrity of the thin tissue membrane.

At least one embodiment of the one or more present inventions answers these challenges by employing conical rather than spherical cusp geometry, thereby reproducing some benefits of the latter with near-elliptical leaflet cross-section that progressively decreases moving proximal to the plane of leaflet apposition while being readily conformed on outward radial compression in the valve opening phase into a substantially flat folded construct against the interior tubular walls of the containing frame. This favorable resolution of the conical geometry in opening phase expresses the opening efficiency of this valve design with a large effective orifice area and low transvalvular energy losses. In the closed position, the free edges of the separate leaflets of the conical cusps meet in apposition, each cone acting as an independent valve; pressure load-bearing is enhanced by the material continuity of the cone structure with the inner apposing wall and outer wall of each cone being part of a single continuous membrane structure. Further, the conical cusps are particularly suited for compression and containment within a collapsible frame for transcatheter delivery.

In at least one embodiment, a transcatheter, percutaneously implantable, bioprosthetic heart valve having a lattice frame comprising a substantially tubular alloy metal mesh, and two or more valve cusps with leaflets mounted to the lattice frame, is provided. Further, the cusps include a flat sheet of processed mammalian tissue membrane that is folded into a substantially conical shape according to a flat folding pattern, the substantially conical shape is further formed by joining opposing sides of the substantially conical shape along a seam that is oriented along a longitudinal axis of the substantially conical shape. In at least one embodiment, the two or more cusps are attached along their seams (which may or may not include the apexes of the cusps), such as, by way of example and not limitation, along the axial centerline of the outer circumference of the cone, to an interior portion of the lattice frame along an axial flow direction of the valve and are further attached along the distal, downstream, edge of the substantially conical shape along at least an outer half of the substantially conical shape's edge. When the membrane valve leaflet is attached to the frame, its principal line of securement along the axial centerline of the outer circumference of the cone is attached at a non-commissural seam or edge, effecting a coaxial (to the flow axis) line of attachment at an area of the structure that advantageously bears load, thereby relieving the commissural attachment of loads associated with the securement of the cusp structures to the frame. As such, the leaflet commissure attachments, thus located at points where the leaflet membrane is continuous and uncut, advantageously need only bear the centripetal loads associated with the radially inward movement and operation of the free edges of the leaflets.

In at least one embodiment, a transcatheter, percutaneously implantable, bioprosthetic heart valve is provided wherein two distal, downstream, vertices of the flattened cusp and leaflet structure are folded over in a radially outward direction and fixed to the frame such that the vertex folds of neighboring leaflets are adjacent and define an extent of leaflet apposition at the points corresponding to leaflet commissures.

In at least one embodiment, a transcatheter, percutaneously implantable, bioprosthetic heart valve is provided wherein a vertex forming a proximal, upstream, apex of the substantially conical shape is folded over in a radially outward direction and affixed to an inner portion of the frame.

In at least one embodiment, a transcatheter, percutaneously implantable, bioprosthetic heart valve is provided wherein the flat folding pattern is polygonal and includes extending portions that, when the leaflet is mounted, extend circumferentially outward from an axial line of attachment of the leaflet to the frame so as to form, when joined and attached to corresponding extending portions of neighboring leaflets, an integral, inner, luminal, circumferentially partial or complete sealing cuff.

In at least one embodiment, a transcatheter, percutaneously implantable, bioprosthetic heart valve is provided wherein a separate tubular sealing cuff of tissue membrane is attached to an outer, abluminal surface of the frame to form a sealing cuff. In at least one embodiment, the membrane sheet is a single layer of a substantially homogenous material. In at least one embodiment, the membrane sheet is an unlaminated single layer of material. In at least one embodiment, the membrane sheet is a single layer of material that does not include any reinforcement, such as reinforcing fibers. In at least one embodiment, the membrane sheet is a single layer of treated pericardium tissue. In at least one embodiment, the membrane sheet is a single layer of a synthetic film.

Therefore, in accordance with at least one embodiment, a transcatheter, percutaneously implantable, prosthetic heart valve is provided, comprising:

a lattice frame; and two or more integrated cusp and leaflet folded structures attached to the lattice frame, the two or more integrated cusp and leaflet folded structures each comprising a flat sheet of biocompatible membrane that is folded to include a mobile leaflet layer and a cusp wall layer, wherein the cusp wall layer located radially outside of the mobile leaflet layer, and wherein the cusp wall layer is further formed by joining apposing sides of the cusp wall layer along a seam. In accordance with at least one embodiment, the two or more integrated cusp and leaflet folded structures are each attached along their respective seams to the lattice frame. In accordance with at least one embodiment, the seams are oriented in a direction substantially parallel to an axis of the lattice frame. In accordance with at least one embodiment, the flat sheet of biocompatible membrane forming at least one integrated cusp and leaflet folded structure of the two or more integrated cusp and leaflet folded structures comprises two or more pieces of biocompatible membrane material.

In accordance with at least one embodiment, a transcatheter, percutaneously implantable, prosthetic heart valve is provided, comprising:

a lattice frame; and two or more integrated cusp and leaflet folded structures attached to the lattice frame, the two or more integrated cusp and leaflet folded structures each comprising a flat sheet of a biocompatible membrane that is folded to include a valve cusp according to a flat folding pattern, wherein the valve cusp is further formed by joining apposing sides of the valve cusp along a seam, and wherein the two or more integrated cusp and leaflet folded structures are each attached along their respective seams to the lattice frame in a direction substantially parallel to an axis of the lattice frame. In accordance with at least one embodiment, two distal, downstream, vertices of the integrated cusp and leaflet folded structure are folded over as vertex folds in a radially outward direction and fixed to the lattice frame such that the vertex folds of circumferentially adjacent leaflets are adjacent and define a degree of leaflet apposition at the points corresponding to leaflet commissures. In accordance with at least one embodiment, the two distal, downstream, vertices are fixed to the lattice frame by attachment not along an alignment with the vertex folds. In accordance with at least one embodiment, a vertex forming a proximal, upstream, tip of the substantially conical shape is folded over in a radially outward direction and attached to an inner portion of the lattice frame. In accordance with at least one embodiment, the flat folding pattern is polygonal and includes extending portions that, when the cusp is mounted, extend circumferentially outward from an axial line of attachment of the cusp to the frame so as to form, when joined and attached to corresponding extending portions of neighboring cusps, an integral, inner, luminal, circumferentially complete sealing cuff. In accordance with at least one embodiment, the flat folding pattern is polygonal and includes extending portions that, when the two or more cusps are mounted, extend circumferentially outward from an axial line of attachment of the cusp to the lattice frame so as to form a circumferentially incomplete sealing cuff portion associated with each cusp. In accordance with at least one embodiment, a separate tubular sealing cuff of biocompatible membrane is attached to an outer, abluminal surface of the lattice frame to form a sealing cuff. In accordance with at least one embodiment, the lattice frame is collapsible and expandable and comprises a metal alloy substantially configured as tubular stent member. In accordance with at least one embodiment, the biocompatible membrane comprises processed mammalian pericardium tissue. In accordance with at least one embodiment, the biocompatible membrane does not comprise a treated tissue. In accordance with at least one embodiment, the biocompatible membrane comprises a synthetic material. In accordance with at least one embodiment, the seams of the two or more integrated cusp and leaflet folded structures are each oriented along an axis of flow of the valve. In accordance with at least one embodiment, the two or more integrated cusp and leaflet folded structures are each further attached to a circumferential portion of the lattice frame along at least a portion of their distal downstream edges. In accordance with at least one embodiment, the two or more integrated cusp and leaflet folded structures are attached to the lattice frame at least at a non-commissural seam aligned with an axial flow direction of the valve.

In accordance with at least one embodiment, a transcatheter, percutaneously implantable, prosthetic heart valve is provided, comprising:

a lattice frame; and two or more integrated cusp and leaflet structures attached to the lattice frame, the two or more integrated cusp and leaflet structures each comprising a flat sheet of biocompatible membrane that is folded to include a mobile leaflet layer and a cusp wall layer, wherein with the mobile leaflet layer in a closed position a transverse cross-sectional area of a cusp-sinus space decreases monotonically from a distal end to a proximal end of the mobile leaflet layer. In accordance with at least one embodiment, the cusp wall layer is located radially outside of the mobile leaflet layer. In accordance with at least one embodiment, the cusp wall layer is further formed by joining apposing sides of the cusp wall layer along a seam. In accordance with at least one embodiment, the mobile leaflet layer in the closed position a transverse cross-sectional length of the mobile leaflet layer decreases monotonically from a distal end to a proximal end of the mobile leaflet layer. In accordance with at least one embodiment, the mobile leaflet layer and the cusp wall layer of each integrated cusp and leaflet structure are a single continuous piece of biocompatible membrane.

At least one invention of the one or more present inventions is a novel integrated cusp and leaflet structure that has application for a variety uses, including implantable valves other than prosthetic heart valves. Accordingly, in at least one embodiment, and in subcombination, an integrated cusp and leaflet structure for attachment to a lattice frame to form a valve configured for implantation in a vascular system of a patient is provided, the integrated cusp and leaflet structure comprising:

a flat sheet of biocompatible membrane that is folded to include a mobile leaflet layer and a cusp wall layer, wherein the cusp wall layer is divided along a seam, and wherein the mobile leaflet layer is continuous and apposes the cusp wall layer when the integrated cusp and leaflet structure is pressed substantially flat. In accordance with at least one embodiment, the mobile leaflet layer and the cusp wall layer of the integrated cusp and leaflet structure are a single continuous piece of biocompatible membrane. In accordance with at least one embodiment, the biocompatible membrane comprises a synthetic material. In accordance with at least one embodiment, the integrated cusp and leaflet structure further comprises at least one commissure tab. In accordance with at least one embodiment, the at least one commissure tab is configured for engaging a slot within a member of the lattice frame.

One or more embodiments of the one or more present inventions are also directed to methods for forming the inventive valves described herein, as well as its component elements. Accordingly, a method of forming an integrated cusp and leaflet folded structure for use in an implantable valve having an axial flow direction is provided, comprising: folding a flat sheet of biocompatible membrane to form an integrated cusp and leaflet folded structure according to a flat folding pattern, wherein said folding includes making two diagonal folds in the flat sheet of biocompatible membrane, the two diagonal folds separating a mobile leaflet layer from a cusp wall layer of the integrated cusp and leaflet folded structure. In accordance with at least one embodiment, the two diagonal folds are angled at between about 10 to 80 degrees from the axial flow direction. In accordance with at least one embodiment, the method further comprises forming first and second cusp wall folds, wherein the cusp wall layer is further formed by joining apposing membrane portions adjacent the first and second cusp wall folds along a seam that is oriented substantially parallel with the axial flow direction.

In addition to the foregoing, in accordance with at least one embodiment, a method of forming a transcatheter, percutaneously implantable, prosthetic heart valve is provided, comprising: folding a plurality of integrated cusp and leaflet folded structures, each integrated cusp and leaflet folded structure of the plurality of integrated cusp and leaflet folded structures comprising a flat sheet of biocompatible membrane that is folded to form a cusp according to a flat folding pattern, wherein the cusp is further formed by joining apposing sides of the cusp along a seam; and attaching each integrated cusp and leaflet folded structure of the plurality of integrated cusp and leaflet folded structures to a lattice frame, wherein the two or more integrated cusp and leaflet folded structures are each attached along their respective seams to the lattice frame in a direction substantially parallel to an axis of the lattice frame.

Various components are referred to herein as "operably associated." As used herein, "operably associated" refers to components that are linked together in operable fashion, and encompasses embodiments in which components are linked directly, as well as embodiments in which additional components are placed between the two linked components.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, a more particular description of the one or more present inventions is rendered by reference to specific embodiments thereof which are illustrated in the appended drawings. It should be appreciated that these drawings depict only typical embodiments of the one or more present inventions and are therefore not to be considered limiting of its scope. The one or more present inventions are described and explained with additional specificity and detail through the use of the accompanying drawings in which:

FIG. 1G is same structure and view shown in FIG. 1E, along with a top (distal) cross-section schematic view of the distal end of a three-leaflet valve in a closed operating position;

Figure 1A:
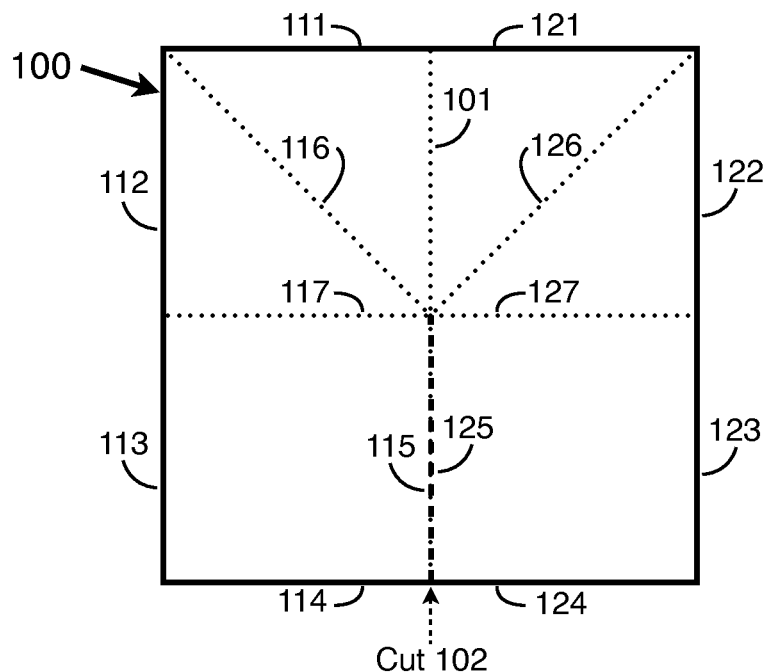
FIG. 1A is a plan view of a flat sheet membrane template for the formation of an integrated cusp and leaflet folded structure in accordance with at least one embodiment of the one or more present inventions.

The drawings are not necessarily to scale.

DETAILED DESCRIPTION

One or more embodiments of the one or more inventions described herein include an implantable prosthetic heart valve having a frame and two or more cusp and leaflet structures mounted to the frame. The frame preferably comprises a lattice of substantially tubular alloy metal mesh. The cusp and leaflet structures include a membrane operable to open and close, thereby providing a functioning valve when mounted within a frame. In at least one embodiment, the membrane preferably comprises a flat sheet of processed mammalian tissue membrane that is folded into a substantially conical shape according to a flat folding pattern.

In the ensuing descriptions and referenced figures it will be seen that, when applied to a dry sheet membrane, the folding initially results in a cusp shape of an inverted pyramid with a rhomboid base. On relaxation of the folds as occurs naturally with a flexible and pliable membrane, especially when the membrane is hydrated, the cusp shape becomes substantially conical in shape and will be described as such in the ensuing descriptions as it more closely represents the embodiment of the cusp in operation of the valve.

Formation of a valve construct as described herein provides a percutaneously deliverable heart valve with a relatively small diameter for transcatheter placement. That is, the substantially conical shape associated with the flat folding patterns used to form leaflets as described herein allow for construction of a valve that can be compressed prior to introduction to a catheter to an advantageously small diameter, thereby facilitating transcatheter percutaneous delivery of the valve within a patient. The substantially conical shape is further formed by joining two axially oriented sides of the substantially conical shape along a seam that is oriented along a longitudinal axis of the substantially conical shape. The two or more integrated cusp and leaflet structures are affixed to an interior portion of the lattice frame along an axial flow direction of the valve and are further affixed along the distal, downstream, edge of the substantially conical shape along at least an outer half of the substantially conical shape's edge.

One or more of the various embodiments described herein have a number of different features and characteristics as compared to other commercially available prosthetic heart valves. For example, at least one embodiment of a transcatheter, percutaneously implantable, prosthetic heart valve described below comprises a flat polygonal sheet membrane having more than four sides and which forms an integrated cusp and leaflet structure.

In addition, at least one embodiment of a transcatheter, percutaneously implantable, prosthetic heart valve described below comprises integrated cusp and leaflet structures that are attached to a lattice frame at the circumferential perimeter locations corresponding to the commissures. At such locations, the length of the seam that forms the common line of attachment of the cusp and integral leaflet to the frame is less than one-half to two-thirds of the axial length of the membrane portion of the valve.

In at least one embodiment of a transcatheter, percutaneously implantable, prosthetic heart valve, when the valve is in the open position, the mobile leaflet layer apposes or is geometrically free to appose its full outward surface completely to the immediately radially located outward structure, such as at least one of the cusp wall layer or interior surface of the lattice frame. In at least one embodiment, in the closed position the transverse cross-sectional length of the mobile leaflet layer and the cross-sectional area of the cusp/sinus space decreases monotonically from the distal end to proximal end of the membrane portion of the valve. (That is, generally the property of a cone as well as an inverted pyramid.)

In at least one embodiment, the mobile leaflet layer and the immediately outward structure for the full axial length of the leaflet (cusp wall layer, frame, or other) are a single continuous piece of material.

In at least one embodiment, at the base of each cusp (that is, at the most proximal extent of the leaflet), the circumferential extent of attachment of the membrane to the frame is less than the circumferential extent of attachment of the membrane to the frame at the distal end of the cusp. In addition, at the base of each cusp, the circumferential extent of transverse (that is, on a line or on the plane of a circumferential single-plane curve of folding that is generally perpendicular to the flow axis of the valve) folding of the membrane to the frame is less than the circumferential extent of transverse folding at the distal end of the cusp.

At least one embodiment, a prosthetic valve described herein comprises an integrated cusp and leaflet structure wherein the apposing sides of the cusp are joined at one or more axially oriented seams. In at least one embodiment, all folds and seams are located on line segments.

At least one embodiment of the one or more present inventions does not include frame elements, such as support members, spanning the interior of the valve luminal to support one or more portions of the membrane sheet. Moreover, at least one embodiment of the one or more present inventions does not include any hardware shaping form inward of or attached to any portion of the mobile leaflet portion of the membrane.

In addition, at least one embodiment of the one or more present inventions does not utilize attachment of the leaflet layer to the frame along the substantially complete circumferential distance separating the commissures at any point below (more proximal than) the commissure tabs.

At least one embodiment of the one or more present inventions does not include a transverse fold or reflection of the leaflet layer along the substantially complete circumferential distance separating the commissures at any point below (more proximal than) the commissure tabs.

Nomenclature

For all embodiments presented herein it is to be understood that a "membrane" includes suitable materials for forming the cusps and leaflets. Accordingly, with regard to particular material types that may be used to form the membrane sheet, in at least one embodiment the membrane sheet forming the cusp or leaflet portions includes a one-piece, single layer sheet of biocompatible membrane, such as fixed mammalian pericardium tissue or synthetic biocompatible material, such as ePTFE. In at least one embodiment, the membrane sheet is made from a tissue preparation process that yields a leaflet material of suitable strength and durability for use in a prosthetic transcatheter deliverable heart valve. The content of WO 2011/109450A2 published on Sep. 9, 2011, is incorporated herein by reference. Although the membrane sheet is preferably a single piece of material, a membrane sheet formed of a plurality of pieces of material may be used, such as two to fifty or more pieces of material that are connected.

As used herein "proximal" means situated near or closer to the upstream or flow inlet end of the valve, and "distal" means situated near or closer to the downstream or flow outlet end of the valve. This convention is further applied in the description of the various folded structure elements (membrane sections, edge segments and fold lines) that are termed "proximal" or "distal" if the final position or orientation of said element within the completed folded structure satisfies the above definitions. Likewise, one of said elements is termed, "axial", "transverse" or "circumferential" to describe its position and orientation in the completed valve.

As used herein, a "cusp" means that structural portion of a valve related to a single leaflet that encompasses a space closed toward the lower (proximal) direction and open to the upper (distal) direction, formed by the joined and/or continuous structures of the mobile leaflet portion on the radially inner side and the cusp wall portion on the radially outer side. The "cusp" in the present invention is that structure described as having a substantially conical shape.

As used herein, the "mobile leaflet layer" or "leaflet" means that radially inward portion of the cusp that moves during operation of the valve. For example, when the valve is closing the mobile leaflet layer moves radially inward toward the central axis of the valve lumen. When the valve is opening, the mobile leaflet layer moves radially outward and away from the central axis of the valve lumen.

As used herein, the "cusp wall layer" means a portion of the cusp that resides radially outward of the mobile leaflet layer. In some embodiments, a portion of the cusp wall layer moves during operation of the valve. In other embodiments, the cusp wall layer remains substantially immobile during operation of the valve.

As used herein, the "cuff wall layer" means a portion of the folded membrane structure that resides radially outward of both the cusp wall layer and the mobile leaflet layer, and where present, is radially closest to the frame of the three layers comprising the mobile leaflet layer, the cusp wall layer, and the cuff wall layer. The cuff wall layer remains substantially immobile during operation of the valve.

A "frame" as used herein means a substantially tubular member that holds a plurality of cusps and/or leaflets. By way of example, the frame may be a wire lattice or a lattice cut from a single tubular piece of metal alloy, that is both collapsible and expandable.

A "valve" as used herein means a frame with a plurality of cusps and/or leaflets attached thereto. In the present invention each of said leaflets is an integral part of a folded membrane cusp structure. If a frame is used that is a metal lattice that is both collapsible and expandable, such a construct may be delivered through a catheter percutaneously to a target site within a patient, such as the aortic valve.

As used herein, "cone" or "conical" means resembling a cone or portion thereof at some point in the practical use of the structure.

As used herein "substantially conical" means resembling a cone or a portion thereof at some point in the practical use of the structure with the specific property that the transverse (that is, on a plane of section generally perpendicular to the axis of flow of the valve) cross-sectional perimeter or area of said structure in the operationally closed position decreases monotonically moving from the level of the leaflet apposition to the proximal end of the valve.

As used herein, "two or more leaflets," "two or more valve leaflets," "a plurality of leaflets" or a similar term means two, three, four, or more valve leaflets. Accordingly, "a valve with two or more leaflets" includes a valve with two leaflets, a valve with three leaflets, a valve with four leaflets, and a valve with more than four leaflets.

As used herein, a "folding" means the partition of a flat sheet section of material along a sharp line of folding or crease into subsections each lying on separate planes, but without interruption of material continuity.

As used herein, a "complete folding" means folding (as above) wherein the angular change of the planar axis at the line of folding is approximately 180 degrees, such that the subsections lie on approximately parallel planes and the subsections are in approximate overlying contact with each other at least at some point.

As used herein, a "cuff" means that portion of a valve structure that lies radially outward of the cusp wall portion that in some part circumferentially encompasses at least a portion of the cusp structure and acts to limit flow that may pass retrograde around the cusp.

As used herein, "commissure" means the site of union or junction between adjacent cusps and/or leaflets, and by extension, collectively those portions of the adjacent integrated cusp and leaflet structures that are coincident at the union or junction in the completed valve structure.

As used herein, an "integrated cusp and leaflet folded structure" means a membrane folded in accordance with one of the patterns described herein.

Folded Valve Integrated Cusp and Leaflet—Folding Pattern No. 1

Referring generally to FIGS. 1A-7K, each cusp embodiment of an integrated cusp and leaflet structure described herein is a substantially flattened cone collapsed along an axis substantially perpendicular to its longitudinal axis. In one or more embodiments, the integrated cusp and leaflet structure, when being formed from a piece of membrane, is readily realized by folding a flat sheet of membrane from a closed polygon pattern. The pattern folding results in apposing seam lines aligned along their axial length. These are joined to close the cusp in the general shape of a cone with the joined seam forming the "spine" along which the cusp meets the inner aspect of the tubular frame. It can be seen that, when formed of a dry sheet membrane, the pattern results initially in a cusp shape that is an inverted pyramid with a rhomboid base that, with a flexible, pliable membrane, is congruent to a substantially conical shape. On relaxation of the folds in practical use a substantially conical cusp is realized wherein the inner mobile operating portions of the leaflet are continuous with the outer portion that forms the integral wall of the cusp sinus or pocket.

Referring now to FIG. 1A, a plan view of a rectangular flat sheet membrane template 100 is shown for the formation of a single-piece folded valve integrated cusp and leaflet. The plan view is shown with a view of that leaflet surface that faces radially inward once folded and mounted within a frame. Reference is also made to FIG. 1G, wherein a schematic of a valve in distal axial view is shown, and wherein three cusps with integral leaflets are shown within the frame that collectively form the valve. As described and illustrated in the present application, alternate polygons and other closed shapes may be employed with alternate folding patterns to generate alternate shapes and functional features of the valve cusp and leaflet, and complete valve.

Referring again to FIG. 1A, and in accordance with at least one embodiment of the one or more present inventions, dotted lines 101, 116, 117, 126 and 127 represent the position of folds or creases applied to a piece of membrane to form a leaflet structure 130. More particularly, folding at lines 116, 126 and 101 is initiated inward (with convexity of the surface disposed radially inward toward the central axis of the valve lumen) while folds 117 and 127 are folded initially outward (with convexity of surface disposed radially outward away from the central axis of the valve lumen). Since folding causes re-orientation of the various sections of the sheet template in relation to each other and to the valve geometry, final orientation of the fold lines within the structure on mounting and operation of the leaflets will not necessarily retain the same orientations as on initiation of the folds. The "inward" and "outward" conventions by this definition will be followed throughout the descriptions of the various folded geometries presented herein.

Referring again to FIG. 1A, a line of division by cutting is indicated at 102. Cutting at 102 results in opposing edges 115 and 125 that will be separated by folding. The other free edges of the structure are labeled as their position and orientation changes through the folding steps. Fold 101 defines the central axis of symmetry of the leaflet pattern, with the concave side of fold 101 facing radially outward toward the frame and away from the central axis of the valve lumen. Fold 101 assists in the maintenance of axial symmetry of the folded construct, but is not necessary to leaflet function and is not retained in the final operational form of the valve. (See FIG. 7A.)

Figure 1B:
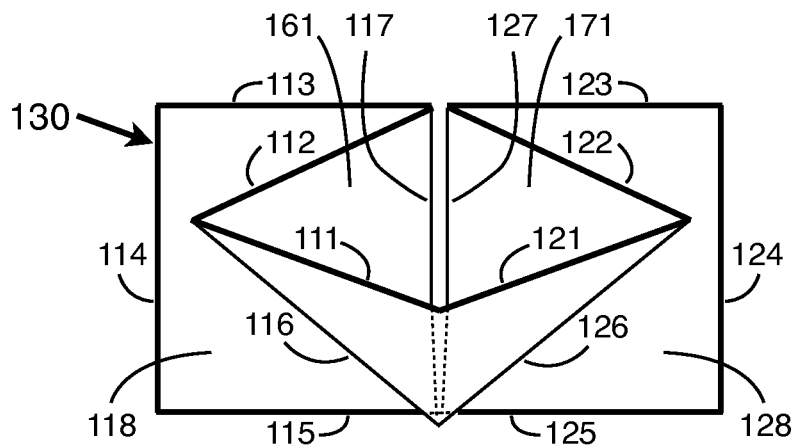
FIG. 1B is an oblique axial top (distal) perspective view directed downward (proximal) and radially outward of a folded membrane sheet after execution of the template foldings illustrated in FIG. 1A, thereby yielding a completed integrated cusp and leaflet folded structure.

Referring now to FIG. 1B, an oblique axial top (distal) perspective view of a substantially completed folded leaflet structure 130 is shown. (Three completed folded cusp and leaflet structures 130 are typically mounted to a frame to form an operating heart valve.)

The view of FIG. 1B is directed downward (proximally) and radially outward, with such view illustrating a substantially completed folded leaflet and cusp structure 130 that depicts the reoriented segments and sections of FIG. 1A after execution of the template foldings. Segments 111 and 121 form the left and right halves of the distal free edge of the mobile operating portion of the leaflet. Inward folding at 116 and 126 forms a second layer of membrane outward of the first, with segments 112 and 122 forming the distal free margin of the outer wall of the integrated cusp. In radially flatted form of the integrated cusp and leaflet structure (that is, approximating the open operating position of the leaflet), the segment 111 will appose to 112, and 121 will appose to 122.

The left cusp wall section 161 is bounded by folds 116 and 117 and edge segment 112. The right cusp wall section 171 is bounded by folds 126 and 127 and edge segment 122.

The left cuff wall section 118 is bounded by fold 117 and edge segments 113, 114 and 115. The right cuff wall section 128 is bounded by fold 127 and edge segments 123, 124 and 125. Inward folding at 117 and 127 cause these cuff wall sections 118 and 128 to position outward of the cusp wall sections 161 and 171, respectively. In radially flatted form of the completed folded structure (again, approximating the open operating position of the leaflet), the edge segment 113 will appose to 112, and edge segment 123 will appose to 122.

Folded Valve Folding Sequence

Figure 1C:
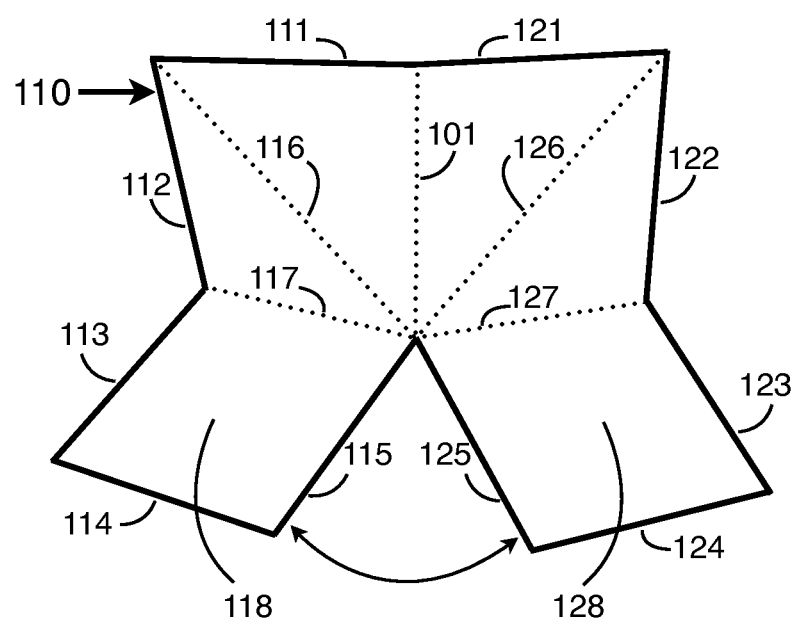
FIG. 1C is a side perspective view directed radially outward of the inner aspect of an initially folded version of the integrated cusp and leaflet template shown in FIG. 1A.
Figure 1D:
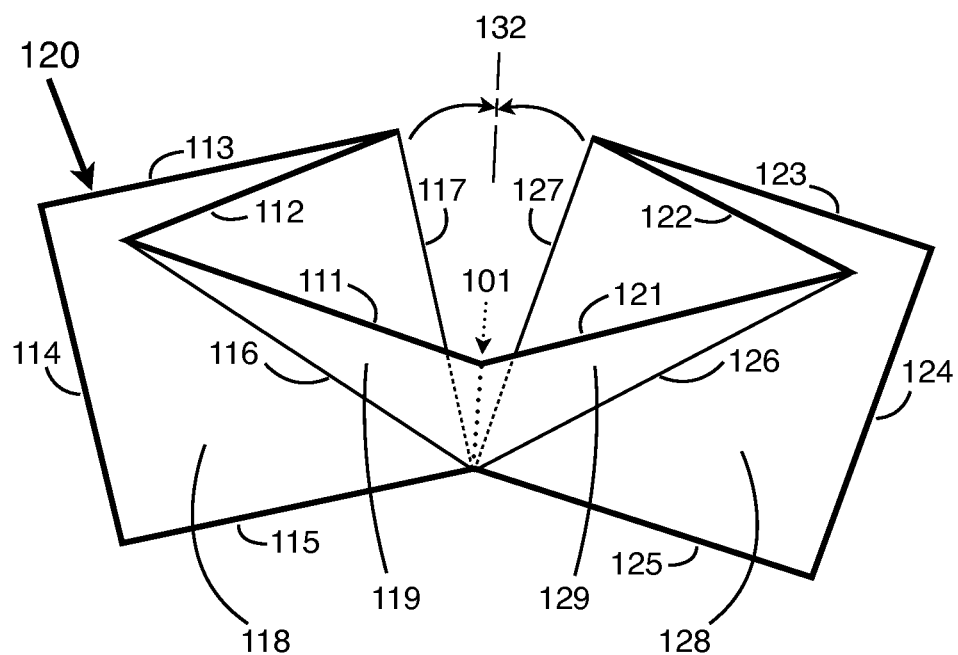
FIG. 1D is an oblique axial top (distal) perspective view directed downward (proximal) and radially outward of a further partially folded version of the integrated cusp and leaflet folded structure shown in FIG. 1C.

Referring now to FIGS. 1C and 1D, oblique axial top (distal) perspective views of a partially completed folded leaflet and cusp are shown. The views provided by FIGS. 1C and 1D are directed downward (proximally) and radially outward, with such views depicting the reoriented segments and sections of FIG. 1A after partial execution of the template foldings.

FIG. 1C shows a perspective view of the inner aspect of the template 100 after initiation of the foldings and cutting at 102 resulting in left and right cuff wall sections 118 and 128, respectively. The cut free edges 115 and 125 are separated along with the left and right cuff wall sections 118 and 128 by outward folding at 117 and 127, respectively. Completed folding at 117 and 127 results in the cuff wall sections 118 and 128, respectively. Distally situated (with respect to the blood flow direction) edge segments 113 and 123 of the cuff wall sections 118 and 128, as well as proximally situated edge segments 115 and 125 of the cuff wall sections 118 and 128, are positioned transverse, and in at least one embodiment, substantially perpendicular, to the central axis of the valve.

FIG. 1D shows the cusp and leaflet structure 120 with the folds 116, 126, 117 and 127 at an intermediate stage of completion. Triangular left and right mobile leaflet sections 119 and 129 respectively are bounded by folds 101 and 116 and free edge segment 111 on the left, and folds 101 and 126 and free edge segment 121 on the right. Folds 117 and 127 are then brought into apposition on the outward aspect of the integrated cusp and leaflet along a seam line 132 where the folds will be joined and attached to a frame to close the shape of the single-piece continuous conical integrated cusp and leaflet.

Figure 1E:
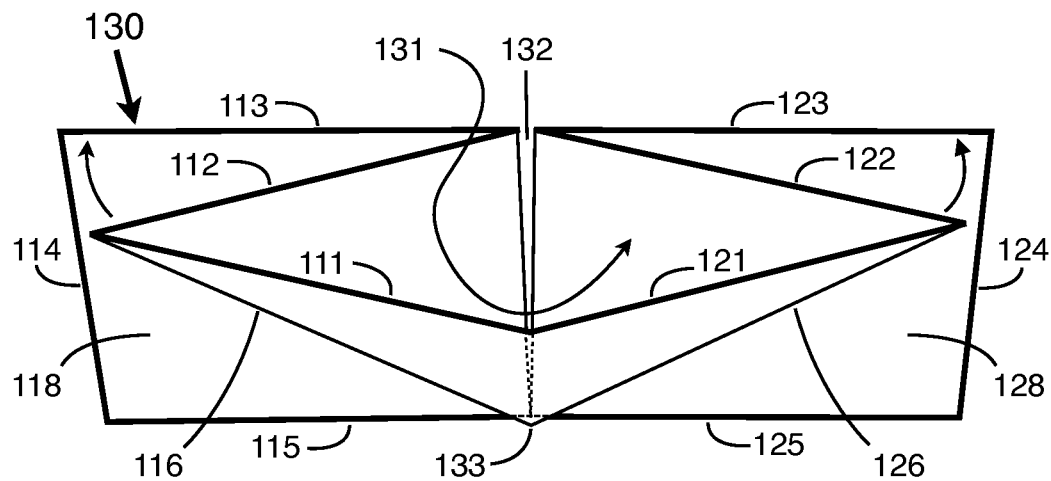
FIG. 1E is an another oblique axial top (distal) perspective view directed downward (proximal) and radially outward of a further partially folded version of the integrated cusp and leaflet folded structure shown in FIG. 1D.
Figure 1F:
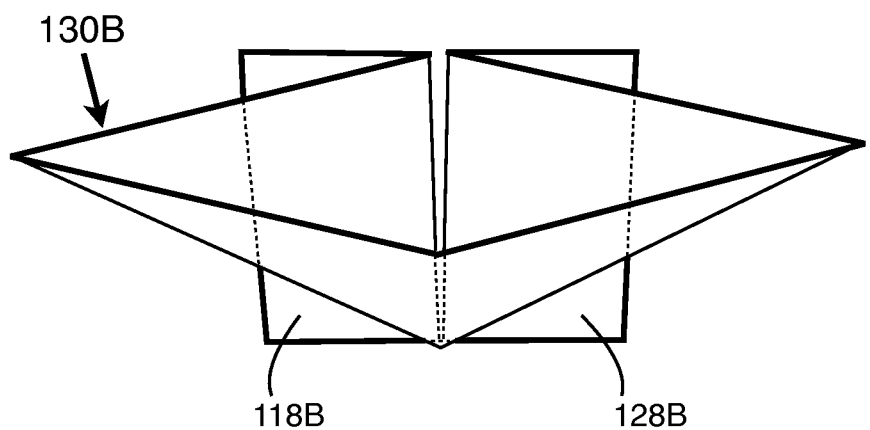
FIG. 1F is a modified version of the integrated cusp and leaflet folded structure shown in FIG. 1E.

Referring now to FIGS. 1E and 1F, oblique axial top (distal) perspective views of a substantially completed folded cusp and leaflet are shown. The views provided by FIGS. 1E and 1F are directed downward (proximally) and radially outward, with such views depicting the reoriented segments and sections of FIG. 1A after execution of the template folding s.

FIG. 1E shows the cusp and leaflet folding substantially completed forming the structure 130 with the seam 132 formed by the apposition of folds 117 and 127, thus forming a generally conical cusp and sinus space 131. The triangular corners formed at the distal ends of folds 116 and 126 are apposed to and attached to the cuff wall sections 118 and 128, respectively. Between adjacent cusp and leaflet structures in a multi-leaflet valve, the folded corners form the junction joining the adjacent free edges (121 of leaflet A to 111 of leaflet B, for example) of the mobile leaflet portions. When further attached to the circumferential valve frame, these corners tether the free edges of the mobile leaflet portions to the circumferential inner boundary of the generally cylindrical valve frame, thus forming valve leaflet commissures at each similar join.

Referring now to FIG. 1F, a structure similar to that of FIG. 1E is depicted, but with the cuff wall sections 118B and 128B reduced in circumferential extent from that of leaflet structure 130 shown in FIG. 1E. More particularly, depending on the clinical application of the valve, a fully circumferential cuff wall may be unnecessary, and a valve with a limited cuff wall with less tissue membrane mass may offer functional advantages. Alternatively, an additional piece of membrane may be placed circumferentially around the outer abluminal surface of the valve frame to act as a sealing cuff to form a barrier against valvular regurgitation.

Referring again to FIG. 1E, the apex 133 (proximal tip) of the conical cusp and leaflet forms the lower (proximal) end of the seam 132. In at least one embodiment, the apex 133 is also attached to the circumferential boundary of the valve and valve frame.

Referring now to FIG. 1G, for ease of reference the structure of FIG. 1E is again shown in FIG. 1G at the top of the page, along with a top (distal) cross-section view of the distal end of a three-leaflet valve in the closed operating position. The three cusps with leaflets are shown residing within a lattice frame in order to indicate the configuration of elements between the folded integrated cusp and leaflet structure 130 and its disposition within a three-leaflet frame-mounted valve. Suture attachments are omitted for clarity.

For each folded integrated cusp and leaflet structure, the outer axial seam 132 is aligned with one or more frame members 141 in a manner to permit the attachment of the folds 117 to 127, and to the coincident frame member by the same attachment, for example, by a single knot or line of suture. Advantageously for this purpose, the frame may preferentially contain axially oriented members that align to the seam 132 for part or all of the full axial extent of the valve. Further, said axially oriented members may advantageously contain holes or notches for securing and tying suture.

In FIG. 1G at point A, an illustrated loop symbolizing a suture knot is shown to demonstrate that a single knot may advantageously pass through or engage the frame member and the six layers; that is, the mobile leaflet section, the cusp wall section, and the cuff wall section of each adjoining cusp and leaflet structure that are coincident at this site of the commissure.

Referring still to FIG. 1G, it can be seen that the folded integrated cusp and leaflet structure, when mounted within the lattice frame and placed in the closed operating position, manifests the following configurations: (1) the left leaflet free edge segment 111 is in each case apposed to the right leaflet free edge segment 121 of the adjacent leaflet; (2) the portions of the leaflets just proximal to the free edges, thus, are also apposed to form the contact seal that enables effective closing operation, thereby preventing valvular regurgitation; and (3) the distal edges 112 and 122 of the cusp wall sections are apposed to the distal edges of the cuff wall sections 113 and 123, respectively.

Folded Valve Pattern Variation No. 2

Figure 2:
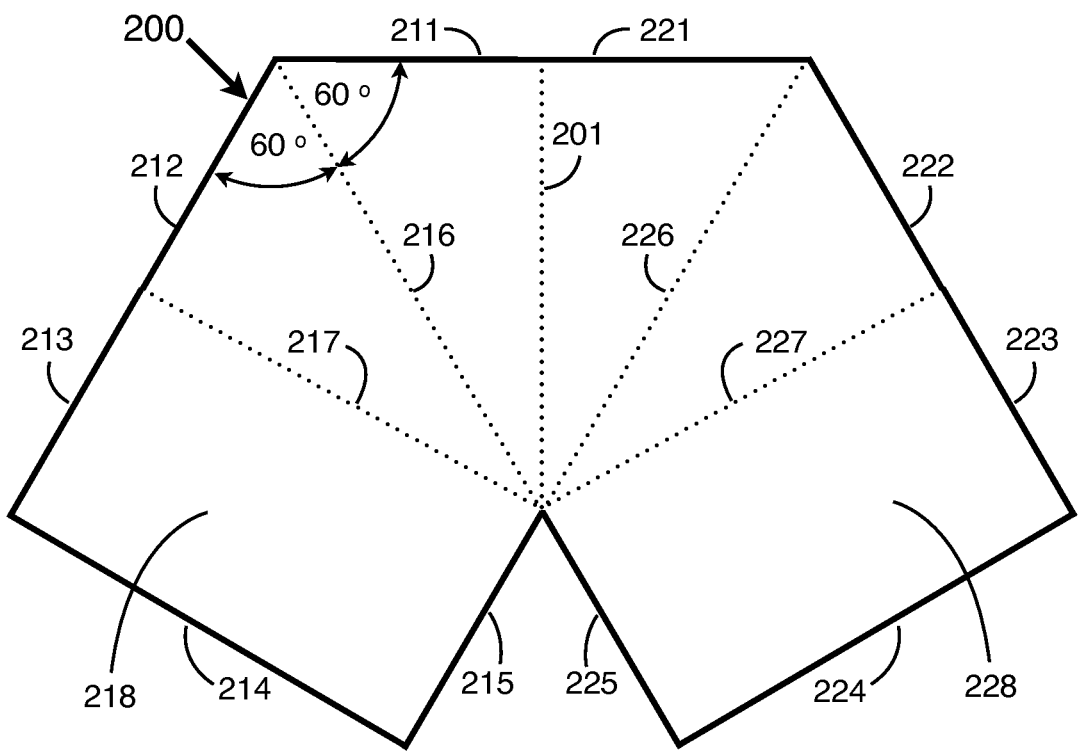
FIG. 2 is a plan view of another flat sheet membrane template for the formation of an integrated cusp and leaflet folded structure in accordance with at least one embodiment of the one or more present inventions.

Referring now to FIG. 2, and in accordance with at least one embodiment, a plan view of a flat sheet membrane template 200 that is polygonal rather than rectangular is shown. Template 200 contains folds 201, 216, 226, 217 and 227 that correspond to folds 101, 116, 126, 117 and 127, respectively, and are disposed in like manner in folding execution, as are the segments enumerated. The folding pattern is designed to form a longer cone of the same diameter, which achieves a more distally disposed central point of valve leaflet coaptation, the mechanics of which are more tolerant of pressure loads. The pattern dimensions may be altered to suit the particular clinical application of the valve. The template examples disclosed herein are for enablement purposes and shall not be interpreted as limiting the scope of the claims. The example is shown for a cusp cone wall disposed at about a 60 degree angle to the horizontal (short axis) of the generally cylindrical valve geometry, whereas that angle for the rectangular pattern of FIGS. 1A-1G was about 45 degrees.

Folded Valve Pattern Variation No. 3

Figure 3:
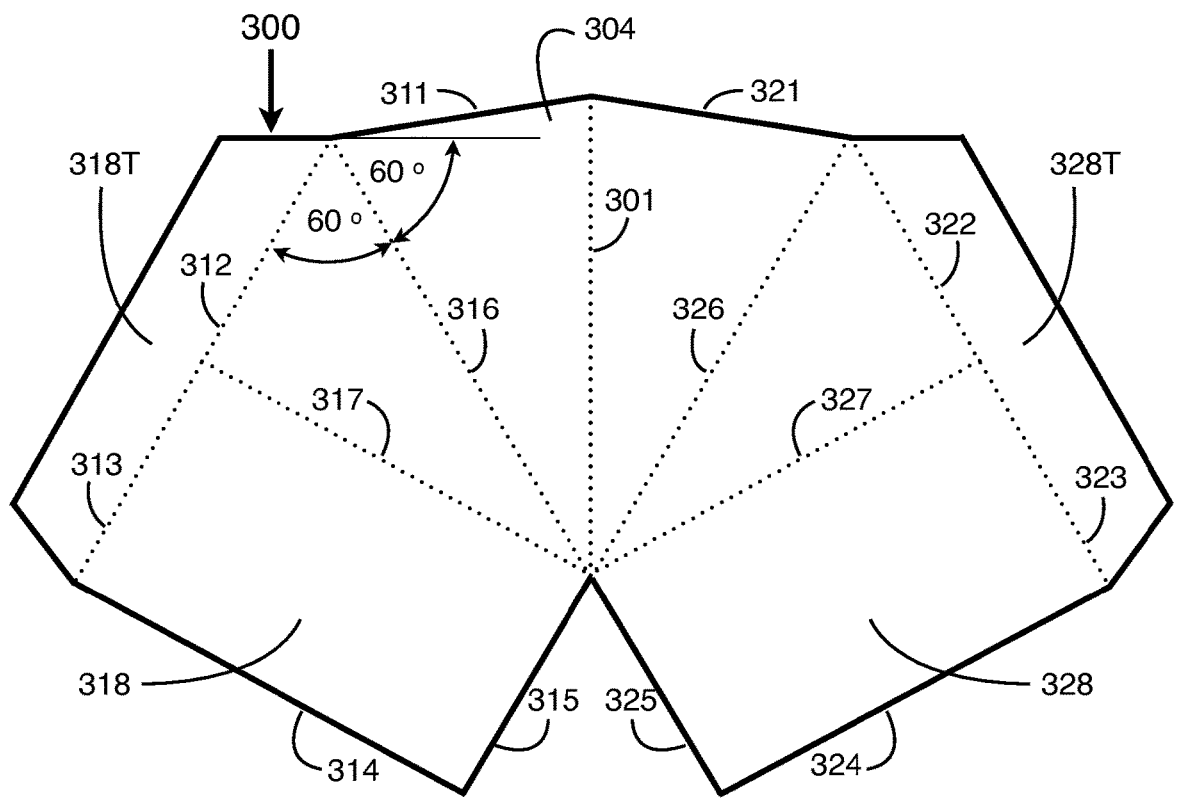
FIG. 3 is a plan view of yet another flat sheet membrane template for the formation of an integrated cusp and leaflet folded structure in accordance with at least one embodiment of the one or more present inventions.

Referring now to FIG. 3, and in accordance with at least one embodiment, a plan view of template 300 is shown for a flat sheet membrane that contains the pattern 200 of FIG. 2 with added sections that extend the distal contour of the structure when completed in folding. More particularly, the free edge of the mobile leaflet section is extended distally with a section having a polygonal or curved free edge in order to increase the contacting area of leaflet apposition in valve closing operation. Additionally, the distal contour of the cusp wall sections and cuff wall sections 318 and 328 are extended by "tab" sections 318T and 328T, respectively. These added "tab" extensions allow for increased area by which to mount the outer wall of the cusp and leaflet assembly to the frame and for elevating the cuff wall "above" (more distal to) the plane of leaflet apposition, thereby also increasing the effective volume of the cusp in closing operation. These "tab" extensions, being distally disposed after completion of folding and initial mounting within the lattice frame, or a distal portion of them may optionally be folded radially outward along 312-313 and 322-323, for example, to wrap around the distal edge of the frame such that the "tab" extension areas 318T and 328T lie on the outer, abluminal aspect of the frame where, when attached to the frame, they potentially increase the strength of the cusp attachment.

Referring still to FIG. 3, template 300 contains folds 301, 316, 326, 317 and 327 that correspond to folds 101, 116, 126, 117 and 127, respectively, and are disposed in like manner in folding execution, as are the edge segments similarly enumerated. In addition to the tab features discussed in the preceding paragraph, as with template 200, template 300 is designed to form a longer cone of the same diameter, which achieves a more distally disposed central point of valve leaflet coaptation. Again, the pattern dimensions may be altered to suit the particular clinical application of the valve. The example is shown for a cusp cone wall disposed at about a 60 degree angle to the horizontal (short axis) of the generally cylindrical valve geometry.

Folded Valve Pattern Variation No. 4

Figure 4:
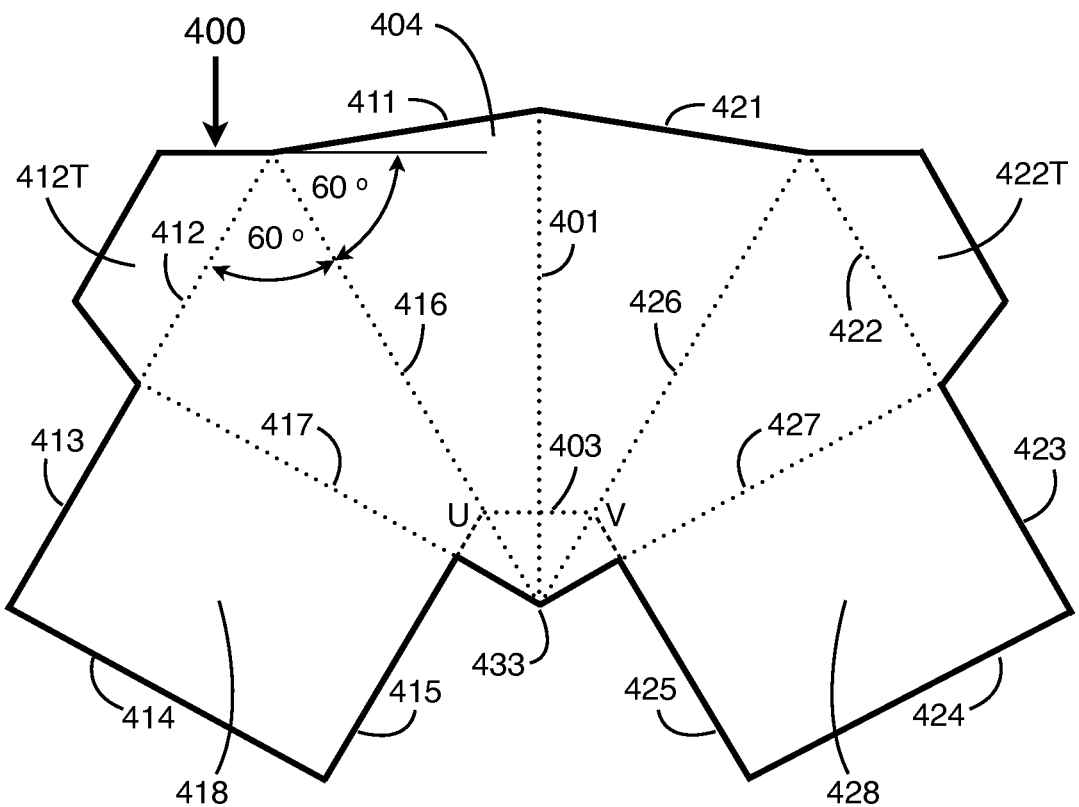
FIG. 4 is a plan view of still yet another flat sheet membrane template for the formation of an integrated cusp and leaflet folded structure in accordance with at least one embodiment of the one or more present inventions.

Referring now to FIG. 4, and in accordance with at least one embodiment, a plan view of pattern 400 is shown for a flat sheet membrane similar to pattern 300, except that the extension "tab" sections 412T and 422T are distal extensions of the cusp wall sections only. This limitation reduces the double layer of membrane extension at the distal end of the completely folded integrated cusp and leaflet structure to a single layer, thereby reducing the mass of membrane in the heart valve which might otherwise disadvantageously limit the efficiency of collapsing and compressing the valve for use in the percutaneous/transcatheter delivery application.

In addition, at the lower (proximal) apex 433 of the cusp cone pattern the lower (proximal) extent of the cuff wall sections 418 and 428 is limited so as to "expose" the apex of the cone in the pattern. This feature allows, on the completely folded integrated cusp and leaflet structure, the transverse, radially outward folding of the tip of the cone-shaped cusp at line 403 between points U and V. (See FIG. 7.) The folding of the apex reduces the overall axial length of the cusp and leaflet structure, allowing for increased cusp/sinus volume for a given valve diameter and frame length.

The template 400 contains folds 401, 416, 426, 417 and 427 that correspond to folds 101, 116, 126, 117 and 127, respectively, and are disposed in like manner in folding execution, as are the edge segments similarly enumerated. Similar to templates 200 and 300 described above, template 400 dimensions may be altered to suit the particular clinical application of the valve. The example is shown for a cusp cone wall disposed at about a 60 degree angle to the horizontal (short axis) of the generally cylindrical valve geometry.

Folded Valve Pattern Variation No. 5

Figure 5A:
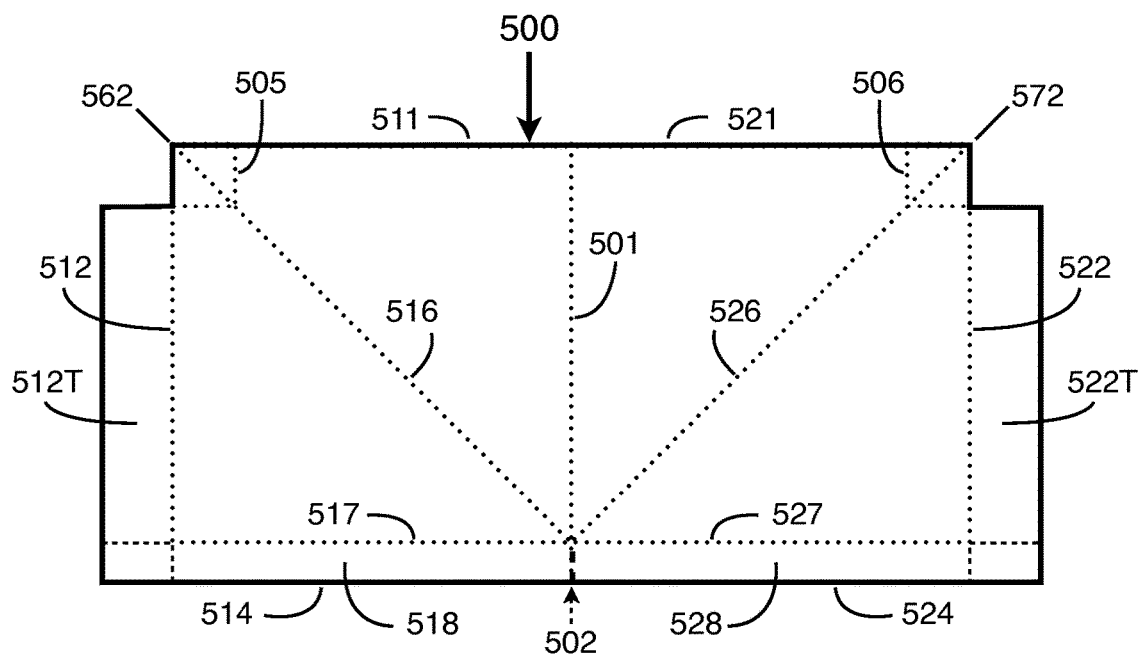
FIG. 5A is a plan view of another flat sheet membrane template for the formation of an integrated cusp and leaflet folded structure in accordance with at least one embodiment of the one or more present inventions.

Referring now to FIGS. 5A-5F, yet another embodiment of a template pattern is illustrated. Referring specifically now to FIG. 5A, a plan view of template 500 is shown for a flat sheet membrane. The template 500 contains folds 501, 516, 526, 517 and 527 that correspond to folds 101, 116, 126, 117 and 127, respectively, and are disposed in like manner in folding execution, as are the edge segments similarly enumerated.

Template 500 illustrates a flat sheet membrane that is basically rectangular and is similar to the upper (distal) portion of template 100 of FIGS. 1A-1G, except that (a) the distal extension areas 512T and 522T are added at the left and right margins of the template 500, and (b) the lower quadrants forming the cuff wall sections of the template 100 are truncated in template 500 to narrow cuff wall sections 518 and 528, the extent of which is defined by the length of cut 502. These limited interior cuff sections are still used for frame attachment along the central seam 532 of the cusp and leaflet cone, and the distal extension sections 512T and 522T are still used for attachment of the outer cusp wall to the distal edge of the frame.

Referring still to FIGS. 5A-5F, corner folds 505 and 506 are now described. For template 500, after folds 516 and 526 are executed by complete folding, segments 512 and 522 are apposed and aligned to segments 511 and 521, respectively, and overlapping layers (mobile leaflet layer and cusp wall layer) form triangular corner sections at 562 and 572. Radially outward folding of these corner sections at 505 and 506 define the axial extent of the leaflet commissures such that joining the corner sections of adjacent leaflet structures along corner folds 505 and 506 causes the leaflet apposition to be at least the length of 505 in axial extent at the radial margin of the leaflet. (See FIG. 9E that illustrates an embodiment of a valve comprising a frame 920 with a plurality of integral cusp and leaflet structures 730 attached to the frame, wherein the structures 730 include corner sections 762 and 772 corresponding to the corner sections 562 and 572 of template 500.) Additionally, these double-layer triangular corner sections 562 and 572 are used for attachment of the commissures to the frame. The stent frame may optionally contain a slot at this point of attachment through which this triangular "tab" section may be inserted and attached on the abluminal surface of the frame. (Again, see FIG. 9E.)

Figure 5B:
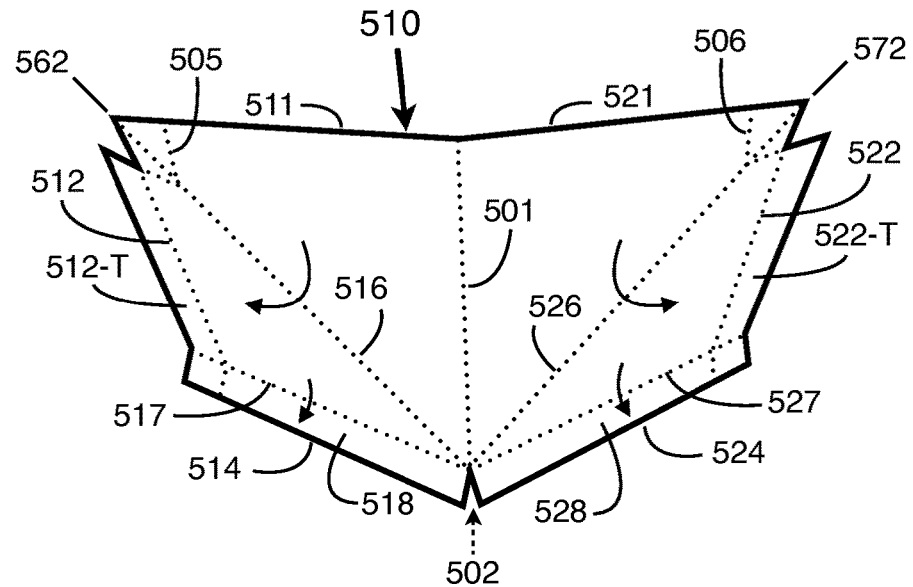
FIG. 5B is an oblique axial top (distal) perspective view directed downward (proximal) and radially outward of a partially folded version of an integrated cusp and leaflet folded structure prepared in accordance with the template shown in FIG. 5A.

With specific reference now to FIG. 5B, a perspective view of the inner aspect (that is, a view directed radially outward) of an initially folded structure 510 folded according to template 500 is shown. The central folding along 501 is initiated after cut 502 is executed as shown. Foldings along 501, 516, and 526 are depicted as initiated radially inward (out of the page) and foldings along 517 and 527 are depicted as initiated radially outward (into the page).

Figure 5C:
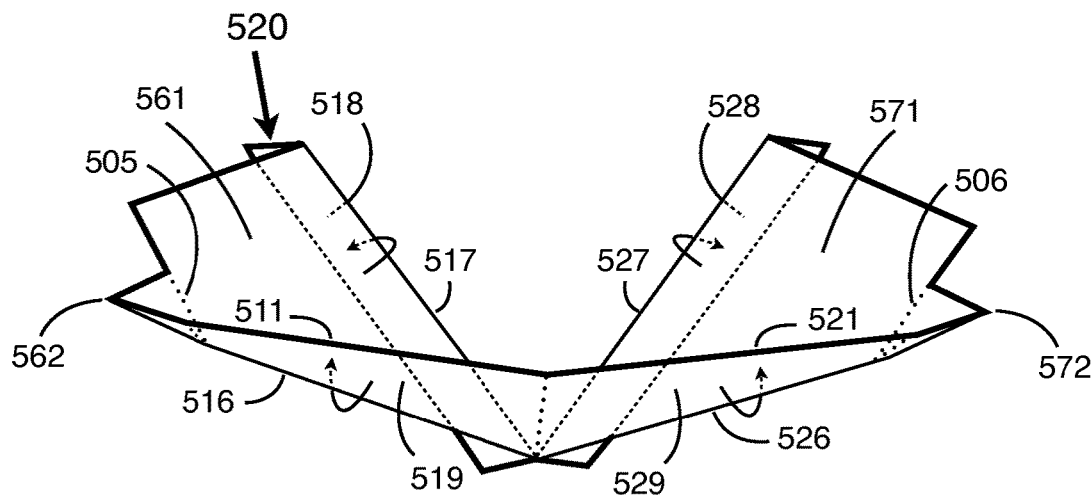
FIG. 5C is an oblique axial top (distal) perspective view directed downward (proximal) and radially outward of a further partially folded version of the integrated cusp and leaflet folded structure shown in FIG. 5B.

FIG. 5C shows a steeply oblique perspective view of the folded integrated cusp and leaflet 520 at an intermediate stage of completion of the foldings. The view is directed from the central axis outward and obliquely downward into the cusp space showing the formation of the outer wall of the structure, that is, the cusp wall layer of the subject cusp. Folding along 517 and 527 acts to position the extension sections 518 and 528 outward of the cusp wall sections 561 and 571, respectively. Completion of folding then will position folds 517 and 527 in an axially aligned orientation in apposition to each other along their length. Folding along 516 and 526 acts to position the cusp wall sections 561 and 571 outward of the mobile leaflet sections 519 and 529, respectively. Completion of folding, which radially collapses the folded flattened structure, positions the cusp wall sections 561 and 571 in apposition to the mobile leaflet sections 519 and 529, respectively. In the final folded configuration the structure embodies the integrated cusp and leaflet in the open operating position.

Figure 5D:
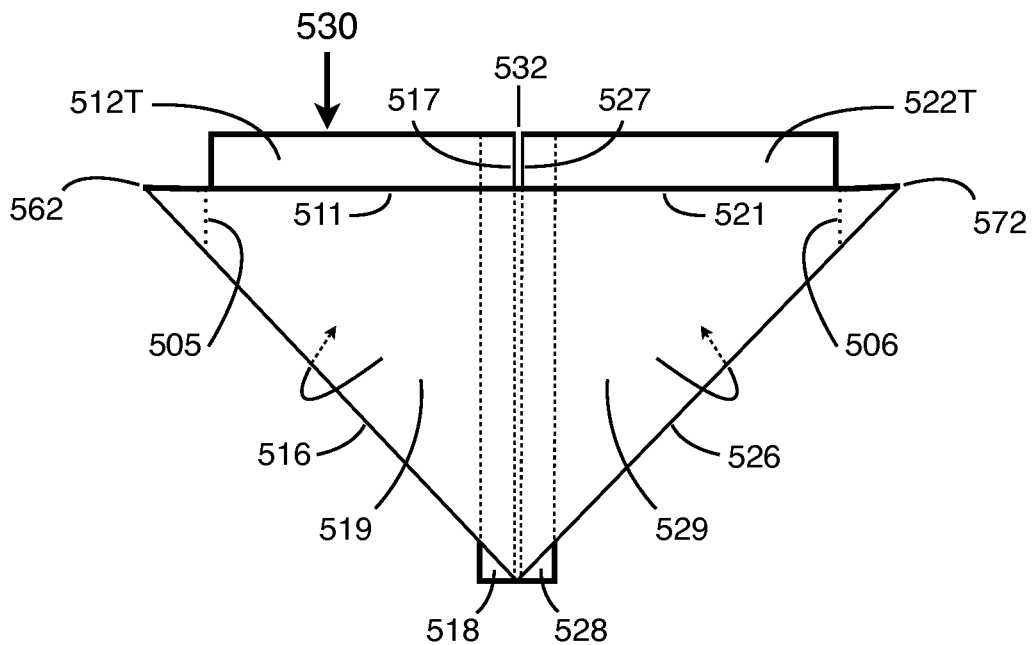
FIG. 5D is plan view of the inner (luminal) aspect of a completely folded version of the structure of FIG. 5C, thereby yielding a completed integrated cusp and leaflet folded structure prepared in accordance with the template shown in FIG. 5A (with the exception of unfolded commissure tabs)
Figure 5E:
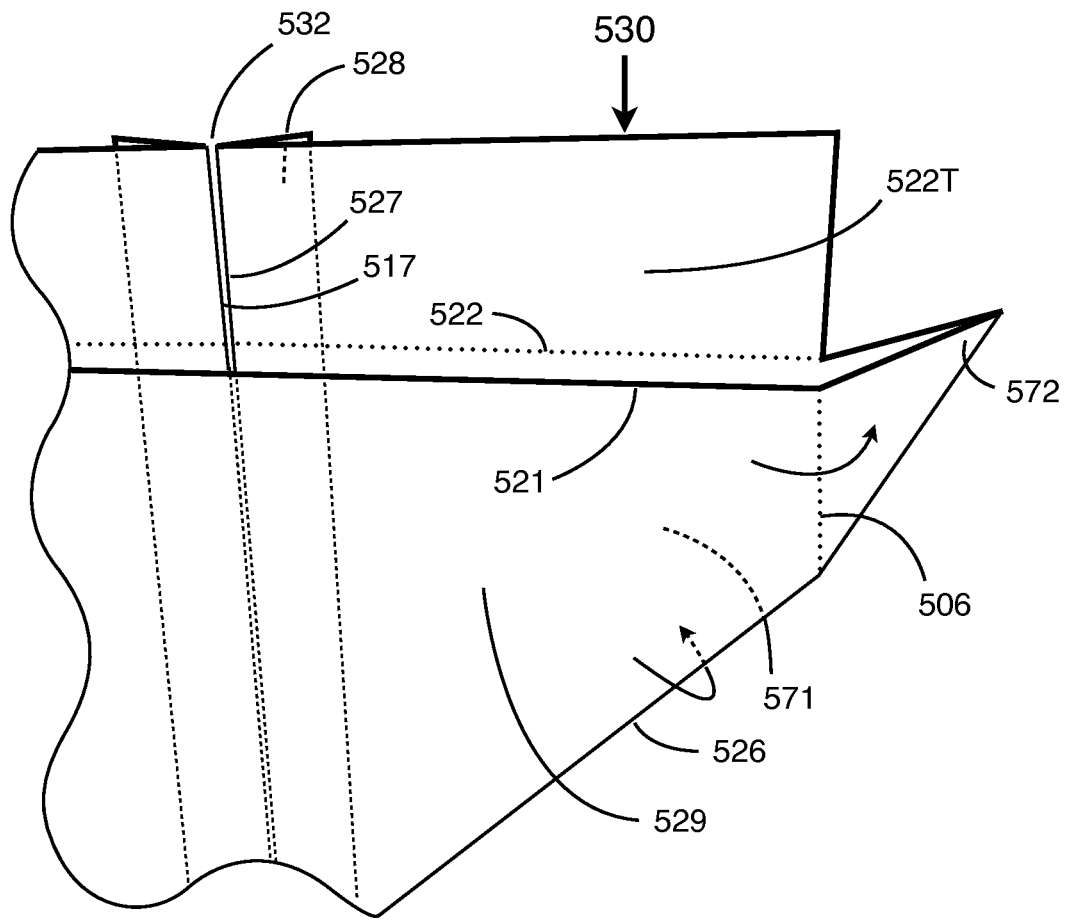
FIG. 5E shows a detail perspective view of a folded commissure tab.

In addition, completed folding at 516 and 526 also forms triangular two-layer sections, 562 and 572, respectively, that are designated as "commissure tabs". These commissure tabs are bounded by the corner folds 505 and 506, folds 516 and 526, and the free edges 511 and 521 of the mobile leaflet sections 519 and 529, respectively. With further reference to FIGS. 5D and 5E, these commissure tabs will be folded at 505 and 506 so as to position both layers of the tabs outward of the cusp wall sections 561 and 571, respectively, with the folds 505 and 506 oriented parallel to the central axis of the valve. With regard to a multi-leaflet valve, when the cusp and leaflet structure is mounted within the frame, this folded commissure tab is aligned along fold 505 in apposition to fold 506 of an adjacent complementary commissure tab of an adjacent integrated cusp and leaflet structure. Thus mounted, the commissure tabs join the mobile leaflet layers and the cusp wall layers of adjacent folded cusp and leaflet structures along a line coincident to both 505 and 506 that forms a common seam for attachment, such as by suturing of the commissure tabs to each other and to the frame forming the circumferential margin of the membrane portion of the folded cusp and leaflet structure.

FIG. 5D shows a plan view of the inner (luminal) aspect of the folded integrated cusp and leaflet structure 530 of template pattern 500. Structure 530 is depicted in a completed state of folding, excepting that the commissure tabs 562 and 572 are not yet folded outward along fold lines 505 and 506, respectively. The radially flattened form shown gives the general configuration and orientation of the membrane segments and sections for the open operating position of the valve cusp and leaflet.

Still referring to FIG. 5D, at the uppermost (distal) portion of the cusp wall layer, the extension tabs 512T and 522T are projected above (or distal to) the lines 512 and 522 (shown in FIGS. 5A and 5B), respectively, that lie in apposition and alignment to the free edges 511 and 521, respectively, of the mobile leaflet layer. A portion or all of these tabs 512T and 522T may be optionally folded outward along 512 and 522, respectively, around the distal edge of the frame to lie upon the outer (abluminal) surface of the frame where they may be attached to both the frame and to the cusp wall sections (where the cusp wall sections are apposed to the inner surface of the frame) through the interstices of the frame. This optional configuration provides for increased strength of attachment for bearing downward (proximally directed) operational loads associated with the valve closing.

Completing the folding associated with template pattern 500 places folds 517 and 527 into axial alignment. Once in axial alignment, apposing folds 517 and 527 are joined along their axial length to form the seam 532 that closes the generally conical cusp structure with the extension sections 518 and 528 situated outward of the cusp wall sections 561 and 571, respectively. The cusp wall sections 561 and 571 are thus disposed outward of the mobile leaflet sections 519 and 529, respectively, with the cusp wall sections axially and circumferentially apposed to the inner surfaces of the generally cylindrical frame. Advantageously, for each valve cusp and leaflet to be mounted within, the frame may contain an element or elements that are axially oriented and span a significant portion of the axial length of the frame, so as to align with the seam 532 for attachment, such as by suturing to the frame.

Referring now to FIG. 5E, a partial detail perspective view is shown of the commissure tab 572 configuration of the completely folded integrated cusp and leaflet structure 530, indicating radially outward folding of the commissure tab 572 along fold line 506.

Figure 5F:
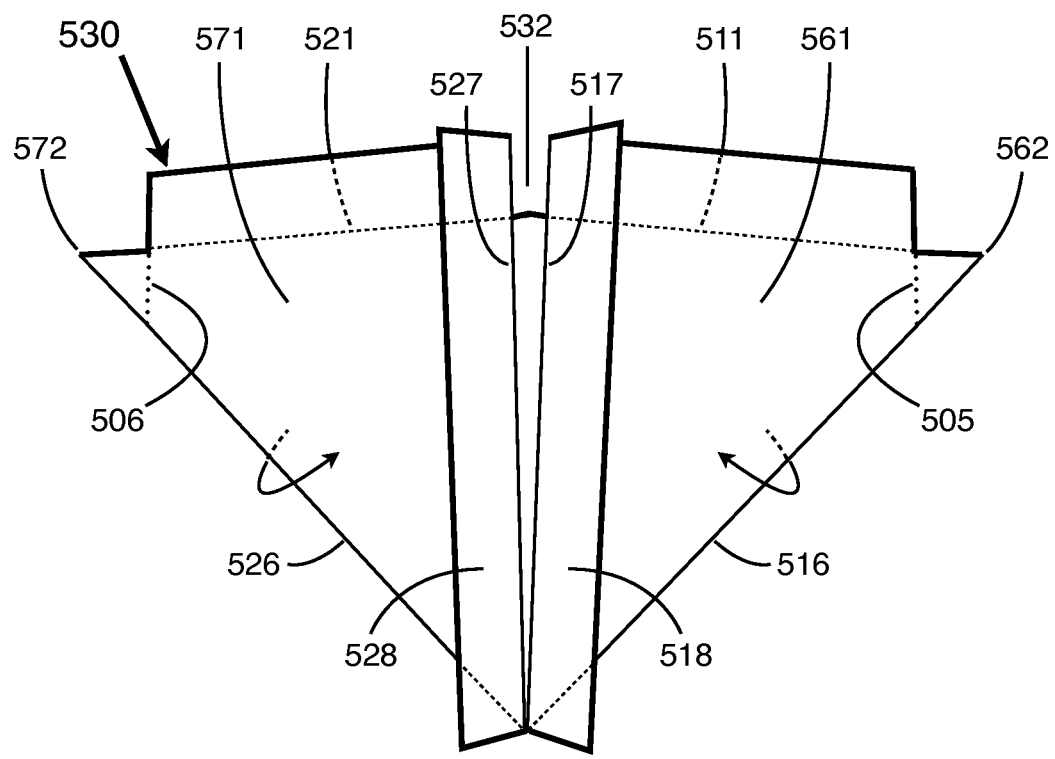
FIG. 5F shows a perspective view of the outer (abluminal) aspect of the device shown in FIG. 5D.

With reference now to FIG. 5F, a perspective view is shown of the outer (abluminal) aspect of the completely folded cusp and leaflet structure 530 (except that the triangular commissure tabs are not yet folded) of template 500 in substantially flattened form. This view is complementary to FIG. 5D that shows the inner aspect of the same structure 530. The central seam 532 is seen on the outer face of the cusp wall sections 561 and 571 and is depicted for purposes of illustration as partly separated with the extension sections 518 and 528 incompletely flattened and folds 517 and 527 in close, but not in the complete apposition and alignment that will form the final seam line 532 for attachment to the axially oriented frame members. The slight separation depicted between folds 517 and 527 exposes the centerpoint of the mobile leaflet free edge where the mobile leaflet free edge segments 511 and 521 meet as depicted behind the cusp wall sections 561 and 571, respectively, in this view.

Folded Valve Pattern Variation No. 6

Figure 6:
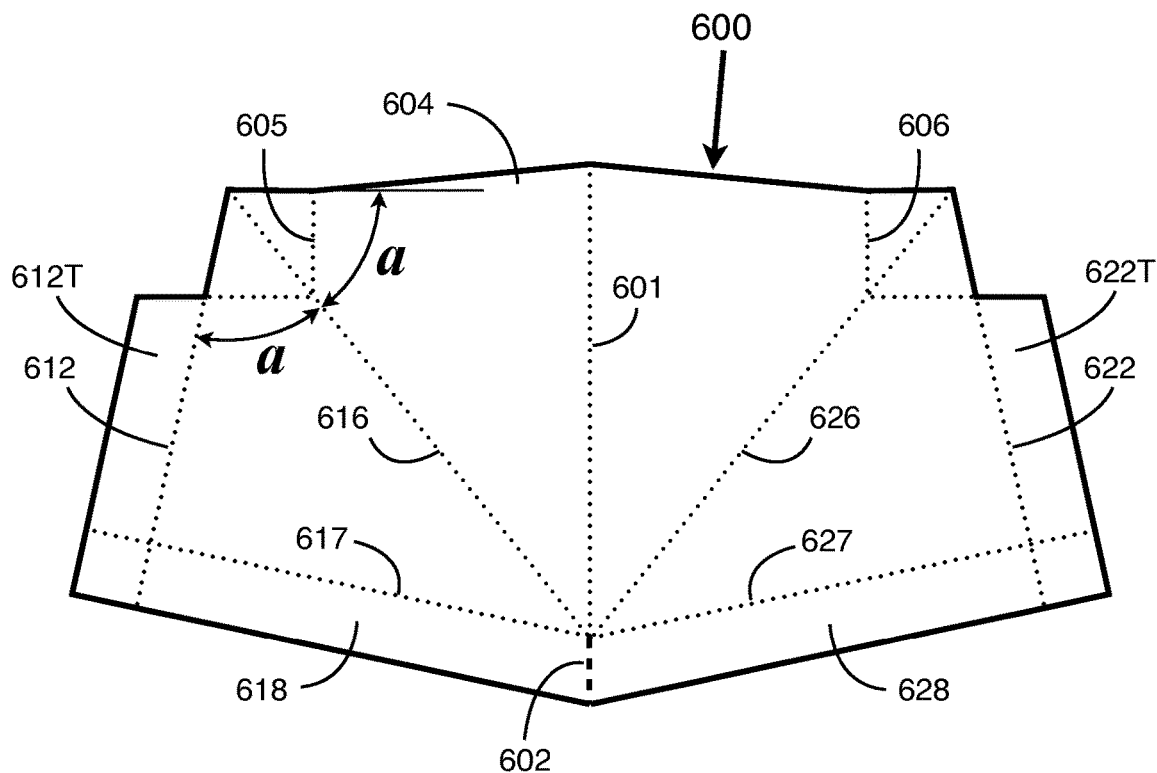
FIG. 6 is a plan view of yet another flat sheet membrane template for the formation of an integrated cusp and leaflet folded structure in accordance with at least one embodiment of the one or more present inventions.

In accordance with at least one embodiment, FIG. 6 shows a plan view of another template 600 that is similar to template 500 except that the cusp cone wall angle α exceeds the 45 degrees of the generally rectangular template 500, and that the mobile leaflet sections are extended by a polygonal or curved extension section 604 of the free edge.

The change in cusp cone wall angle α also results in changes in the angle relating the lower (proximal) margins of the template and fold lines 617 and 627 to the center line of the template in order that when folding is completely executed, the fold lines 617 and 627 and the seam between them will be parallel to the central axis of the assembled valve. Likewise, the further geometry of the cusp cone wall angle will result in fold lines (optional) 613 and 623 and the long axes of extension tabs 612T and 622T being parallel to the transverse axis of the assembled valve.

The template 600 contains folds 601, 616, 626, 617, 627, optional folds 612 and 622, corner folds 605 and 606, and cut line 602 that correspond to folds 501, 516, 526, 517, 527, optional folds 512 and 522, corner folds 505 and 506, and cut line 502, respectively, of template pattern 500 and are disposed in like manner in folding execution, as are the template sections and edge segments similarly enumerated.

Folded Valve Pattern Variation No. 7

Figure 7A:
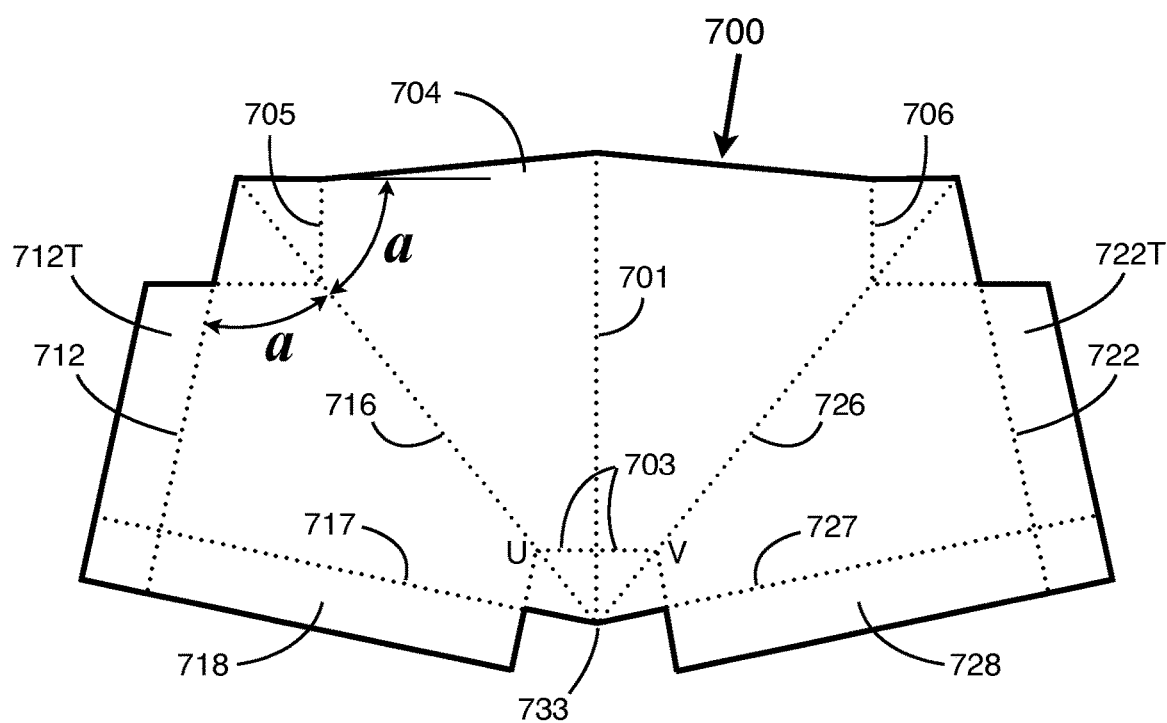
FIG. 7A is a plan view of still yet another flat sheet membrane template for the formation of an integrated cusp and leaflet folded structure in accordance with at least one embodiment of the one or more present inventions.

Referring now to FIGS. 7A-7F, still yet another embodiment of a template pattern is illustrated. Referring specifically now to FIG. 7A, a plan view of another template 700 is shown that is similar to template 600, but with a section of the lower (proximal) midline portion of the template cut away so as to expose the apex 733 of the triangular sections that, when folded, will form the apex of the cone-shaped cusp. Effectively, the midline portions of the extension sections 718 and 728 are removed in relation to template 600 to an extent determined by the desired length of the line segment U-V, which in turn determines the extent to which the apex of the cone-shaped cusp may be truncated by folding at U-V.

After the cusp and leaflet cone is formed by folding, the apex is folded radially outward at line U-V (703) to truncate the cone to reduce the overall length of the cusp and leaflet structure, allowing for increased cusp/sinus volume for a given valve diameter and frame length.

The template 700 contains folds 701, 716, 726, 717, 727, optional folds 712 and 722, and corner folds 705 and 706, that correspond to folds 601, 616, 626, 617, 627, optional folds 612 and 622, and corner folds 605 and 606, respectively, of template 600 and are disposed in like manner in folding execution, as are the template sections and edge segments similarly enumerated.

Figure 7B:
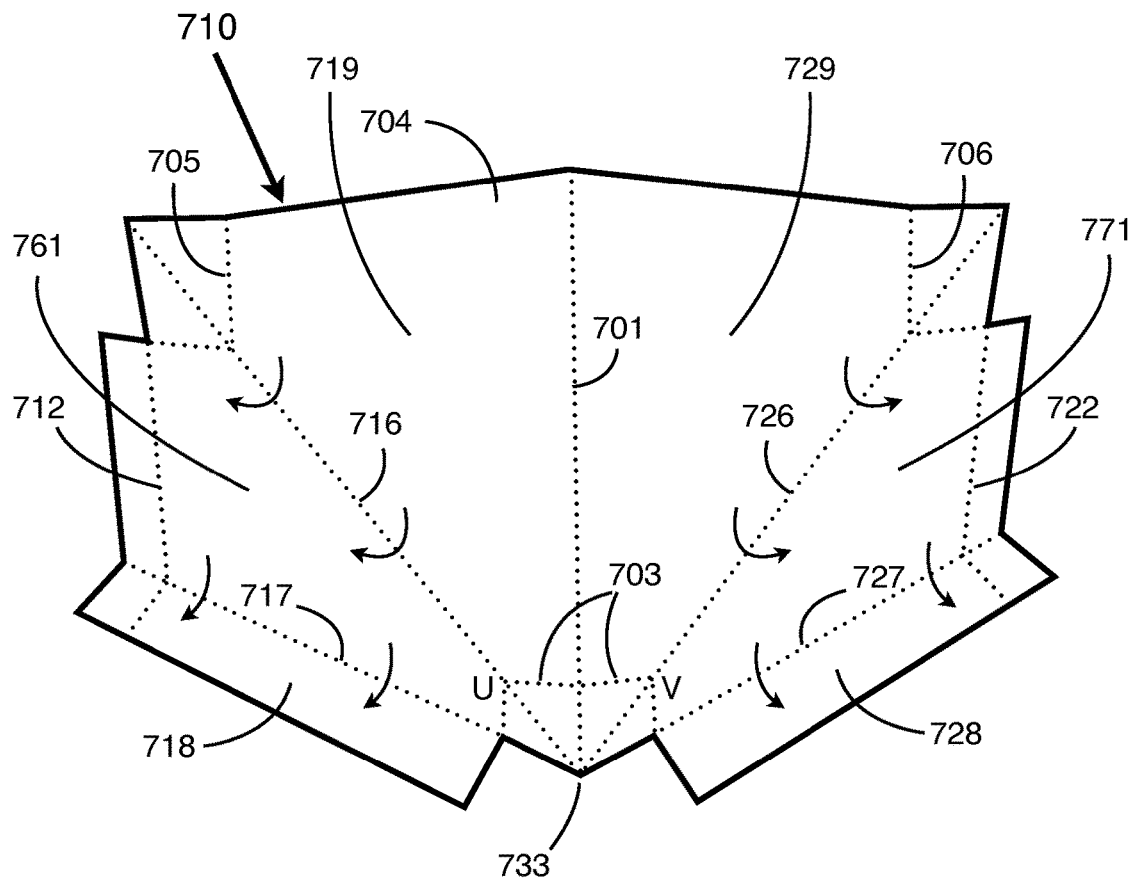
FIG. 7B is an oblique axial top (distal) perspective view directed downward (proximal) and radially outward of a partially folded version of an integrated cusp and leaflet folded structure prepared in accordance with the template shown in FIG. 7A.

FIG. 7B shows a perspective view of the inner (luminal) aspect of the initially folded cusp and leaflet structure 710 of template 700 after initiation of the principal folds 716, 726, 717, 727 and 701. Inward folding along 701 assists in aligning the left and right sections of the structure, but is not necessary to the formation of the integrated cusp and leaflet folded structure or to the operation of the valve. The disposition of the folds that converge at the apex 733 of the cusp can be appreciated as later forming an overlapping two-layer triangular apex as the cusp wall sections 761 and 771 are folded outward along lines 716 and 726, respectively, so as to position the cusp wall sections 761 and 771 outward of, and in apposition to, the mobile leaflet sections 719 and 729, respectively.

Figure 7C:
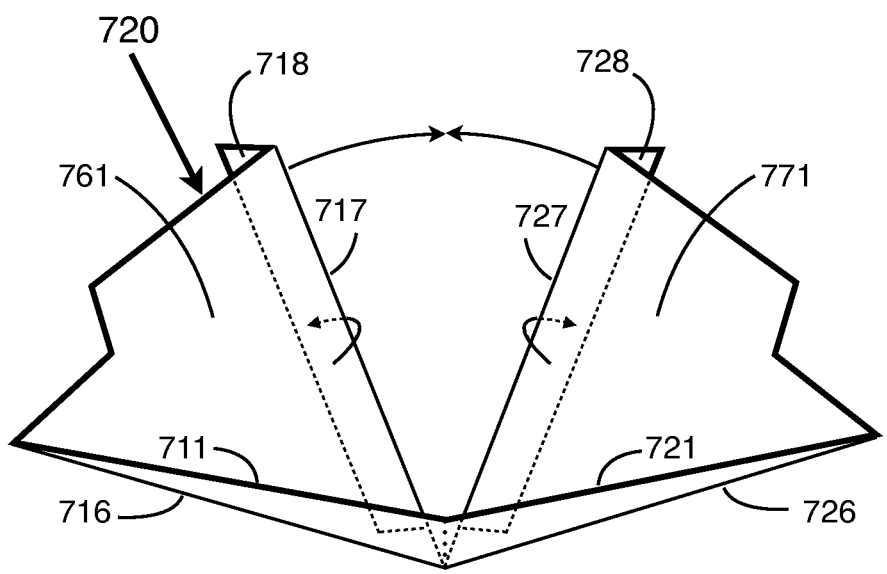
FIG. 7C is an oblique axial top (distal) perspective view directed downward (proximal) and radially outward of a further partially folded version of the integrated cusp and leaflet folded structure shown in FIG. 7B.

FIG. 7C shows a steeply oblique perspective view of the folded integrated cusp and leaflet 720 at an intermediate stage of completion of the foldings. The view is directed from the central axis outward and obliquely downward into the cusp space showing the formation of the outer wall of the structure. Folding along 717 and 727 acts to position the extension sections 718 and 728 outward of the cusp wall sections 761 and 771, respectively. Completion of folding then will position folds 717 and 727 in an axially aligned orientation in apposition to each other along their length. Folding along 716 and 726 acts to position the cusp wall sections 761 and 771 outward of the mobile leaflet sections 719 and 729, respectively. Completion of folding, which radially collapses the folded flattened structure, positions the cusp wall sections 761 and 771 in apposition to the mobile leaflet sections 719 and 729, respectively. In the final folded configuration, the structure embodies the integrated cusp and leaflet in the open operating position.

Figure 7D:
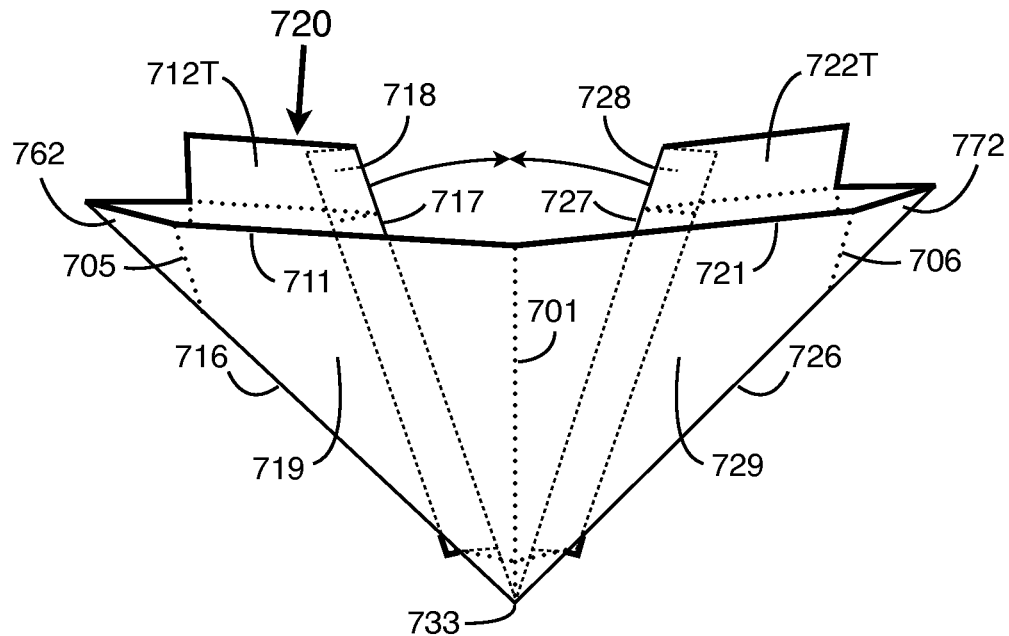
FIG. 7D is an oblique axial top (distal) perspective view directed downward (proximal) and radially outward of yet a further partially folded version of the integrated cusp and leaflet folded structure shown in FIG. 7C.
Figure 7E:
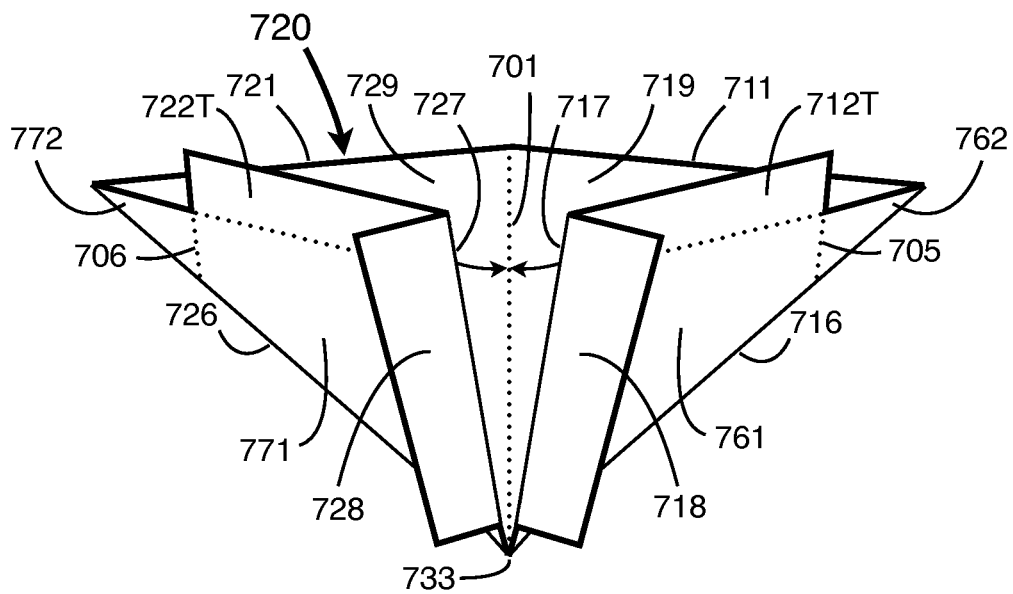
FIG. 7E shows a shallow oblique top perspective view of the outer (abluminal) aspect of the partially folded cusp and leaflet structure of FIG. 7D.

With reference to FIG. 7D, completed folding at 716 and 726 also forms triangular two-layer sections, 762 and 772, respectively, that are designated as "commissure tabs." These commissure tabs are bounded by the corner folds 705 and 706, folds 716 and 726, and the free edges 711 and 721 of the mobile leaflet sections 719 and 729, respectively. With further reference to FIGS. 7D and 7E, these commissure tabs will be folded at 705 and 706 so as to position both layers of the tabs outward of the cusp wall sections 761 and 771, respectively, with the folds 705 and 706 oriented parallel to the central axis of the valve. When the integrated cusp and leaflet structure is mounted within the frame, this folded commissure tab is aligned along fold 705 in apposition to fold 706 of an adjacent complementary commissure tab of an adjacent integrated cusp and leaflet structure of a multi-leaflet valve. Thus mounted, the commissure tabs join the mobile leaflet layers and the cusp wall layers of adjacent folded cusp and leaflet structures along a line coincident to both 705 and 706 that forms a common seam for attachment, such as by suturing of the commissure tabs to each other and to the frame forming the circumferential margin of the membrane portion of the folded cusp and leaflet structure.

FIG. 7D shows a perspective view of the inner (luminal) aspect of the partially folded integrated cusp and valve structure 720 of template 700. Integrated cusp and leaflet structure 720 is depicted in nearly completed state of folding, except that the commissure tabs 762 and 772, as well as the cusp apex 733 are not yet folded outward along fold lines 705, 706 and 703, respectively, and that the axial seam 732 is not yet formed by the apposition of the folds 717 and 727.

At the uppermost (distal) portion of the cusp wall layer, the extension tabs 712T and 722T are projected above (or distal to) the lines 712 and 722 (shown in FIGS. 7A and 7B). All or a portion of these tabs 712T and 722T may be optionally folded outward along 712 and 722, respectively, around the distal edge of the frame to lie upon the outer (abluminal) surface of the frame where they may be attached to both the frame and to the cusp wall sections (apposed to the inner surface of the frame) through the interstices of the frame. This optional configuration provides for increased strength of attachment for bearing downward (proximally directed) operational loads associated with the valve closing.

Completing the folding associated with template pattern 700 places folds 717 and 727 into axial alignment. Once in axial alignment, apposing folds 717 and 727 are joined along their axial length to form the seam 732 that closes the generally conical cusp structure with the extension sections 718 and 728 situated outward of the cusp wall sections 761 and 771, respectively. The cusp wall sections 761 and 771 then are disposed outward of the mobile leaflet sections 719 and 729, respectively, with the cusp wall sections axially and circumferentially apposed to the inner surfaces of the generally cylindrical frame. Advantageously, for each integrated cusp and folded leaflet structure to be mounted within, the frame may contain an element or elements that are axially oriented and span a significant portion of the axial length of the frame, so as to align with the seam 732 for attachment as by suturing to the frame.

FIG. 7E shows a shallow oblique top perspective view of the outer (abluminal) aspect of the partially folded cusp and leaflet structure 720 of template 700 (except that the triangular commissure tabs 762 and 772 and apex 733 are not yet folded and that the axial seam 732 is not yet joined). This view is complementary to FIG. 7D that shows the inner aspect of the same structure 720. The central seam 732 will be formed on the outer face of the cusp wall sections 761 and 771 as folds 717 and 727 are brought together into apposition along the midline, with the extension sections 718 and 728 thus also aligned. The outward (abluminal) face of the mobile leaflet sections 719 and 729 are shown between the yet separated folds 717 and 727 before closure of the generally conical cusp along the outer seam 732.

Figure 7F:
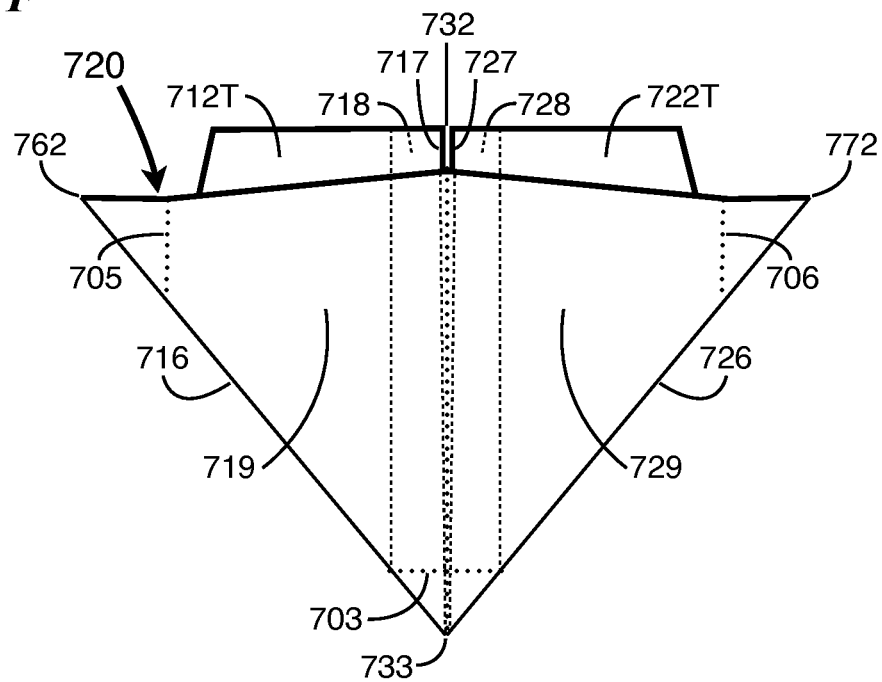
FIG. 7F is a plan view of the inner (luminal) aspect of a completely folded version of the structure of FIG. 7D yielding an integrated cusp and leaflet folded structure prepared in accordance with the template shown in FIG. 7A (excepting that the commissure tabs and apex are not yet folded outward)

FIG. 7F shows a plan view of the inner (luminal) aspect of the folded integrated cusp and leaflet structure 720 of template pattern 700. Structure 720 is depicted in a completed state of folding, excepting that the commissure tabs 762 and 772 are not yet folded outward along fold lines 705 and 706, respectively. In addition, the apex 733 is not folded outward. The radially flattened form shown gives the general configuration and orientation of the membrane line segments and areal sections for the open operating position of the valve cusp and leaflet.

At the uppermost (distal) portion of the cusp wall layer, the extension tabs 712T and 722T are projected above (distal to) the lines 712 and 722 (shown in FIGS. 7A, 7B and 7G), respectively, below (proximal to) which the cusp wall sections 761 and 771 lie in radial apposition to the mobile leaflet sections 719 and 729, respectively, of the mobile leaflet layer. These tabs 712T and 722T may be optionally folded outward along 712 and 722, respectively, around the distal edge of the frame to lie upon the outer (abluminal) surface of the frame where they may be attached to both the frame and to the cusp wall sections (apposed to the inner surface of the frame) through the interstices of the frame. This optional configuration provides for increased strength of attachment for bearing downward (proximally directed) loads of valve closing.

Folding of the template positions folds 717 and 727 into axial alignment, joined along their axial length to form the seam that closes the generally conical cusp structure with the extension sections 718 and 728 reflected outward of the cusp wall sections 761 and 771, respectively. The cusp wall sections 761 and 771 then are disposed outward of the mobile leaflet sections 719 and 729, respectively, with the cusp wall sections 761 and 771 axially and circumferentially apposed to the inner surfaces of the generally cylindrical frame. Advantageously, for each valve cusp and leaflet folded structure to be mounted within, the frame may contain an element or elements that are axially oriented and span a significant portion of the axial length of the frame, so as to align with the seam 732 for attachment as by suturing to the frame.

Figure 7G:
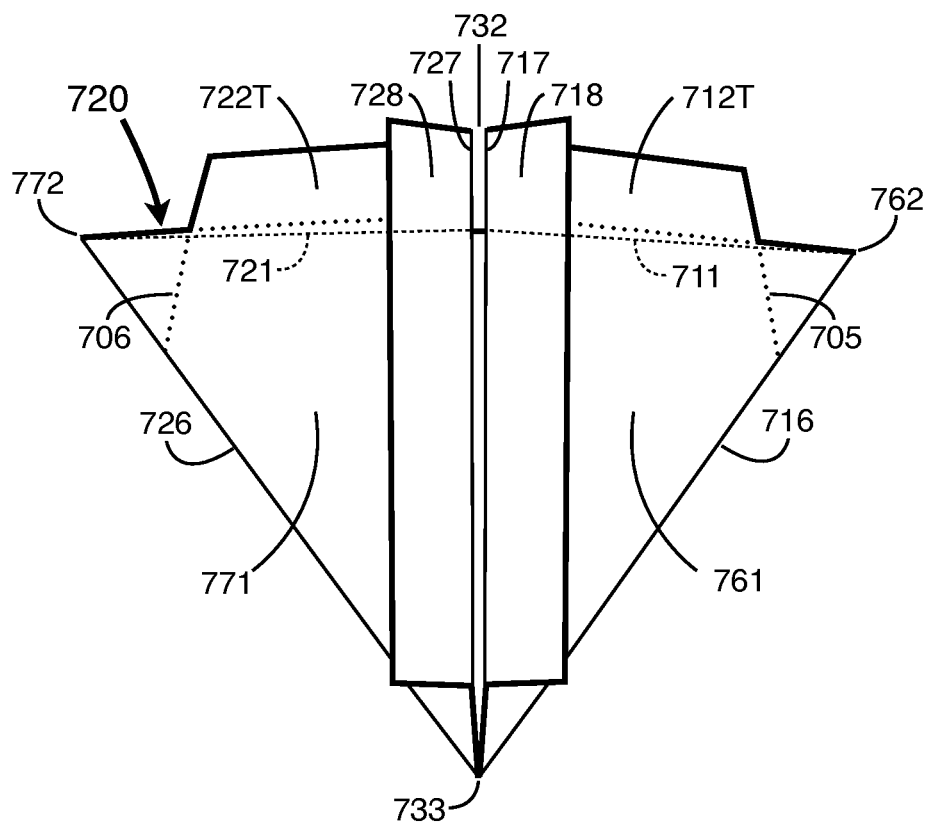
FIG. 7G is a side perspective view of the outer (abluminal) aspect of the structure of FIG. 7F showing a completely folded version of an integrated cusp and leaflet folded structure prepared in accordance with the template shown in FIG. 7A (excepting that the commissure tabs and apex are not yet folded outward)

FIG. 7G shows a perspective view of the outer (abluminal) aspect of the completely folded cusp and leaflet structure 720 (except that the triangular commissure tabs 762 and 772 and apex 733 are not yet folded) of template 700, in nearly flattened form. This view is complementary to FIG. 7F that shows the inner aspect of the same structure 720. The central seam 732 is seen on the outer face of the cusp wall sections 761 and 771 and is depicted for purposes of illustration as minimally separated with the extension sections 718 and 728 incompletely flattened and folds 717 and 727 in effectively complete apposition and alignment that forms the final seam line 732 for attachment to the axially oriented frame members. The slight separation depicted between folds 717 and 727 exposes the centerpoint between the mobile leaflet free edge segments 711 and 721 depicted behind the cusp wall sections 761 and 771, respectively, in this view.

Figure 7H:
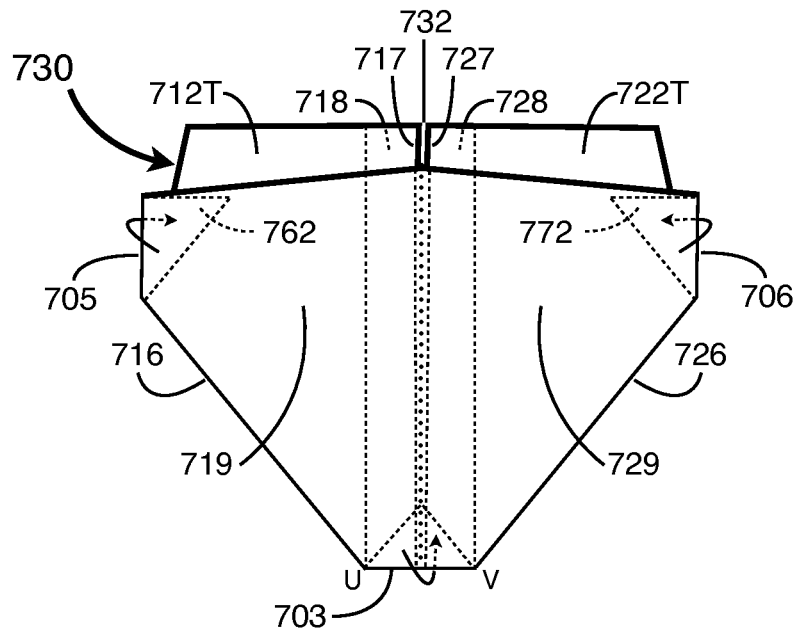
FIG. 7H is a plan view of the inner (luminal) aspect of a completely folded version of an integrated cusp and leaflet folded structure prepared in accordance with the template shown in FIG. 7A.

FIG. 7H shows a plan view of the inner aspect of the completely folded integrated cusp and leaflet structure 730 of template 700. This view is substantially that of FIG. 7F except that the triangular commissure tabs 762 and 772 are folded radially outward of the cusp wall sections 761 and 771 along corner folds 705 and 706, respectively. Additionally, the apex (most proximal) portion of the cone-shaped cusp is folded radially outward along the fold line 703 (between points U and V) to the position radially outward of the joined extension sections 718 and 728 such that the apex point 733 then lies upon the seam line 732.

Figure 7I:
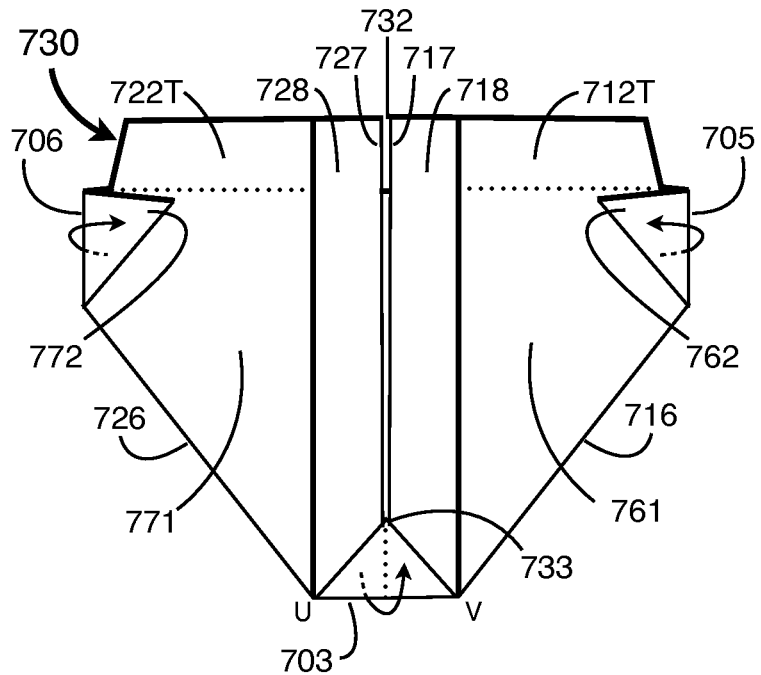
FIG. 7I is a plan view of the outer (abluminal) aspect of a completely folded version of an integrated cusp and leaflet folded structure prepared in accordance with the template shown in FIG. 7A.

FIG. 7I shows a plan view of the radially outer aspect of the completely folded integrated cusp and leaflet structure 730 of template 700. The outwardly folded position of the triangular commissure tabs 762 and 772 can be seen so that they lie in apposition to the outer surface of the cusp wall sections 761 and 771, respectively. While they may attached in this position to the underlying cusp wall layer and to the frame, alternatively, the commissure tabs 762 and 772 may be positioned to point radially outward (out of the page in this view) to pass through a slot or space in the frame to be secured and attached to the outer (abluminal) surface of the frame.

Additionally, the apex (most proximal) portion of the cone-shaped cusp is folded radially outward along the fold line 703 (between points U and V) to the position radially outward of the joined extension sections 718 and 728 such that the apex point 733 then lies upon the seam line 732.

The apex portion of the cone-shaped cusp thus configured is to be attached in this position as by suturing and may be similarly attached into this position in the act of attaching or suturing this portion of the folded cusp and leaflet structure to the frame.

Figure 7J:
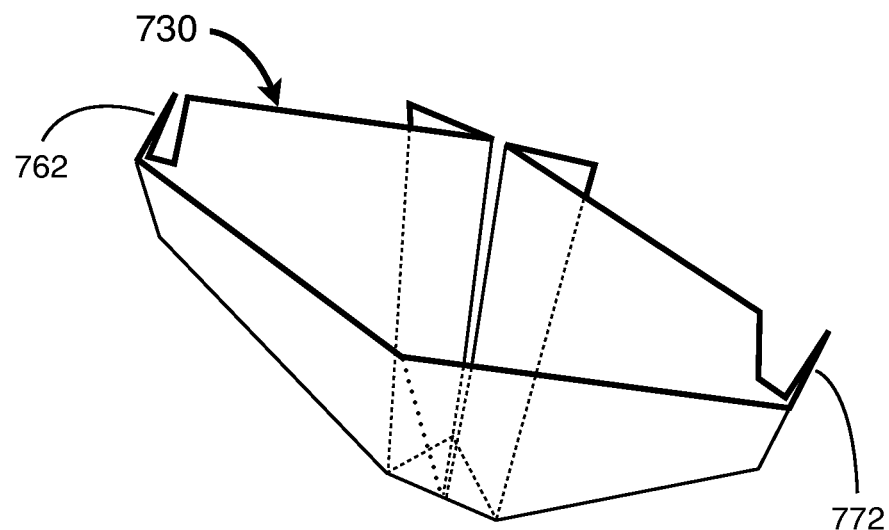
FIG. 7J is an oblique top (distal) perspective view of a completely folded version of an integrated cusp and leaflet folded structure prepared in accordance with the template shown in FIG. 7A.

FIG. 7J shows an oblique top perspective view of the completely folded and formed cusp and leaflet structure 730 with the view directed radially outward and downward (proximal). The cusp and leaflet structure is shown with the free edge of the mobile leaflet layer in the inward central position corresponding to the substantially closed operating position of the valve leaflet.

The commissure tabs 762 and 772 are depicted in radially aligned positions directed outward as would be required for passing them through slots or spaces in a suitably designed frame.

Figure 7K:
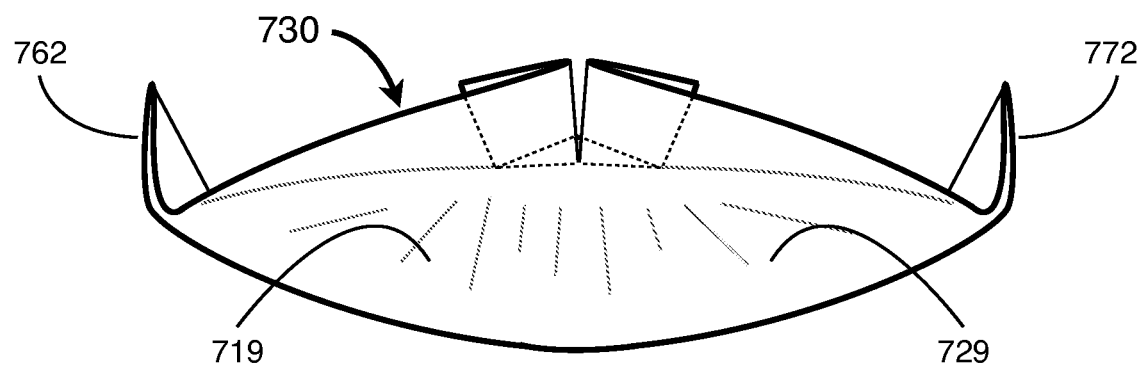
FIG. 7K is a top perspective view directed downward (proximal) into the cusp space of an integrated cusp and leaflet folded structure prepared in accordance with the template shown in FIG. 7A.

FIG. 7K shows a top perspective view of the single-piece completely folded and formed cusp and leaflet structure 730 with the view directed downward (proximal) into the cusp space. The cusp and leaflet structure is shown with the free edge of the mobile leaflet layer sections 719 and 729 in the intermediate inward position corresponding to the partially closed operating position of the valve leaflet.

The membrane structure is depicted with the free edges in a relaxed state corresponding to the typical behavior of tissue membranes when hydrated as when implanted in the body.

The commissure tabs 762 and 772 are depicted in radially aligned positions directed outward as would be required for passing them through slots or spaces in a suitably designed frame.

Metal Lattice Frame

Figure 8A:
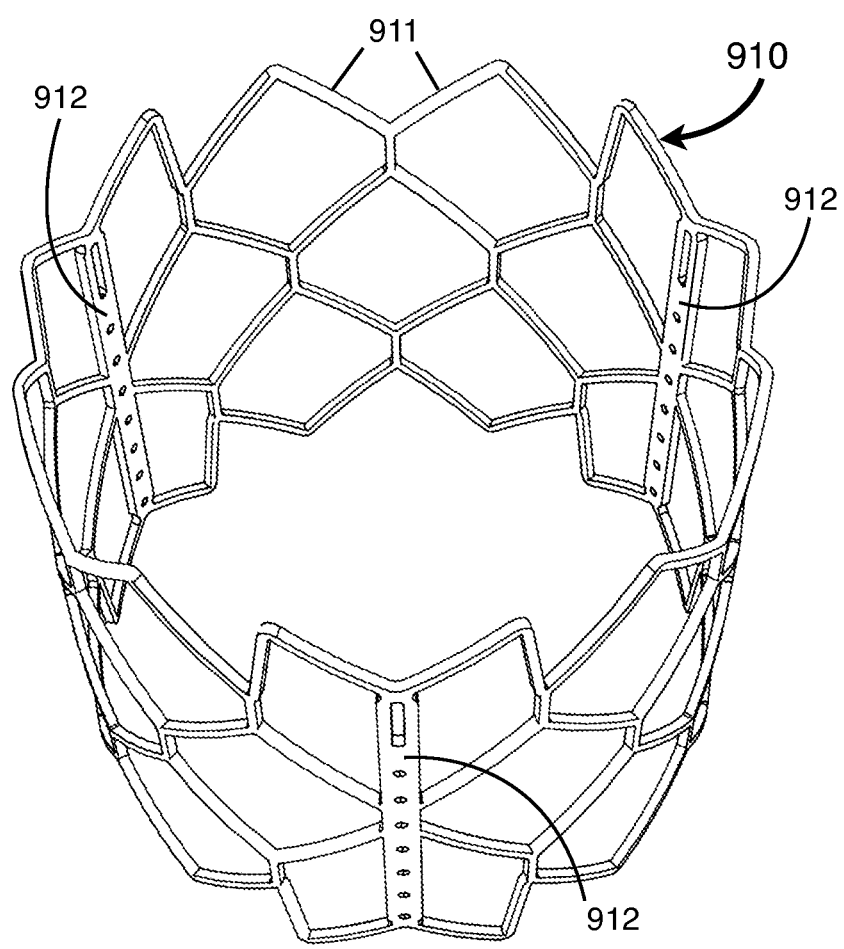
FIG. 8A is an oblique top (distal) perspective view of an embodiment of a lattice frame for mounting three of the single-piece folded integrated cusp and leaflet structures as described herein.

FIG. 8A is an oblique top perspective view of a metal lattice frame 910 for mounting three of the single-piece folded integrated cusp and leaflet structures of the ensuing description in order to form a three-leaflet valve. The frame comprises a plurality of strut members 911 and three axially oriented mounting bars 912 each with holes and/or slots for passing suture and/or portions of the folded membrane structure. Each mounting bar 912 is to align with and attach to the axial outer seam of one single-piece completely folded and formed cusp and leaflet structure 730. The diameter D of the open frame, e.g., 19-35 mm naturally defines the deployed and operating diameter of the valve assembly after implantation in the body. The strut members 911 are of specific length and orientation to permit radial collapse and compression of the frame to a small diameter, e.g., 3-7 mm. The mounting bars 912 are near to equally spaced around the circumferential course of the frame and the length L of the arc from the center of the mounting bar 912 to the center of the closest mounting bar 912 is approximately equal to (pi×D)/3. Thus defined, L also defines the transverse circumferential distance between folds 705 and 706, approximating the circumferential extent of the portions of the joined cusp wall sections 761 and 771 extending between 705 and 706 of the folded cusp and leaflet structure of appropriate size when mounted within the frame 910.

Figure 8B:
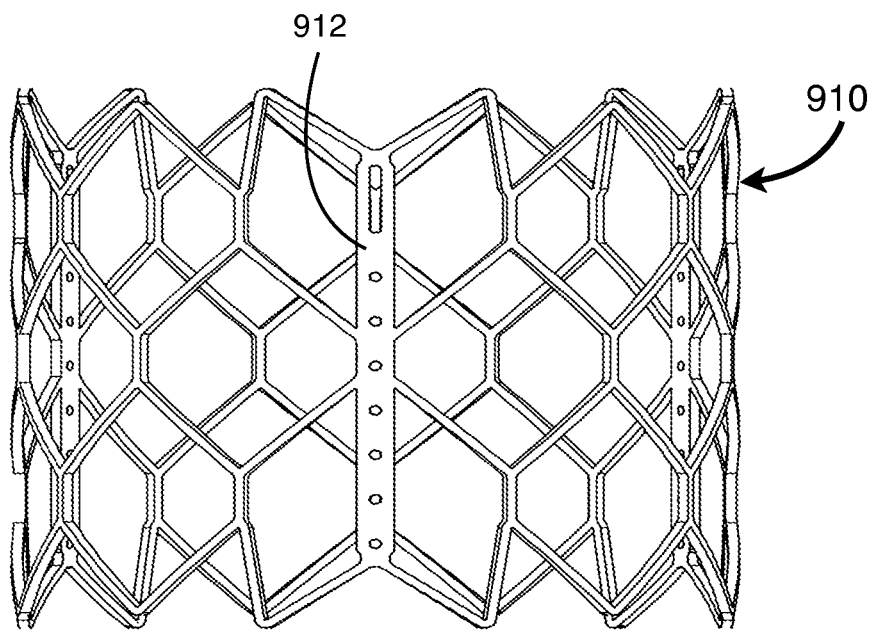
FIG. 8B is a side elevation view of the lattice frame shown in FIG. 8A.

FIG. 8B shows a side perspective view of the frame 910 with the view centered on the axial mounting bar 912. The axial bars are shown with holes and/or slots for passing suture and/or portions of the folded membrane structure to enable secure mounting of the folded cusp and leaflet structure within the frame.

Figure 8C:
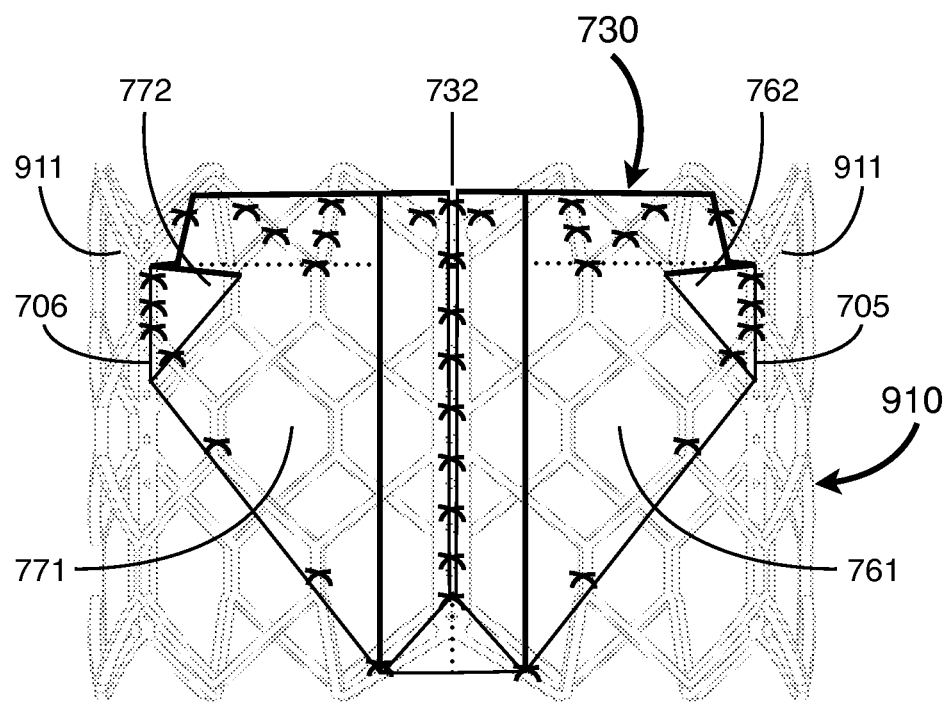
FIG. 8C is a side elevation view of the lattice frame of FIG. 8A with a superimposed plan view of the radially outer aspect of the completely folded integrated cusp and leaflet structure of FIG. 7I.

FIG. 8C shows a side view of the frame of FIG. 8B with a superimposed plan view of the radially outer aspect of the completely folded integrated cusp and leaflet structure as depicted in FIG. 7I. The cusp wall seam 732 is aligned upon the inner surface of the mounting bar of the frame and attached by sutures in this example. (Example suture locations are shown in FIGS. 8C, 9C and 9D shown with an "x"; however, it is to be understood that the locations shown are exemplary and not limiting.) As those skilled in the art will appreciate, means other than sutures for attaching folded integrated cusp and leaflet structure to the frame can be used.

The commissure tabs 762 and 772 are folded flat against the outer surface of the cusp wall layer along corner folds 705 and 706 for mounting entirely within the frame 910. Each fold 705 then forms an axially oriented seam along its length with the complementary fold 706 of the adjacent folded cusp and leaflet structure 730. (Adjacent complementary commissure tabs omitted for clarity.) Said seam is closed and attached by suture, for example, while also attaching to the radially overlying strut member 911 of the frame 910, and thereby affixes the distal margins of the cusp wall sections 761 and 771 and the mobile leaflet sections (obverse of this view) to the frame 910. The other suture points depicted attach only the cusp wall layer 761+771 to the overlying frame strut members 911. At no point within the interior operating volume of the valve is the mobile leaflet layer 719+729 penetrated by suture. This uninterrupted continuity of the operating leaflet material afforded by the folded design of the integrated cusp and leaflet structure endows the valve and its leaflets with strength, durability and resistance to stress damage at suture holes.

Figure 8D:
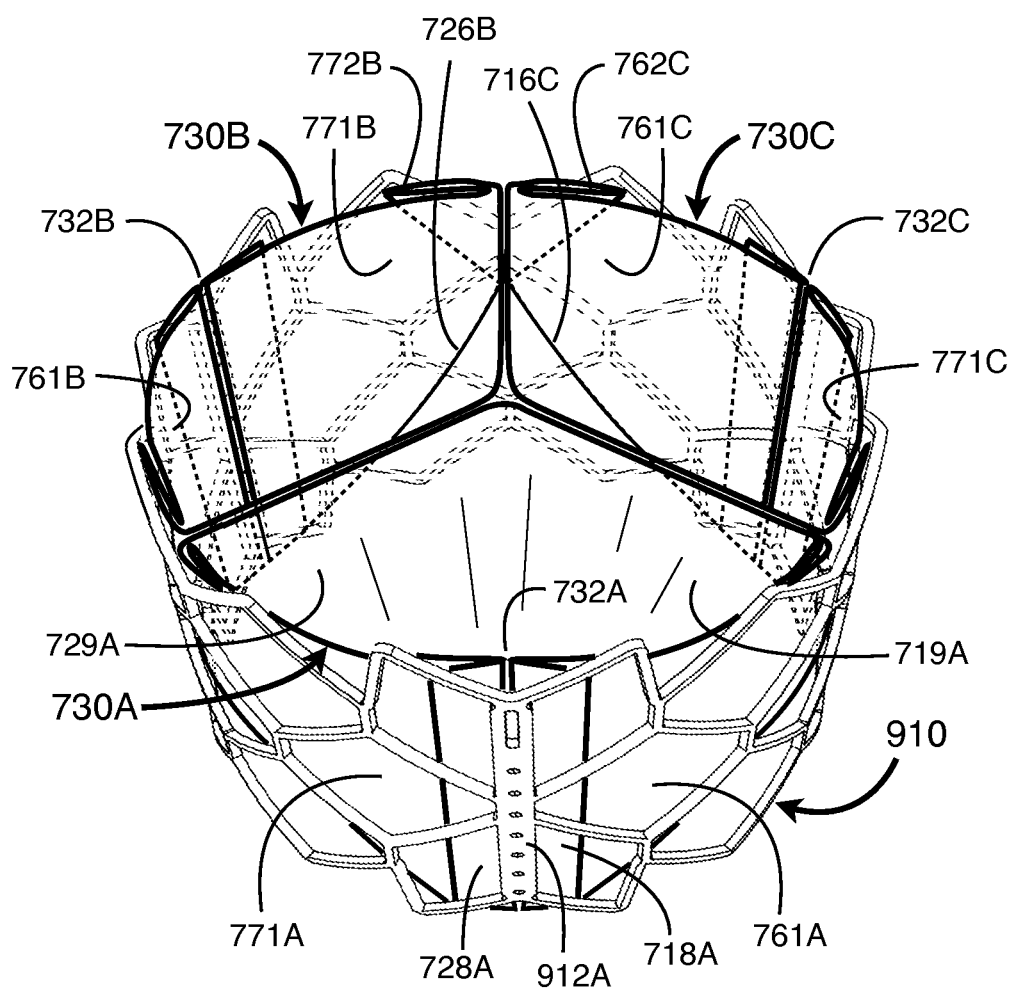
FIG. 8D is an oblique axial (top/distal) perspective view of an assembled three-leaflet valve in accordance with at least one embodiment.

FIG. 8D shows an oblique axial (top/distal) perspective view of the assembled three-leaflet valve comprising the frame 910 and three identical folded integrated cusp and leaflet structures 730A, 730B and 730C attached within the frame with the view centered on an axial mounting bar 912A. The suture attachments are omitted for clarity. The cusp and leaflet structure 730A nearest in view is seen within the frame 910, with the outer aspect of the seam 732A, cuff wall extension sections 718A and 728A, and cusp wall sections 761A and 771A viewed through the interspaces of the frame 910. The seam 732A is aligned to the overlying axial mounting bar 912A to which it is attached along its length. The inner (luminal) aspect of the seams 732B and 732C and the cusp wall sections 761B, 771B, 761C and 771C of the other two folded cusp and leaflet structures 730B and 730C, respectively are seen on the far side of the view. The adjoined folded edges of the membrane portions of the commissure tabs 772B and 762C are shown in the far view in position opposite to the axial mounting bar 912A in the near view. The radially outward surface of the mobile leaflet sections 719A and 729A of the folded cusp and leaflet structure 730A is shown in the near view. The distal free edges of all three mobile leaflets are shown in the centrally apposed (coapted) position corresponding to the closed operating position of the valve. FIG. 8D also shows in that aspect interior to the cusps, folds 726B of cusp and leaflet structure 730B and 716C of cusp and leaflet structure 730C as they form the lower (proximal) boundary of the valve cusps.

Slotted Lattice Frame

Figure 9A:
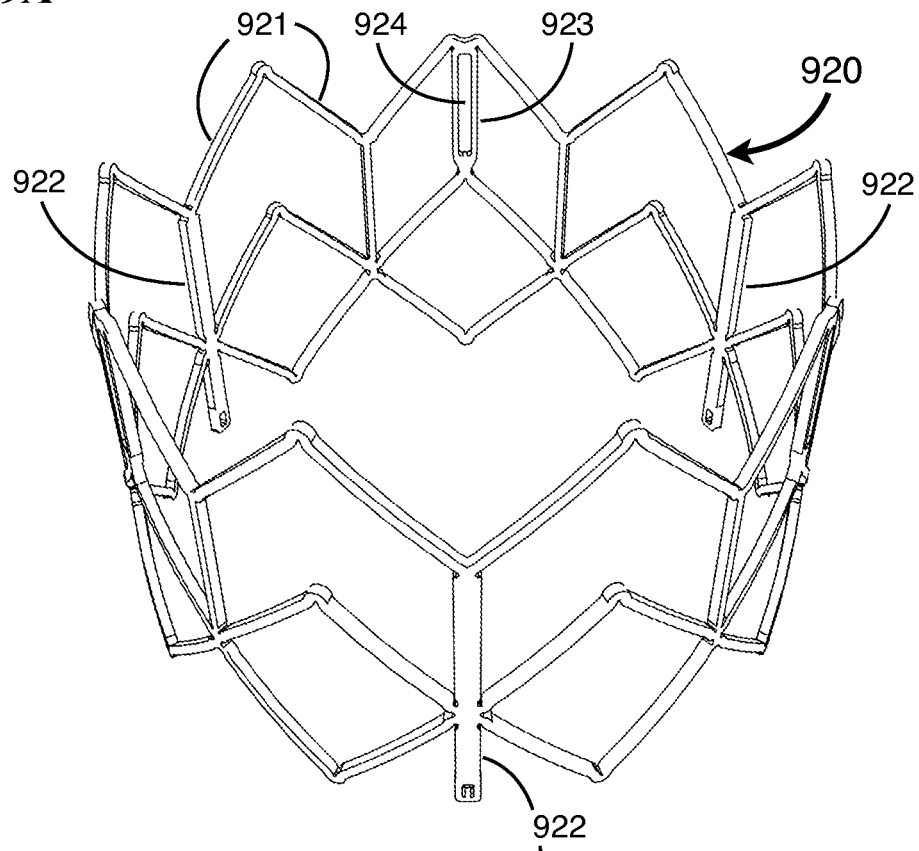
FIGS. 9A and 9B are two different oblique axial (top/distal) perspective views of another embodiment of a lattice frame for mounting three of the single-piece folded integrated cusp and leaflet structures that include commissure tabs.

FIG. 9A shows an oblique axial (top/distal) perspective view of a frame 920 of a design to receive the commissure tabs 762 and 772 through slots 924 in slotted members 923 in order that the tabs are secured and attached to the outer (abluminal) aspect of the frame. This approach to mounting and attaching the commissure tabs enables the loading forces on the leaflet commissures during valve operation to be advantageously distributed upon the frame slotted members 923 along their length rather than upon suture that directly tethers the leaflets, thus greatly reducing the risk of tearing of the material at points of suture penetration. The frame further comprises axial mounting bars 922 for mounting the central seams 732 joining the cusp wall sections 761 and 771 along folds 717 and 727. The frame further comprises a plurality of strut members 921 that otherwise form the metal lattice of the frame.

Each mounting bar 922 is to align with and attach to the axial outer seam of one single-piece completely folded and formed cusp and leaflet structure 730. The inner diameter D of the open frame, e.g., 19-35 mm naturally defines the deployed and operating diameter of the valve assembly after implantation in the body. The strut members 921 are of specific length and orientation to permit radial collapse and compression of the frame to a small diameter, e.g., 3-7 mm. The mounting bars 922 are near to equally spaced around the inner circumferential course of the frame. The length L of the arc along the inner circumference of the frame from the center of the mounting bar 922 to the center of the closest mounting bar 922 is approximately equal to (pi×D)/3. Thus defined, L also defines the transverse circumferential distance between folds 705 and 706, approximating the circumferential extent of the portions of the joined cusp wall sections 761 and 771 extending between 705 and 706 of the folded cusp and leaflet structure of appropriate size when mounted within the frame 920.

The axial mounting bars 922 optionally contain holes and/or slots to facilitate suture attachment of the folded integrated cusp and leaflet structures 730. The frame is depicted in FIGS. 9A-9E as having axial mounting bars 922 each with a hole near the proximal end to facilitate suture attachment of the apical (most proximal) portion of the folded cusp and leaflet structure.

Figure 9B:
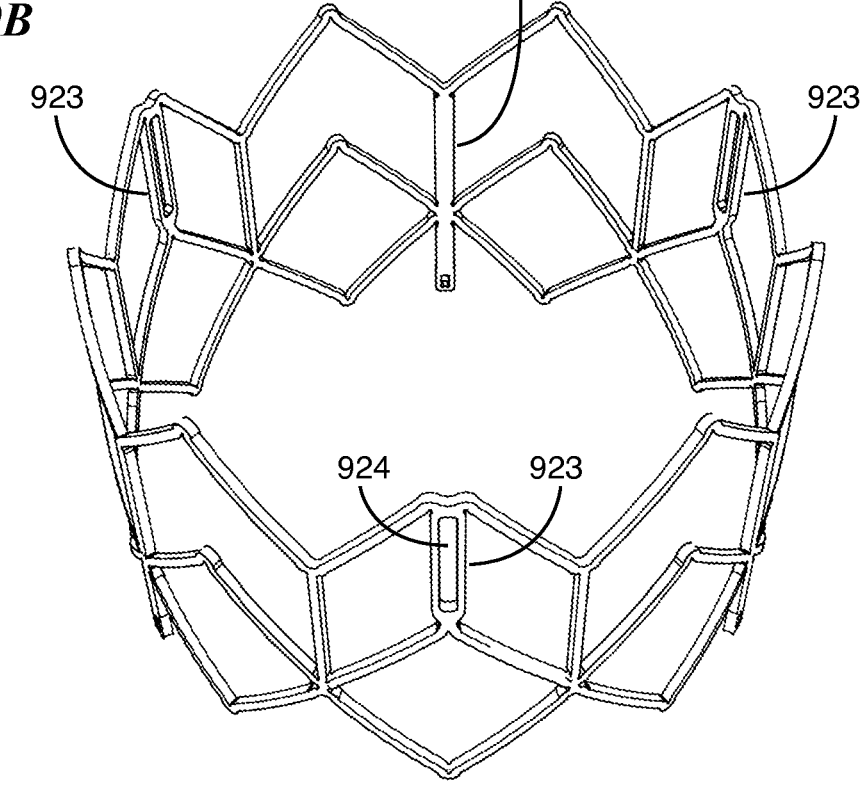
Figure 9C:
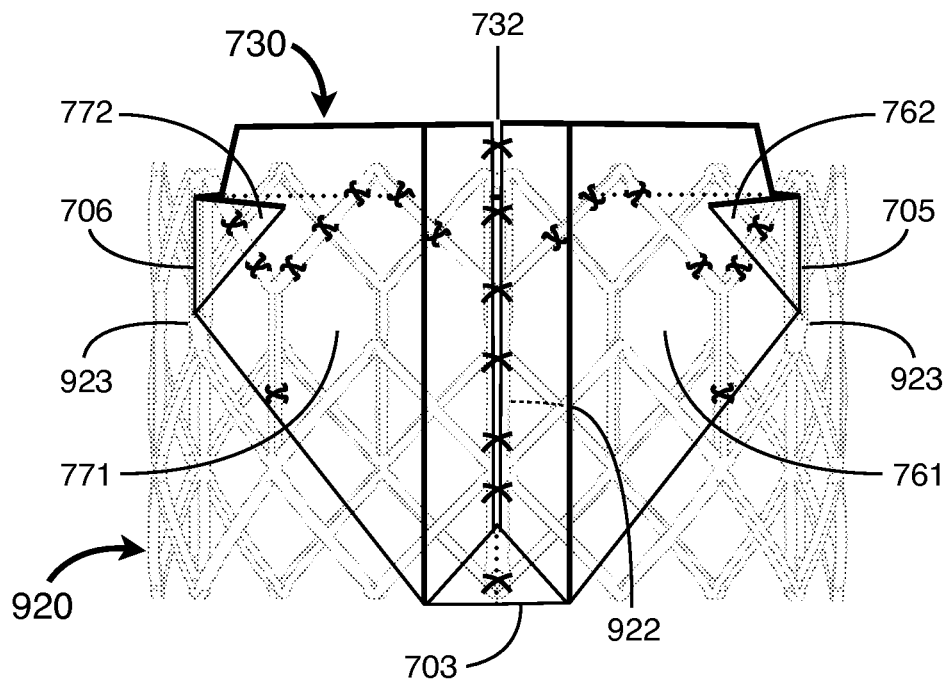
FIG. 9C is a side perspective view of the lattice frame shown in FIGS. 9A and 9B with a superimposed plan view of the outer aspect of the completely folded integrated cusp and leaflet structure of FIG. 7I.
Figure 9D:
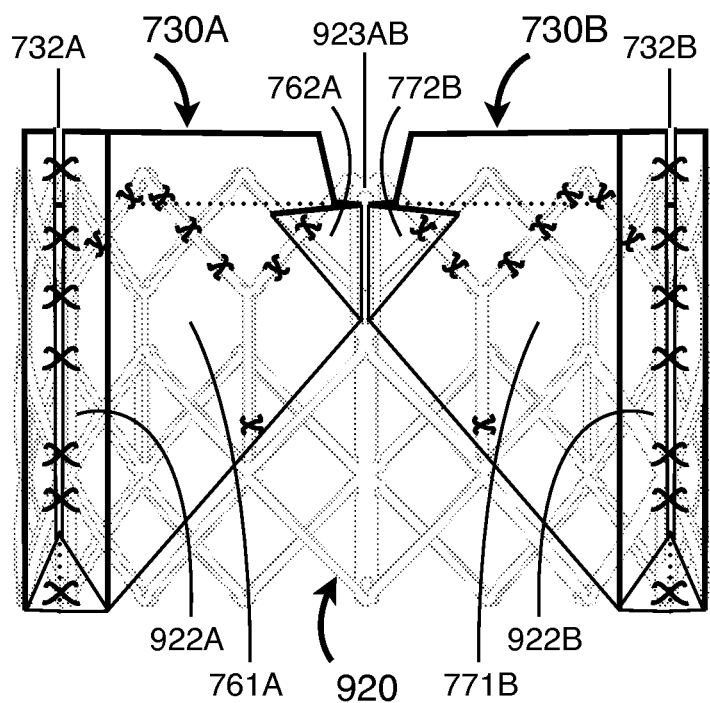
FIG. 9D is a side view of the lattice frame shown in FIGS. 9A and 9B with superimposed views of the outer aspect of two circumferentially adjacent completely folded integrated cusp and leaflet structures.

FIG. 9B shows the metal lattice frame of FIG. 9A in the same perspective, but with the view centered on the slotted frame member 923.

FIG. 9C shows a side perspective view of the frame 920 centered on the axial mounting bar 922 with a superimposed plan view of the outer aspect of the completely folded integrated cusp and leaflet structure 730 (of FIG. 7I) as mounted within the frame 920 to demonstrate the relationships between the two. An example suture pattern for attachment is shown. The cusp wall seam 732 is aligned upon the inner surface of the mounting bar 922 of the frame 920 and attached by sutures in this example.

The commissure tabs 762 and 772 are to be understood as having been passed through the frame slots 924 from within the central space of the frame to the outer (abluminal) side and folded along 705 and 706, respectively onto the outer surface of the cusp and leaflet structure where they are attached along their common length both to the frame members 923 and, through the interspaces of the frame 920, to the radially underlying outer aspect of the cusp wall sections 761 and 771, respectively. The adjacent cusp and leaflet structures of the three-leaflet valve are not shown for clarity. The joining of adjacent commissure tabs at the slotted members 923 is demonstrated in FIG. 9D.

At the apical (most proximal) extent of the completely folded integrated cusp and leaflet structure 730, the apical portion folded radially outward along fold 703 is attached to the lower (most proximal) end of the axial mounting bar 922. When present, a hole near the end of the axial mounting bar 922 facilitates suture attachment at this point.

FIG. 9D shows a side perspective view of the frame 920 centered on the slotted frame member 923AB with a superimposed perspective view of the outer aspect of two circumferentially adjacent completely folded integrated cusp and leaflet structures 730A and 730B (of FIG. 7I) to demonstrate their relationships as mounted within the frame 920. An example suture pattern for attachment is shown. Suture attachment of the commissure folds 705 and 706 at the level of the slot is notably absent. Rather, attachment of the bodies of the commissure tabs 762A and 772B to the outer aspect of the frame at points removed from the free edges and folds of the material avoids suture penetration along the lines of traction in the slot and enhances the resistance of the structure to tearing at such suture attachments. The cusp wall seams 732A and 732B are aligned upon the inner surface of the mounting bars 922A and 922B, respectively of the frame 920 and attached by sutures in this example.

The commissure tabs 762A and 772B are to be understood as having been passed through the frame slot 924 from within the central space of the frame to the outer (abluminal) side and folded along 705A and 706B, respectively onto the outer surface of the cusp and leaflet structure where they are attached along their common length both to the frame member 923AB and, through the interspaces of the frame 920, to the radially underlying outer aspect of the cusp wall sections 761A and 771B, respectively.

Figure 9E:
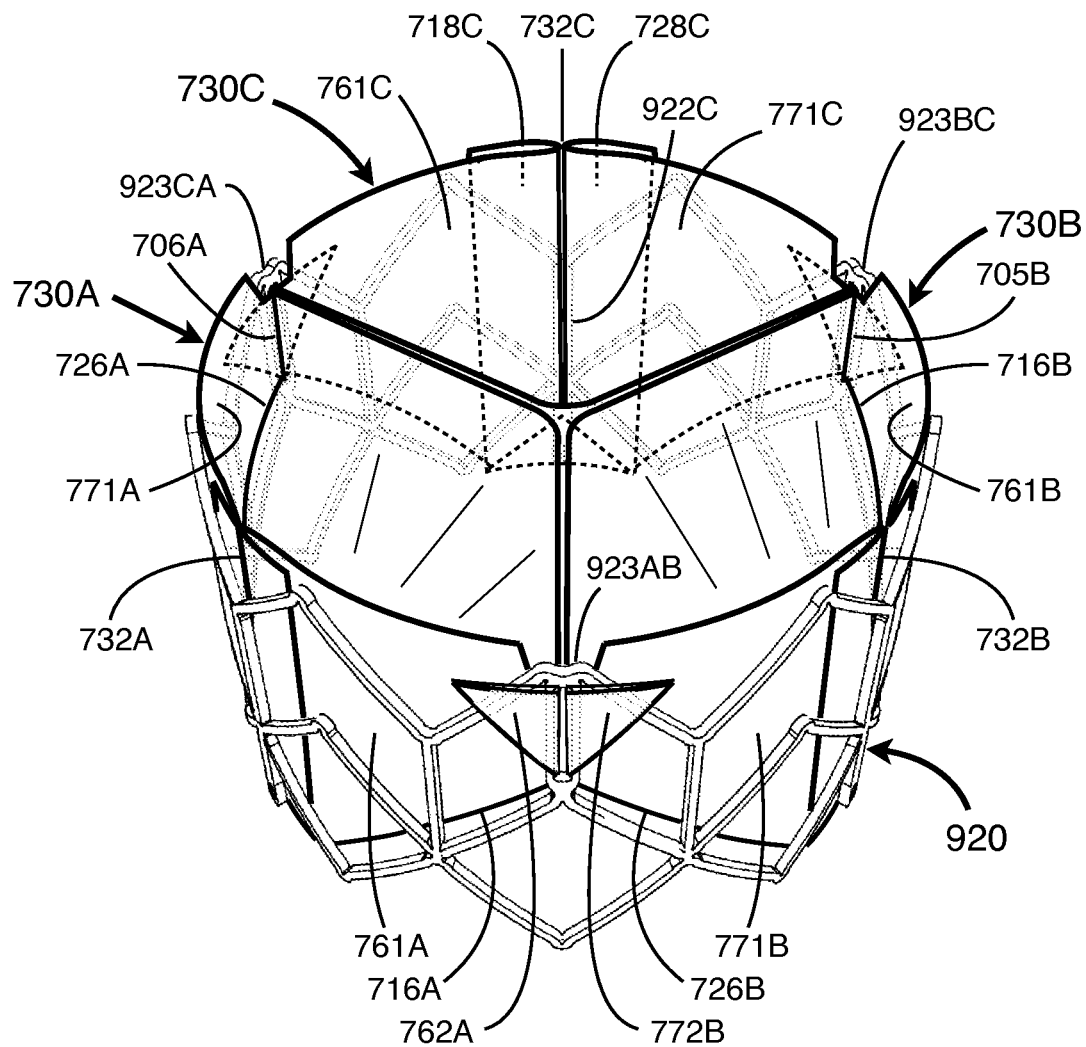
FIG. 9E is an oblique axial (top/distal) perspective view of an assembled three-leaflet valve comprising the lattice frame shown in FIGS. 9A and 9B and three identical folded integrated cusp and leaflet structures.

FIG. 9E shows an oblique axial (top/distal) perspective view of the assembled three-leaflet valve comprising the frame 920 and three identical folded integrated cusp and leaflet structures 730A, 730B and 730C attached principally within the central space of the frame, but with the commissure tabs passed in complementary adjacent left-right pairs, 762A-772B, 762B-772C and 762C-772A, through the slots 924AB, 924BC and 924CA, of slotted frame members 923AB, 923BC, and 923CA, respectively. The view is centered on slotted member 923AB. The suture attachments are omitted for clarity.

The cusp and leaflet structure 730C farthest in view is seen within the frame 920, with the inner aspect of the seam 732C and cusp wall sections 761C and 771C in the far view. The cuff wall extension sections 718C and 728C are depicted as folded onto the outer aspect of the cusp wall sections 761C and 771C, respectively, but within the central space of the frame 920 and apposed to the inner surface of the frame. The inner (luminal) aspect of the seam 732C is shown aligned to the outwardly overlying axial mounting bar 922C to which it is attached along its length. The outer (abluminal) aspect of the top (most distal) portions of the seams 732A and 732B and the cusp wall sections 761A and 771B, of the other two folded cusp and leaflet structures 730A and 730B are also shown through the interspaces of the frame on either side of the near view.

The commissure tabs 762A and 772B, aligned and apposed along folds 705A and 706B, respectively are shown centered in the near view in position opposite to the axial mounting bar 922C and cusp wall seam 732C in the far view. The key mounting configuration of the valve commissures to the slotted frame members is here demonstrated. The triangular commissure tabs are formed as a result of the folding of the membrane template along folds 716 and 726, and are comprised of overlapping layers of the cusp wall section and the mobile leaflet section. Thus, with passage of the commissure tabs from within the interior space of the frame through the frame slots, both the cusp wall layer and the mobile leaflet layer are carried together to the outer aspect of the frame where they are attached. In addition, the interior aspect of the commissure folds 706A of cusp and leaflet structure 730A and 705B of cusp and leaflet structure 730B are shown where they mark the segment at which the commissure tabs 772A and 762B are passed through the frame slots 924CA and 924BC of slotted members 923CA and 923BC, respectively, and are tethered thereto.

The radially outward surface of the mobile leaflet sections 719A, 729A of the folded cusp and leaflet structure 730A and sections 719B, 729B of the folded cusp and leaflet structure 730B are shown on the left and right sides, respectively of the near view. (These labels omitted for clarity.)

The distal free edges of all three mobile leaflets are shown in the centrally apposed (coapted) position corresponding to the closed operating position of the valve. FIG. 9E also shows in that aspect interior to the cusps, a portion of folds 726A of cusp and leaflet structure 730A and 716B of cusp and leaflet structure 730B as they form the lower (proximal) boundary of the valve cusps.

The template examples disclosed herein are provided for enablement purposes and shall not be interpreted as limiting the scope of the claims. For example, angular values shown and/or described herein are not to be interpreted as limiting the scope of a claim unless included in a given claim.

As those skilled in the art will appreciate, circumference length varies with the diameter circumscribed therein. Accordingly, refinements in the valve manufacturing process may address adjusting the length of the leaflet free edge to be slightly less than the edge length of the cusp wall, i.e., less than the circumferential arc length between the commissures. This adjustment depends upon the dimensions of a given valve in production, as well as the dimensions of the given valve's component elements.

In still other embodiments of the one or more present inventions, the percutaneously deliverable heart valve may include various other configurations by using different variations of the polygon pattern, so as to include, for example, an inner sealing cuff for the valve that is continuous and integral with the leaflet structure itself. In yet other embodiments, the percutaneously deliverable heart valve may include different configurations by adjusting the pattern and folding technique, such as the angle of the cone and its surface area, or the extent of apposition between the leaflets may also be specified.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A transcatheter, implantable, prosthetic heart valve, comprising:
   a lattice frame that is collapsible and expandable, the lattice frame comprising a plurality of strut members; and
   a biocompatible membrane attached to the lattice frame, the biocompatible membrane including a plurality of operating leaflet structures located radially interior to the lattice frame, wherein when in a position corresponding to a closed operating configuration each operating leaflet structure of the plurality of operating leaflet structures forms a conical shape, a substantially conical shape, a truncated-conical shape, or an inverted pyramid shape.

2. The transcatheter, implantable, prosthetic heart valve of claim 1, further comprising a cuff attached to the lattice frame.

3. The transcatheter, implantable, prosthetic heart valve of claim 2, wherein the cuff comprises biocompatible membrane attached to an abluminal surface of the lattice frame.

4. The transcatheter, implantable, prosthetic heart valve of claim 2, wherein the cuff comprises biocompatible membrane attached radially interior of the lattice frame.

5. The transcatheter, implantable, prosthetic heart valve of claim 4, wherein the cuff is not circumferentially complete.

6. The transcatheter, implantable, prosthetic heart valve of claim 1, wherein the biocompatible membrane is a plurality of pieces of material.

7. The transcatheter, implantable, prosthetic heart valve of claim 1, wherein the biocompatible membrane includes two to fifty pieces of material.

8. The transcatheter, implantable, prosthetic heart valve of claim 1, wherein each operating leaflet structure of the plurality of operating leaflet structures is attached to the lattice frame at a seam, wherein each seam is located along a centerline of each operating leaflet structure.

9. The transcatheter, implantable, prosthetic heart valve of claim 8, wherein each seam is not circumferentially coincident with a valve commissure.

10. A transcatheter, implantable, prosthetic heart valve, comprising:
a lattice frame that is collapsible and expandable; and
a biocompatible membrane attached to the lattice frame, the biocompatible membrane including a plurality of operating leaflet structures located radially interior to the lattice frame, wherein each operating leaflet structure of the plurality of operating leaflet structures is attached to the lattice frame at a plurality of points along a seam located along a centerline of each operating leaflet structure.

11. The transcatheter, implantable, prosthetic heart valve of claim 10, further comprising a cuff attached to the lattice frame.

12. The transcatheter, implantable, prosthetic heart valve of claim 11, wherein the cuff comprises biocompatible membrane attached to an abluminal surface of the lattice frame.

13. The transcatheter, implantable, prosthetic heart valve of claim 11, wherein the cuff comprises biocompatible membrane attached radially interior of the lattice frame.

14. The transcatheter, implantable, prosthetic heart valve of claim 13, wherein the cuff is not circumferentially complete.

15. The transcatheter, implantable, prosthetic heart valve of claim 10, wherein the biocompatible membrane is a plurality of pieces of material.

16. The transcatheter, implantable, prosthetic heart valve of claim 10, wherein the biocompatible membrane includes two to fifty pieces of material.

17. The transcatheter, implantable, prosthetic heart valve of claim 10, wherein each seam is not circumferentially coincident with a valve commissure.

18. The transcatheter, implantable, prosthetic heart valve of claim 10, wherein each operating leaflet structure of the plurality of operating leaflet structures forms a conical shape when in a position corresponding to a closed operating configuration.

19. A transcatheter, implantable, prosthetic heart valve, comprising:
a lattice frame that is collapsible and expandable; and
a biocompatible membrane attached to the lattice frame, the biocompatible membrane including a plurality of operating leaflet structures located radially interior to the lattice frame, wherein each operating leaflet structure of the plurality of operating leaflet structures is attached to the lattice frame by a non-commissure seam that is not circumferentially coincident with a valve commissure, and wherein the non-commissure seam is aligned substantially parallel to an axis of the lattice frame.

20. The transcatheter, implantable, prosthetic heart valve of claim 19, further comprising a cuff attached to the lattice frame.

21. The transcatheter, implantable, prosthetic heart valve of claim 20, wherein the cuff comprises biocompatible membrane attached to an abluminal surface of the lattice frame.

22. The transcatheter, implantable, prosthetic heart valve of claim 20, wherein the cuff comprises biocompatible membrane attached radially interior of the lattice frame.

23. The transcatheter, implantable, prosthetic heart valve of claim 22, wherein the cuff is not circumferentially complete.

24. The transcatheter, implantable, prosthetic heart valve of claim 19, wherein the biocompatible membrane is a plurality of pieces of material.

25. The transcatheter, implantable, prosthetic heart valve of claim 19, wherein the biocompatible membrane includes two to fifty pieces of material.

26. The transcatheter, implantable, prosthetic heart valve of claim 19, wherein when in a position corresponding to a closed operating configuration each operating leaflet structure of the plurality of operating leaflet structures forms a conical shape, a substantially conical shape, a truncated-conical shape, or an inverted pyramid shape.

27. A transcatheter, implantable, prosthetic heart valve, comprising:
a lattice frame that is collapsible and expandable; and
a biocompatible membrane attached to the lattice frame, the biocompatible membrane including a plurality of operating leaflet structures located radially interior to the lattice frame, wherein each operating leaflet structure of the plurality of operating leaflet structures includes a mobile leaflet layer attached to a cusp wall layer at least along a first straight-line border attached to the lattice frame and a second straight-line border attached to the lattice frame, wherein the first and second straight-line borders are not parallel to an axial center of the lattice frame.

28. The transcatheter, implantable, prosthetic heart valve of claim 27, further comprising a cuff attached to the lattice frame.

29. The transcatheter, implantable, prosthetic heart valve of claim 28, wherein the cuff comprises biocompatible membrane attached to an abluminal surface of the lattice frame.

30. The transcatheter, implantable, prosthetic heart valve of claim 28, wherein the cuff comprises biocompatible membrane attached radially interior of the lattice frame.

31. The transcatheter, implantable, prosthetic heart valve of claim 30, wherein the cuff is not circumferentially complete.

32. The transcatheter, implantable, prosthetic heart valve of claim 27, wherein the biocompatible membrane is a plurality of pieces of material.

33. The transcatheter, implantable, prosthetic heart valve of claim 27, wherein the biocompatible membrane includes two to fifty pieces of material.

34. The transcatheter, implantable, prosthetic heart valve of claim 27, wherein when in a position corresponding to a closed operating configuration each operating leaflet structure of the plurality of operating leaflet structures forms a conical shape, a substantially conical shape, a truncated-conical shape, or an inverted pyramid shape.

* * * * *